(12) United States Patent
Kambe et al.

(10) Patent No.: US 10,411,212 B2
(45) Date of Patent: Sep. 10, 2019

(54) ORGANIC ELECTROLUMINESCENT ELEMENT

(71) Applicants: Sony Corporation, Minato-ku, Tokyo (JP); Idemitsu Kosan Co., Ltd., Tokyo (JP)

(72) Inventors: Emiko Kambe, Atsugi (JP); Masato Nakamura, Atsugi (JP); Jun Endo, Sodegaura (JP); Masakazu Funahashi, Sodegaura (JP); Hironobu Morishita, Sodegaura (JP)

(73) Assignees: IDEMITSU KOSAN CO., LTD., Tokyo (JP); JOLED INC., Tokyo (JP)

( * ) Notice: Subject to any disclaimer, the term of this patent is extended or adjusted under 35 U.S.C. 154(b) by 561 days.

(21) Appl. No.: 14/349,626

(22) PCT Filed: Oct. 2, 2012

(86) PCT No.: PCT/JP2012/006296
§ 371 (c)(1),
(2) Date: Apr. 3, 2014

(87) PCT Pub. No.: WO2013/051234
PCT Pub. Date: Apr. 11, 2013

(65) Prior Publication Data
US 2014/0246663 A1 Sep. 4, 2014

(30) Foreign Application Priority Data
Oct. 4, 2011 (JP) .................................. 2011-220121

(51) Int. Cl.
*H01L 27/32* (2006.01)
*H01L 51/00* (2006.01)
(Continued)

(52) U.S. Cl.
CPC .......... *H01L 51/504* (2013.01); *C07D 215/30* (2013.01); *C07D 235/08* (2013.01);
(Continued)

(58) Field of Classification Search
CPC .. C07D 215/30; C07D 235/08; C07D 241/36; C07D 471/04; C07D 487/14;
(Continued)

(56) References Cited

U.S. PATENT DOCUMENTS 6,107,734 A 8/2000 Tanaka et al.
6,534,199 B1 * 3/2003 Hosokawa .......... H01L 51/0052
252/301.16
(Continued)

FOREIGN PATENT DOCUMENTS

JP 11-329748 A 11/1999
JP 2003-045676 A 2/2003
(Continued)

OTHER PUBLICATIONS

International Searching Authority, International Search Report received in International Application No. PCT/JP2012/006296 dated Apr. 17, 2014.
(Continued)

*Primary Examiner* — Dawn L Garrett
(74) *Attorney, Agent, or Firm* — Foley & Lardner LLP

(57) ABSTRACT

An organic electroluminescence device including: an anode; a cathode; two or more emitting units that are disposed between the anode and the cathode, each unit having an emitting layer; and a charge-generating layer that is disposed between the emitting units, wherein the charge-generating layer comprises an N layer nearer to the anode and a P layer nearer to the cathode, and the P layer comprises a compound represented by the following formula (I).

(Continued)

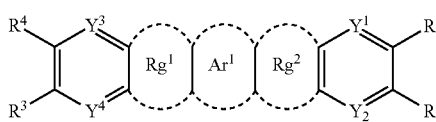

(I)

20 Claims, 3 Drawing Sheets

(51) Int. Cl.
H01L 51/50 (2006.01)
H01L 51/52 (2006.01)
C07D 235/08 (2006.01)
C07D 241/36 (2006.01)
C07D 471/04 (2006.01)
C07D 487/14 (2006.01)
C07D 487/22 (2006.01)
C07D 215/30 (2006.01)

(52) U.S. Cl.
CPC ......... *C07D 241/36* (2013.01); *C07D 471/04* (2013.01); *C07D 487/14* (2013.01); *C07D 487/22* (2013.01); *H01L 51/0051* (2013.01); *H01L 51/0055* (2013.01); *H01L 51/0056* (2013.01); *H01L 51/0067* (2013.01); *H01L 51/0072* (2013.01); *H01L 51/5278* (2013.01); *H01L 27/322* (2013.01); *H01L 27/3209* (2013.01); *H01L 27/3281* (2013.01)

(58) Field of Classification Search
CPC . C07D 487/22; H01L 27/3209; H01L 27/322; H01L 27/3281; H01L 51/0051; H01L 51/0055; H01L 51/0056; H01L 51/0067; H01L 51/0072; H01L 51/504; H01L 51/5278
See application file for complete search history.

(56) References Cited

U.S. PATENT DOCUMENTS

| | | | |
|---|---|---|---|
| 6,872,472 B2 | 3/2005 | Liao et al. | |
| 7,736,754 B2 | 6/2010 | Kijima et al. | |
| 8,080,934 B2 | 12/2011 | Kido et al. | |
| 8,101,857 B2 | 1/2012 | Kido et al. | |
| 8,482,193 B2 | 7/2013 | Kido et al. | |
| 8,603,642 B2 | 12/2013 | Hatwar et al. | |
| 8,633,475 B2* | 1/2014 | Endo | H01L 51/5044 257/40 |
| 9,099,682 B2* | 8/2015 | Nowatari | H01L 51/5278 |
| 9,978,975 B2* | 5/2018 | Kambe | H01L 51/504 |
| 2003/0170491 A1* | 9/2003 | Liao | H01L 51/5036 428/690 |
| 2003/0189401 A1 | 10/2003 | Kido et al. | |
| 2004/0227460 A1* | 11/2004 | Liao | H01L 51/5278 313/506 |
| 2005/0029933 A1 | 2/2005 | Liao et al. | |
| 2006/0008740 A1 | 1/2006 | Kido et al. | |
| 2006/0188745 A1* | 8/2006 | Liao | H01L 51/5278 428/690 |
| 2007/0181887 A1 | 8/2007 | Kijima et al. | |
| 2007/0182317 A1 | 8/2007 | Kido et al. | |
| 2010/0019659 A1* | 1/2010 | Morishita | C07C 255/34 313/504 |
| 2010/0193773 A1* | 8/2010 | Yamamoto | C07D 235/18 257/40 |
| 2010/0288362 A1 | 11/2010 | Hatwar et al. | |
| 2010/0301318 A1 | 12/2010 | Kuma et al. | |
| 2011/0284827 A1 | 11/2011 | Morishita et al. | |
| 2012/0012820 A1* | 1/2012 | Endo | H01L 51/5278 257/40 |
| 2012/0118350 A1 | 5/2012 | Kido et al. | |
| 2012/0132895 A1 | 5/2012 | Kido et al. | |
| 2012/0223346 A1* | 9/2012 | Ohsawa | H01L 27/3206 257/89 |
| 2014/0001457 A1 | 1/2014 | Endo | |
| 2014/0001461 A1 | 1/2014 | Morishita et al. | |
| 2015/0155513 A1* | 6/2015 | Pieh | H01L 27/3209 257/40 |
| 2015/0303380 A1* | 10/2015 | Kambe | C07D 487/14 257/40 |

FOREIGN PATENT DOCUMENTS

| | | |
|---|---|---|
| JP | 2003-272860 A | 9/2003 |
| JP | 2004-039617 A | 2/2004 |
| JP | 2006-024791 A | 1/2006 |
| JP | 2006-073484 A | 3/2006 |
| JP | 2006-173550 A | 6/2006 |
| JP | 2010-192719 A * | 9/2010 |
| JP | 2012-022953 A | 2/2012 |
| JP | 2012-49088 A | 3/2012 |
| JP | 2012-195054 A | 10/2012 |
| KR | 10-0911555 B1 | 8/2009 |
| KR | 10-2011-0099239 A | 9/2011 |
| TW | 201106515 A1 | 2/2011 |
| WO | WO-2004/080975 A1 | 9/2004 |
| WO | WO-2009/011327 A1 | 1/2009 |
| WO | WO-2010/064655 A1 | 6/2010 |
| WO | WO-2010/134350 A1 | 11/2010 |

OTHER PUBLICATIONS

Office Action issued in Taiwan Patent Application No. 101136651 dated May 23, 2016.
Office Action dated May 9, 2017 in corresponding Japanese Patent Application No. 2013-537408.
Korean Office Action dated Jan. 25, 2019 in corresponding application No. 10-2014-7007748.

* cited by examiner

ORGANIC ELECTROLUMINESCENT ELEMENT

CROSS-REFERENCE TO RELATED APPLICATIONS

This application is the National Phase of International Patent Application No. PCT/JP2012/006296, filed Oct. 2, 2012, which claims the benefit of priority from Japanese Patent Application No. 2011-220121, filed Oct. 4, 2011. The contents of these applications are incorporated herein by reference in their entirety.

TECHNICAL FIELD

The invention relates to an organic electroluminescence (EL) device, in particular, a stacked-type multi-photon emission device (MPE device) having two or more emitting units.

BACKGROUND ART

A common organic EL device comprises an anode composed of ITO or the like provided on a substrate, an organic layer provided on the anode, and a cathode provided thereon. The organic layer has a constitution in which a hole-injecting layer, a hole-transporting layer and an emitting layer are stacked in this sequence from the anode, for example. In the organic EL device having such a constitution, light generated when electrons injected from the cathode and holes injected from the anode are recombined in the emitting layer is outcoupled from the substrate side.

The life of an organic EL device is generally determined by the amount of injected charges. This leads to a problem that the life is shortened when a driving current is increased in order to increase an initial luminance.

In order to solve the problem, it is necessary to increase the luminance without changing the driving current, i.e. to improve the efficiency, or to realize a device constitution which does not deteriorate the luminance even when the driving current is reduced.

For the above-mentioned device constitution, a constitution in which plural emitting units each comprising organic layers including at least an emitting layer are stacked between an anode and a cathode via insulating charge-generating layers (MPE device) has been proposed. Here, the charge-generating layer is a layer which, when a voltage is applied, serves to inject holes to an emitting unit arranged on the side of a charge-generating layer near to a cathode, and on the other hand, serves to inject electrons to an emitting unit arranged on the side of the charge-generating layer near to an anode.

In a stacked-type organic EL device in which emitting units are stacked via charge-generating layers, it is known that the luminance [cd/A] can be ideally increased two-fold with the luminous efficiency [lm/W] being unchanged in the case where two emitting units are stacked, and the luminance [cd/A] can be ideally increased three-fold with the luminous efficiency [lm/W] being unchanged in the case where three emitting units are stacked.

For the MPE device, Patent Document 1 and 3 disclose a device in which a transparent conductor (ITO, IZO or the like) is used in a charge-generating layer, for example.

Patent Document 2 discloses a device in which vanadium oxide ($V_2O_5$) or rhenium (VII) oxide ($Re_2O_7$) is used in a charge-generating layer. Patent Document 4 discloses a device in which a metal oxide such as molybdenum oxide ($MoO_3$) or a metal salt such as ferric chloride ($FeCl_3$) is used in a charge-generating layer. Patent Document 5 discloses a device in which a combination of an N-doped layer and a P-doped layer is used in a charge-generating layer. Patent Document 6 discloses a device in which a phthalocyanine compound is used in a charge-generating layer. Patent Document 7 discloses a device in which an electron-accepting organic substance such as hexaazatriphenylene (HAT) and F4TCNQ described in Patent Document 2 is used in a charge-generating layer.

As can be seen from the above, although various materials are used in a charge-generating layer, a conventional charge-generating layer still has some problems to be solved.

Specifically, an inorganic substance such as a metal oxide requires high deposition temperatures at film-formation, thereby decreasing the efficiency of film-formation process and thus lowering mass productivity.

Moreover, since a transparent conductor such as ITO has a high electrical conductivity, current leakage may occur between pixels through a charge-generating layer. Therefore, when desired pixels are allowed to emit, adjacent pixels may emit. The phenomenon becomes a problem in a display in which an organic EL device is allowed to emit white light, and each color of RGB is outcoupled through each color filter provided on the device. That is, the color purity is remarkably lowered by color mixing due to the emission of adjacent pixels, thereby deteriorating color reproducibility.

In addition, there is a fear that when a transparent conductor is formed into a film by sputtering or the like, generated plasma particles damage an organic layer serving as a base.

On the other hand, when an organic compound is used, since the temperature of film formation is normally low and thus plasma particles are not generated, the efficiency of film formation process and the mass productivity is excellent. When an electron-accepting organic compound is used, in particular, HAT is used, as shown in Patent Document 7, a device superior in terms of properties such as efficiency, voltage, lifetime or the like can be obtained. However, HAT itself has a high conductivity, current leakage may occur between pixels through a charge-generating layer as in the case of the above-mentioned transparent conductor.

RELATED ART DOCUMENTS

Patent Documents

[Patent Document 1] JP-A-2003-45676
[Patent Document 2] JP-A-2003-272860
[Patent Document 3] JP-A-H11-329748
[Patent Document 4] JP-A-2006-24791
[Patent Document 5] JP-A-2004-39617
[Patent Document 6] JP-A-2006-73484
[Patent Document 7] JP-A-2006-173550

SUMMARY OF THE INVENTION

An object of the invention is to provide a stacked-type MPE device having a high luminous efficiency and a low driving voltage. Also, the invention is aimed at providing a stacked-type MPE device which can suppress current leakage between pixels when the device forms the pixels.

The inventors have made intensive studies to achieve the above objects. As a result, the inventors have found that, by using specific compounds in a charge-generating layer, a stacked-type MPE device having a high luminous efficiency and a low driving voltage can be obtained and current leakage between pixels can be suppressed. The invention has been made based on this finding.

According to the invention, the following organic EL device can be provided:

1. An organic electroluminescence device comprising:
   an anode;
   a cathode;
   two or more emitting units that are disposed between the anode and the cathode, each unit having an emitting layer; and
   a charge-generating layer that is disposed between the emitting units,
   wherein the charge-generating layer comprises an N layer nearer to the anode and a P layer nearer to the cathode, and
   the P layer comprises a compound represented by the following formula (I):

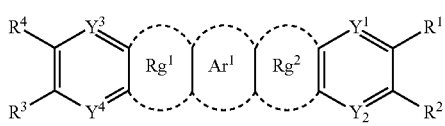
(I)

wherein in the formula (I),
Ar$^1$ is an aromatic ring including 6 to 24 carbon atoms that form a ring (hereinafter referred to as "ring carbon atoms"), or a heterocyclic ring including 5 to 24 atoms that form a ring (hereinafter referred to as "ring atoms"), and
Rg$^1$ and Rg$^2$ may be the same or different from each other and are represented by the following formula (i) or (ii):

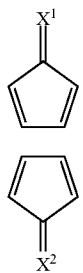

(i)

(ii)

wherein X$^1$ and X$^2$ may be the same or different from each other and are represented by any one of divalent groups represented by the following (a) to (g):

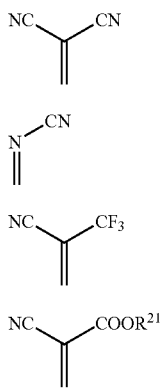

(a)

(b)

(c)

(d)

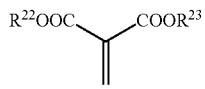
(e)

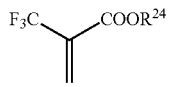
(f)

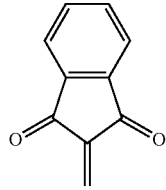
(g)

wherein R$^{21}$ to R$^{24}$ may be the same or different from each other, and are a hydrogen atom, a substituted or unsubstituted fluoroalkyl group, a substituted or unsubstituted alkyl group, a substituted or unsubstituted aryl group or a substituted or unsubstituted heterocyclic group, and R$^{22}$ and R$^{23}$ may be bonded to each other to form a ring;

R$^1$ to R$^4$ may be the same or different from each other, and a hydrogen atom, a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxy group, a substituted or unsubstituted fluoroalkoxy group, a substituted or unsubstituted aryloxy group, a substituted or unsubstituted aralkyloxy group, a substituted or unsubstituted amino group, a substituted or unsubstituted silyl group, or a cyano group;

R$^1$ and R$^2$ may be bonded to each other to form a ring and R$^3$ and R$^4$ may be bonded to each other to form a ring; and
Y$^1$ to Y$^4$ may be the same or different from each other, and are —N=, —CH=, or C(R$^5$)=, R$^5$ is the same as R$^1$ to R$^4$, and adjacent groups of R$^1$ to R$^5$ may be bonded to each other to form a ring.

2. The organic electroluminescence device according to 1, wherein the P layer comprises a compound represented by the formula (I) and at least one hole-transporting material.

3. The organic electroluminescence device according to 1 or 2, wherein at least one of the emitting units comprises a hole-transporting layer, and the P layer of the charge-generating layer is contacted with the hole-transporting layer.

4. The organic electroluminescence device according to any of 1 to 3, wherein the N layer of the charge-generating layer comprises at least one of an electron-donating metal, an electron-donating metal compound and an electron-donating metal complex.

5. The organic electroluminescence device according to 4, wherein the N layer of the charge-generating layer comprises at least one of an alkali metal, an alkali metal compound, an alkali metal-containing organic metal complex, an alkaline-earth metal, an alkaline-earth metal compound, an alkaline-earth metal-containing organic metal complex, a rare-earth metal, a rare-earth metal compound and a rare-earth metal-containing organic metal complex.

6. The organic electroluminescence device according to any of 1 to 5, wherein the N layer of the charge-generating layer comprises a nitrogen-containing heterocyclic compound.

7. The organic electroluminescence device according to 6, wherein the nitrogen-containing heterocyclic compound is represented by the following formula (9):

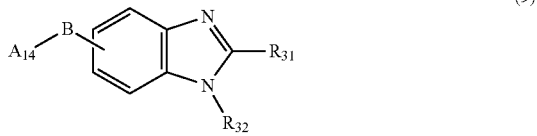

(9)

wherein, $A_{14}$ is a hydrogen atom, a halogen atom, a substituted or unsubstituted alkyl group including 1 to 20 carbon atoms, a substituted or unsubstituted hydrocarbon group including 6 to 60 carbon atoms that comprises a polycyclic aromatic hydrocarbon group formed by 3 to 40 aromatic rings being fused, or a nitrogen-containing heterocyclic group, B is a single bond, or a substituted or unsubstituted aromatic ring group, $R_{31}$ and $R_{32}$ are independently a hydrogen atom, a halogen atom, a substituted or unsubstituted alkyl group including 1 to 20 carbon atoms, a substituted or unsubstituted aromatic hydrocarbon group including 6 to 60 carbon atoms, a substituted or unsubstituted nitrogen-containing heterocyclic group, or a substituted or unsubstituted alkoxy group including 1 to 20 carbon atoms.

8. The organic electroluminescence device according to any of 1 to 7, wherein a material constituting the emitting layer(s) of at least one of the emitting units is different from a material constituting the emitting layer(s) of other emitting unit(s).

9. The organic electroluminescence device according to any of 1 to 8, which emits white light.

According to the invention, a stacked-type organic EL device having a high luminous efficiency and a low driving voltage can be provided. In addition, current leakage between pixels can be suppressed.

MODE FOR CARRYING OUT THE INVENTION

The organic EL device of the invention has a configuration in which two or more emitting units are disposed between an anode and a cathode, and a charge-generating layer is disposed between the emitting units.

Figure 1:
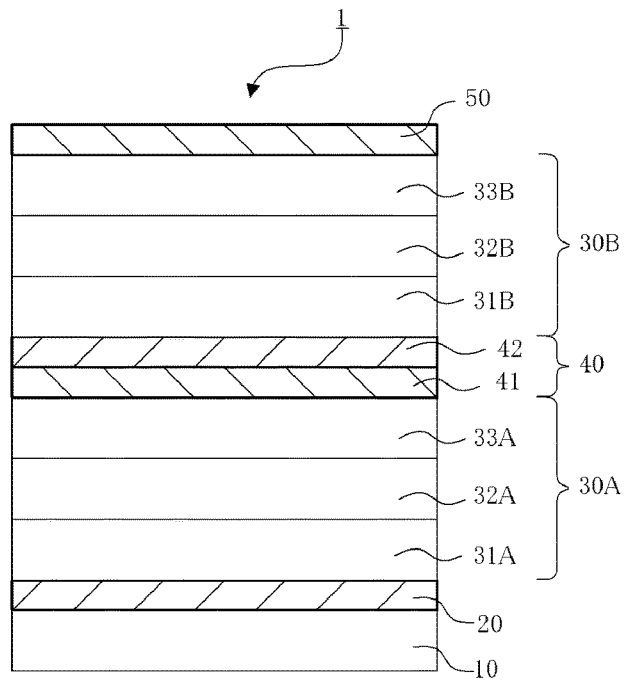
FIG. 1 is a schematic cross-sectional view showing one embodiment of the organic EL device according to the invention.

FIG. 1 is a schematic cross-sectional view showing one embodiment of the organic EL device of the invention.

An organic EL device 1 comprises, on a substrate 10, an anode 20, a first emitting unit 30A, a charge-generating layer 40, a second emitting unit 30B and a cathode 50 in this sequence.

The first emitting unit 30A and the second emitting unit 30B emit light by recombination of electrons and holes. The two emitting units respectively have a single layer structure or a stacked layer structure including at least emitting layers 32A and 32B. In this embodiment, the emitting layer has a multilayer structure in which a hole-transporting layer 31, an emitting layer 32 and an electron-transporting layer 33 are stacked from the anode side.

The charge-generating layer 40 is a layer that generates holes and electrons when a voltage is applied, and, while injecting holes to the emitting unit provided on the side of the charge-generating layer 40 near to the cathode 50 (i.e. the second emitting unit 30B), injects electrons to the emitting unit provided on the side of the charge-generating layer 40 nearer to the anode 20 (i.e. the first emitting unit 30A).

In the invention, the charge-generating layer 40 comprises an N layer 41 formed nearer to the anode and a P layer 42 formed nearer to the cathode. The P layer 42 comprises a compound represented by the following formula (I).

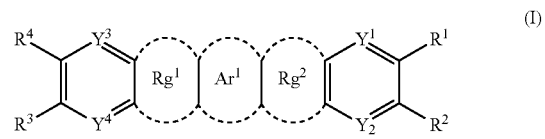

(I)

By using the compound represented by the formula (I) in the P layer, an organic EL device having a high luminous efficiency and a low driving voltage can be obtained. Further, since the charge-generating layer can be formed at a low deposition temperature, the organic EL device can have excellent film forming efficiency or mass productivity. In addition, if a plurality of organic EL devices are formed on a plane to form pixels, due to a lower conductivity than that of HAT, current leakage between adjacent pixels can be suppressed.

Hereinbelow, an explanation will be made on the compound represented by the formula (I), which is the characteristic feature of the invention.

In the above formula (I), $Ar^1$ is an aromatic ring including 6 to 24 ring carbon atoms or a heterocyclic ring including 5 to 24 ring atoms. Preferably, $Ar^1$ is an aromatic ring including 6 to 14 ring carbon atoms or a heterocyclic ring including 5 to 14 ring atoms. As the aromatic ring, a benzene ring, a naphthalene ring, a fluorene ring, a 9,9-dimethylfluorene ring, a 9,9-dioctylfluorene ring and the like can be given. As the heterocyclic ring, a pyrazine ring, a pyridine ring, a quinoxaline ring, a thiophene ring, a benzothiophene ring, a dibenzothiophene ring, a furan ring, a benzofuran ring, a dibenzofuran ring, a phenanthroline ring, a naphthyridine ring, a tetraaza-anthracene ring and the like can be given. The aromatic ring and the heterocyclic ring may be substituted by a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxy group, a substituted or unsubstituted fluoroalkoxy group, a substituted or unsubstituted aryloxy group, a substituted or unsubstituted aralkyloxy group, a substituted or unsubstituted amino group, a substituted or unsubstituted silyl group, or a cyano group, as represented by $R^1$ to $R^4$ given below.

In the invention, the "ring carbon atoms" means carbon atoms that constitute an aromatic ring, and the "ring atoms" means carbon atoms and hetero atoms that constitute a heterocyclic ring (including an aromatic ring, an unsaturated ring and an aromatic heterocyclic ring).

$R^1$ to $R^4$ may be the same or different from each other, and are a hydrogen atom, a substituted or unsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxy group, a substituted or unsubstituted fluoroalkoxy group, a substituted or unsubstituted aryloxy group, a substituted or unsubstituted aralkyloxy group, a substituted or unsubstituted amino group, a substituted or unsubstituted silyl group, or a cyano group. $R^1$ and $R^2$ may be bonded to each other to form a ring and $R^3$ and $R^4$ may be bonded to each other to form a ring.

Examples of the alkyl group include a methyl group, an ethyl group, an n-propyl group, an isopropyl group, an n-buty group, an isobutyl group, a tert-butyl group and an octyl group.

As the cycloalkyl group, a cyclopentyl group, a cyclohexyl group or the like can be given.

As the alkenyl group, a vinyl group, a propenyl group (including a regioisomer of a double bond), a butenyl group (including a regioisomer of a double bond), a pentenyl group (including a regioisomer of a double bond) or the like can be given.

As the (substituted) aryl group, a phenyl group, a biphenyl group, a naphthyl group, a fluorophenyl group, a trifluoromethylphenyl group, a (trifluoromethyl)fluorophenyl group, a trifluorophenyl group, a bis(trifluoromethyl)phenyl group, a (trifluoromethyl)difluorophenyl group, a trifluoromethoxyphenyl group, a trifluoromethoxyfluorophenyl group or the like can be given.

As the heterocyclic group, residues of pyridine, pyrazine, furan, imidazole, benzimidazole, thiophene or the like can be given.

As the halogen atom, a fluorine atom, a chlorine atom, a bromine atom or an iodine atom can be mentioned.

As the fluoroalkyl group, a trifluoromethyl group, a pentafluoroethyl group, a perfluorocyclohexyl group, a perfluoroadamantyl group or the like can be mentioned.

As the alkoxy group, a methoxy group, an ethoxy group or the like can be mentioned.

As the fluoroalkoxy group, a trifluoromethoxy group, a pentafluoroethoxy group, a 2,2,2-trifluoroethoxy group, a 2,2,3,3,3-pentafluoropropoxy group, a 2,2,3,3-tetrafluoropropoxy group, a 1,1,1,3,3,3-hexafluoropropane-2-yloxy group or the like can be mentioned.

As the (substituted) aryloxy group, a phenyloxy group, a pentafluorophenyloxy group, a 4-trifluorophenyloxy group or the like can be mentioned.

As the (substituted) aralkyloxy group, a benzyloxy group, a pentafluorobenzyloxy group, a 4-trifluoromethylbenzyloxy group or the like can be mentioned.

As the (substituted) amino group, an amino group, a mono- or dimethylamino group, a mono- or diphenylamino group or the like can be mentioned.

As the (substituted) silyl group, a silyl group, a mono-, di- or trimethylsilyl group, a mono-, di- or triethylsilyl group, a mono-, di- or triphenylsilyl group or the like can be mentioned.

As the examples of the arbitral substituent of $R^1$ to $R^4$, the halogen atom, the cyano group, the alkyl group, the aryl group, the fluoroalkyl group, the fluoroalkoxy group and the heterocyclic group mentioned above can be given.

In the present application, unless otherwise specified, as the examples of the arbitral substituent when referring to the "substituted or unsubstituted", the halogen atom, the cyano group, the alkyl group, the aryl group, the fluoroalkly group, the fluoroalkoxy group and the heterocyclic group given above can be mentioned.

In the present application, a hydrogen atom includes an isomer differing in the number of neutrons; i.e. protium, deuterium and tritium.

As mentioned above, $R^1$ and $R^2$ may be bonded with each other to form a ring and $R^3$ and $R^4$ may be bonded with each other to form a ring. As examples of the ring, a benzene ring, a naphthalene ring, a pyrazine ring, a pyridine ring, a furan ring or the like can be given.

At least one of $R^1$ to $R^4$ is preferably an aryl group or a heterocyclic group having a fluorine atom, a fluoroalkyl group, a fluoroalkoxy group, a cyano group or at least one selected from fluorine, a fluoroalkyl group, a fluoroalkoxy group and a cyano group. By having these groups as a substituent, electron acceptability can be enhanced, an appropriate sublimation temperature can be obtained or crystallization can be suppressed.

The $Rg^1$ and the $Rg^2$ in the formula (I) may be the same or different and are represented by the following formula (i) or (ii).

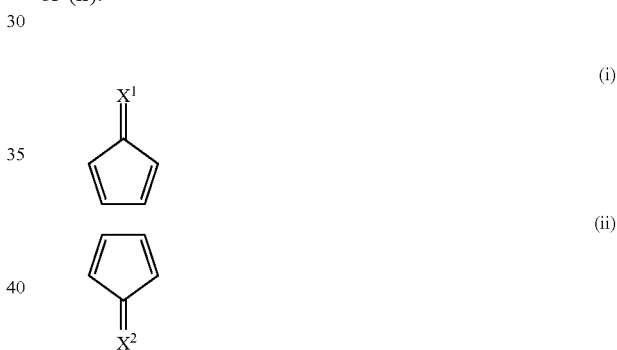

In the above formula, $X^1$ and $X^2$ may be the same or different from each other and are any of divalent groups represented by the following (a) to (g). Divalent groups represented by (a), (b) or (c) are preferable in respect of excellent heat resistance, easiness in synthesis or the like.

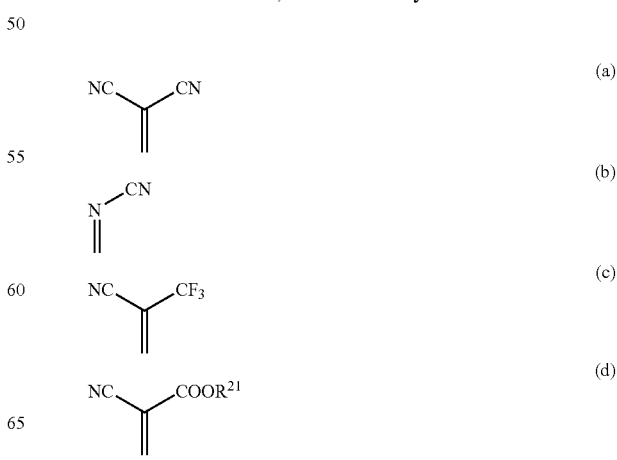

-continued (e)
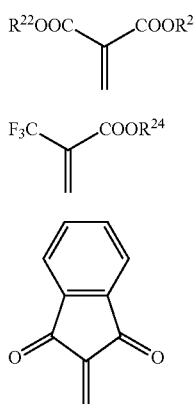

(f)

(g)

$R^{21}$ to $R^{24}$ in the above formula may be the same or different from each other, and are a hydrogen atom, a substituted or unsubstituted fluoroalkyl group, a substituted or unsubstituted alkyl group, a substituted or unsubstituted cycloalkyl group, a substituted or unsubstituted aryl group, a substituted or unsubstituted heterocyclic group, and $R^{22}$ and $R^{23}$ may be bonded to each other to form a ring. As specific examples of the fluoroalkyl group, the alkyl group, the cycloalkyl group, the aryl group and the heterocyclic group, the groups mentioned above referring to $R^1$ to $R^4$ can be given.

$Y^1$ to $Y^4$ in the formula (I) may be the same or different from each other, and are —N=, —CH=, or $C(R^5)=$, wherein $R^5$ is the same as $R^1$ to $R^4$, and adjacent groups of $R^1$ to $R^5$ may be bonded to each other to form a ring.

It is preferred that at least one of $Y^1$ to $Y^4$ be a nitrogen atom (the same applies to $Y^{21}$ to $Y^{26}$ and $Y^{31}$ to $Y^{38}$ mentioned later). If at least one of $Y^1$ to $Y^4$ is a nitrogen atom, electron acceptability can be enhanced, heat resistance can be increased or crystallization can be suppressed.

The indenofluorenedione derivative of the formula (I) is preferably represented by the following formula (I-A) or (I-B). Symbols such as $Ar^1$ in the following formula (I-A) have the same meanings as those in the formula (I). $Ar^2$ in the following formula (I-B) is the same as $Ar^1$ in the formula (I). $X^3$ and $X^4$ are the same as $X^1$ and $X^2$ in the formula (I). $Y^5$ to $Y^8$ are the same as $Y^1$ to $Y^4$ in the formula (I). $R^1$ to $R^4$ are the same as $R^1$ to $R^4$ in the formula (I).

(I-A)
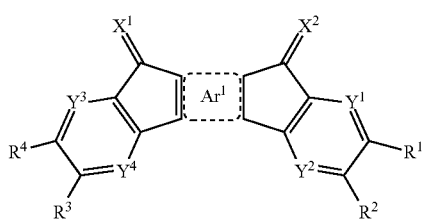

(I-B)
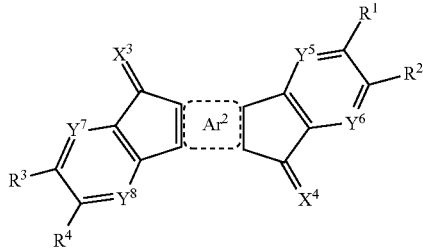

It is further preferred that the indenofluorenedione derivative in the formula (I) be represented by the following formulas (II) to (X).

(II)
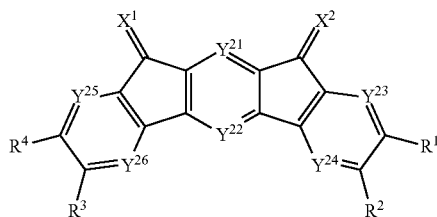

(III)
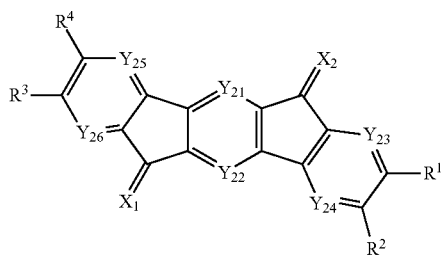

(IV)
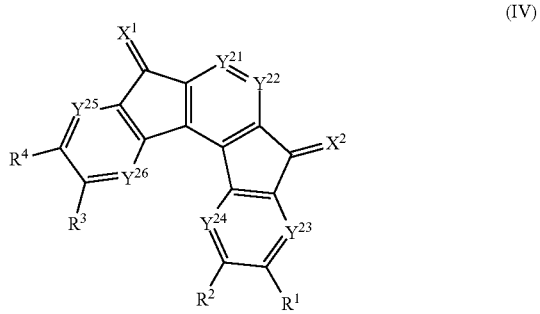

(V)
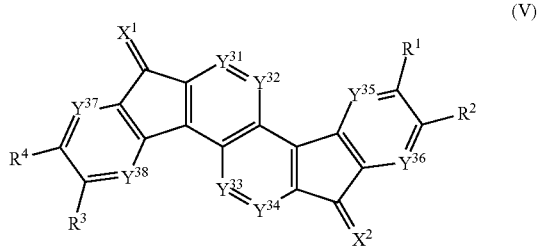

(VI)
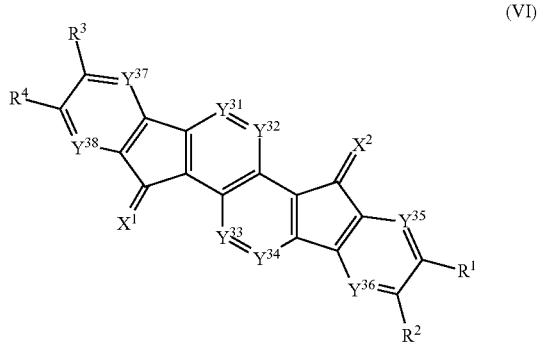

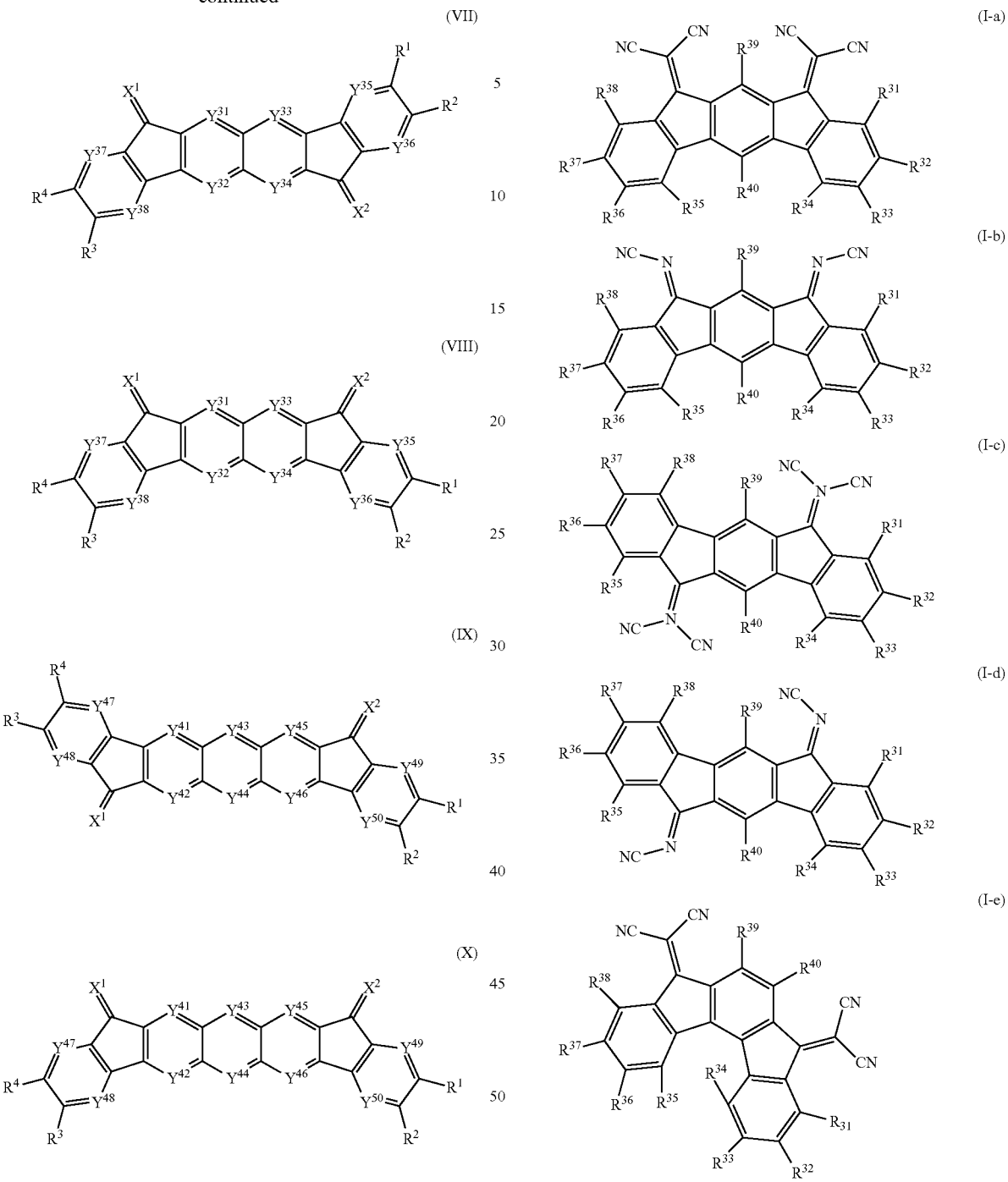

In the above formula, $X^1$ and $X^2$ and $R^1$ to $R^4$ are the same as $X^1$ and $X^2$ and $R^1$ to $R^4$ in the formula (I) and $Y^{21}$ to $Y^{26}$, $Y^{31}$ to $Y^{38}$ and $Y^{41}$ to $Y^{50}$ are the same as $Y^1$ to $Y^4$ in the formula (I).

Particularly preferable indenofluorenedione derivatives represented by the formula (I) are represented by the following formulas (I-a) to (I-n). As for the following formula (I-b), (I-d), (I-f), (I-h), (I-j), (I-l), (I-n), (I-p) and (I-r), a plurality of isomers are present due to the steric configuration of the cyano groups of the two cyanoimino groups. The invention is not limited to specific isomers. The derivative of the invention may be a specific isomer alone or may be a mixture of two or larger than two isomers.

-continued
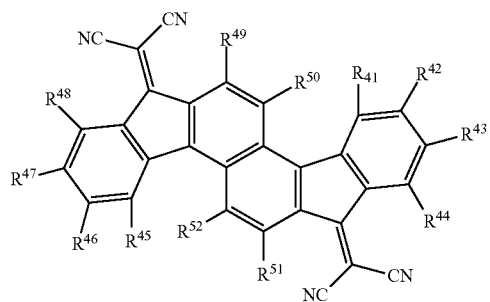
(I-g)
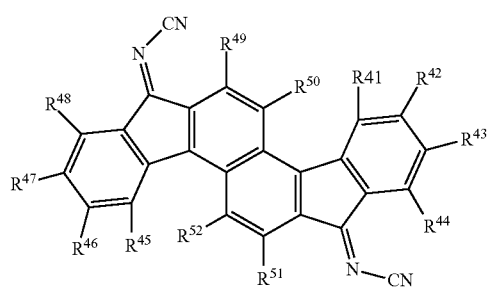
(I-h)
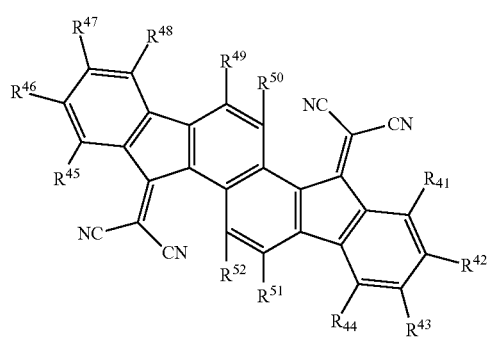
(I-i)
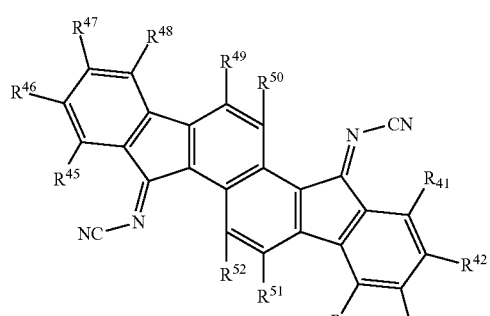
(I-j)
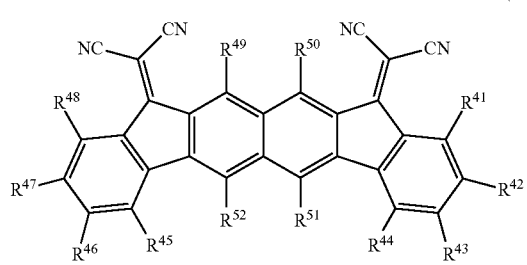
(I-k)
-continued
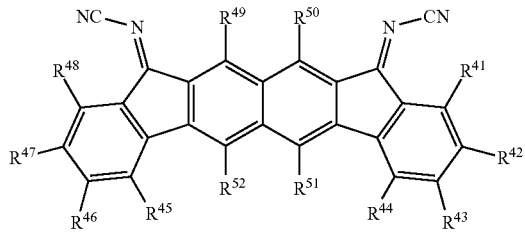
(I-l)
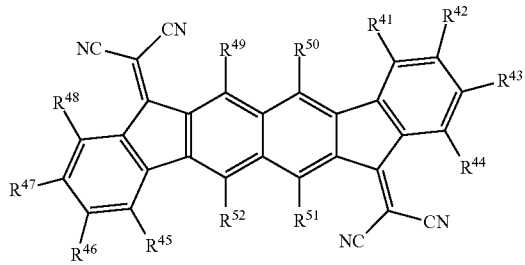
(I-m)
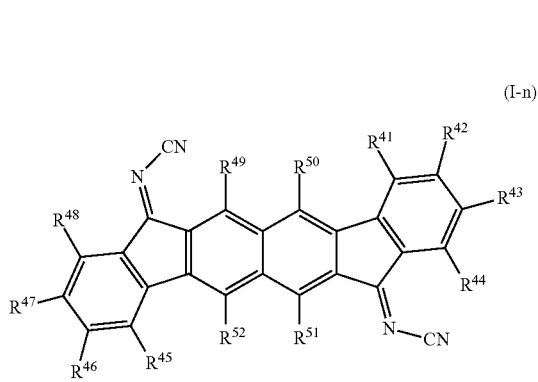
(I-n)
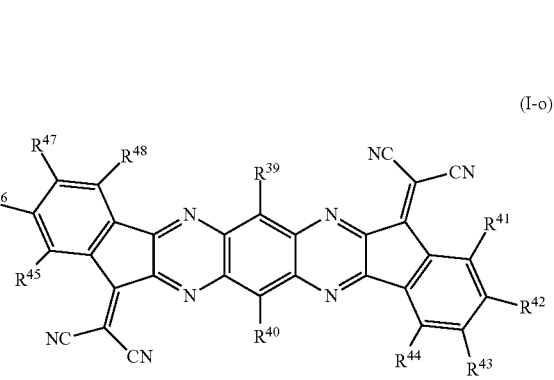
(I-o)
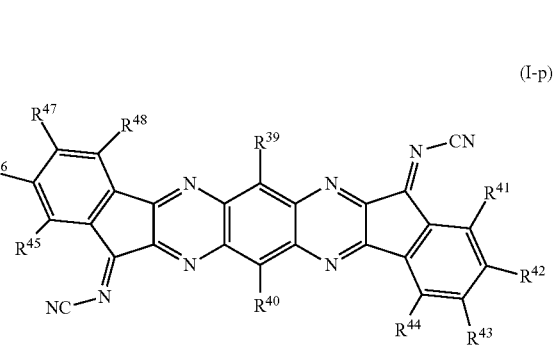
(I-p)

-continued (I-q)

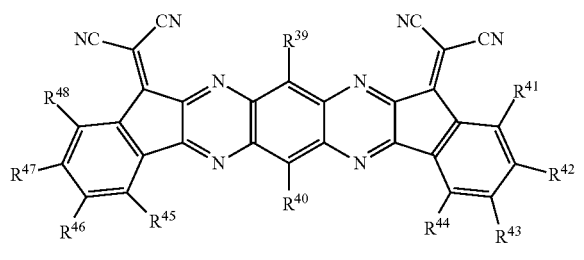

(I-r)

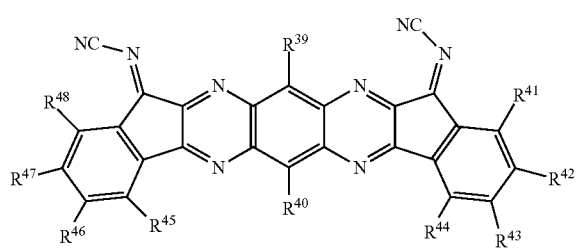

In the above formulas, $R^{31}$ to $R^{52}$ have the same meanings as $R^1$ to $R^4$ in the formula (I). Adjacent two of $R^{31}$ to $R^{52}$ may be bonded to each other to form a ring. In particular, it is preferred that at least one of $R^{31}$ to $R^{52}$ be a fluorine atom, a fluoroalkyl group, a fluoroalkoxy group, a cyano group or an aryl group or a heteroaryl group having at least one selected from fluorine, a fluoroalkyl group, a fluoroalkoxy group and a cyano group.

Due to the structure represented by each of the above-mentioned formulas, the indenofluorenedione derivative has electron acceptability. Further, since it has excellent heat resistance and a sublimation temperature of about 200° C. or more, the indenofluorenedione derivative is capable of being purified by sublimation, whereby it can have high purity. Further, by using in an organic EL device, the driving voltage of the device can be lowered, and the life thereof can be prolonged. Further, since the sublimation temperature is as high as about 200° C. or more, the derivative does not scatter to the inside of the deposition apparatus at the time of producing a device. Accordingly, there is no fear that the derivative contaminates a film-forming apparatus or an organic EL device.

Specific examples of the indenofluorenedione derivative represented by the formula (I) are given below. The invention is, however, not limited to these specific examples.

(A-1)

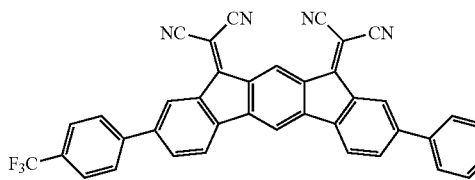

(A-2)

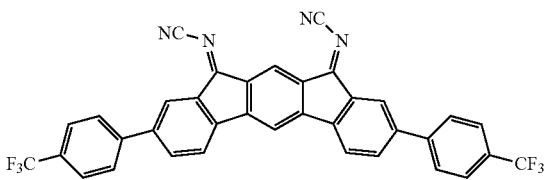

(A-3)

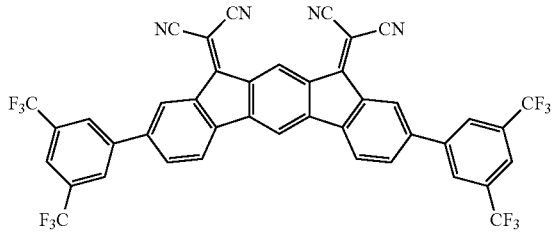

(A-4)

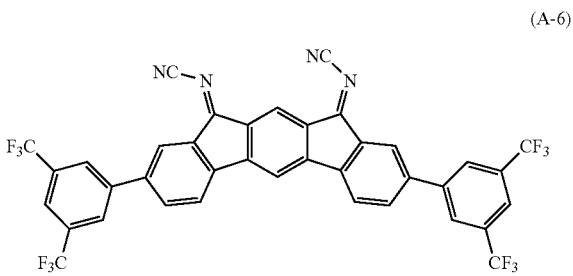

(A-5)

(A-6)

(A-7)

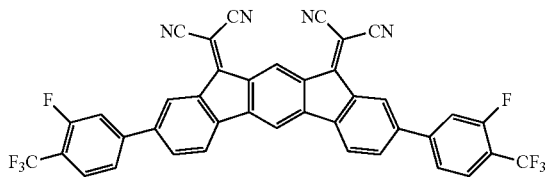

(A-8)

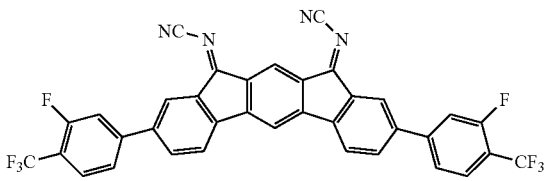

-continued
(A-9)
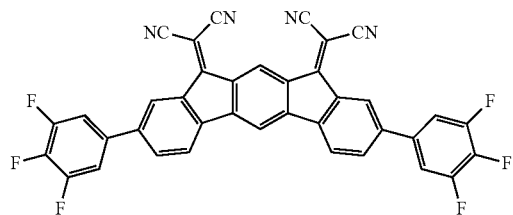
(A-10)
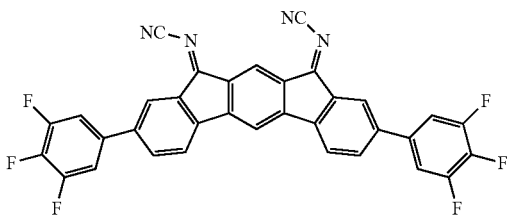
(A-11)
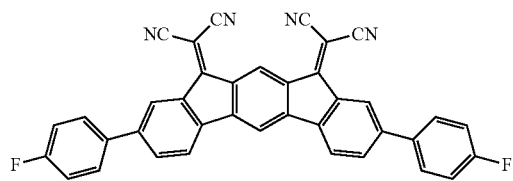
(A-12)
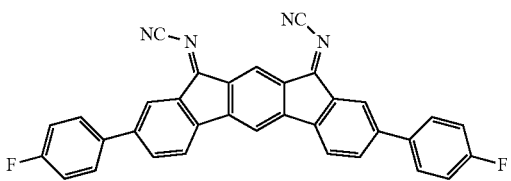
(A-13)
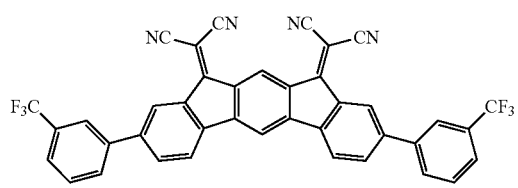
(A-14)
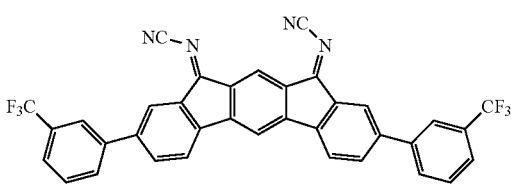
(A-15)
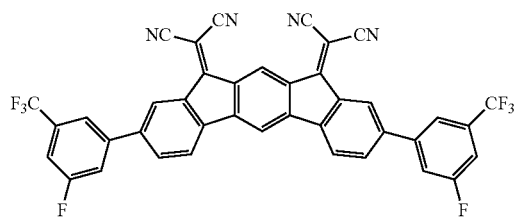
(A-16)
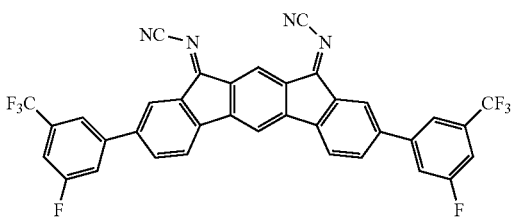
(A-17)
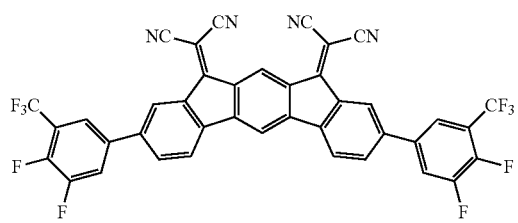
(A-18)
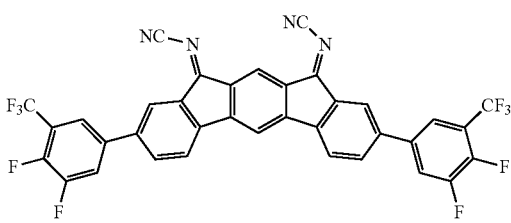
(A-19)
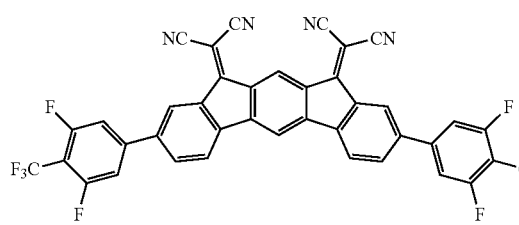
(A-20)
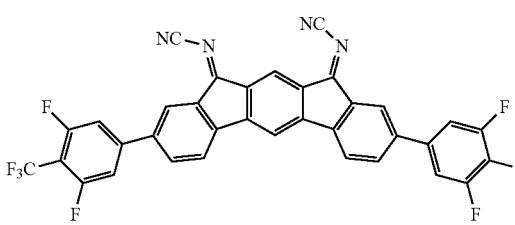
(A-21)
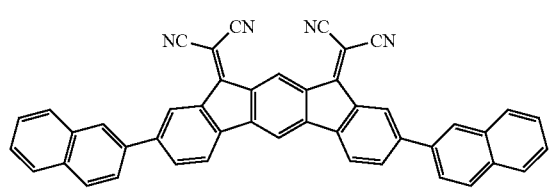
(A-22)
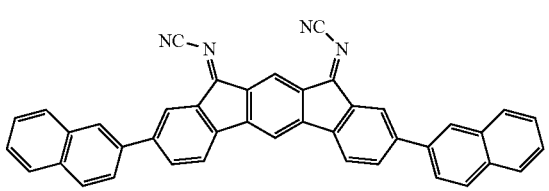

-continued
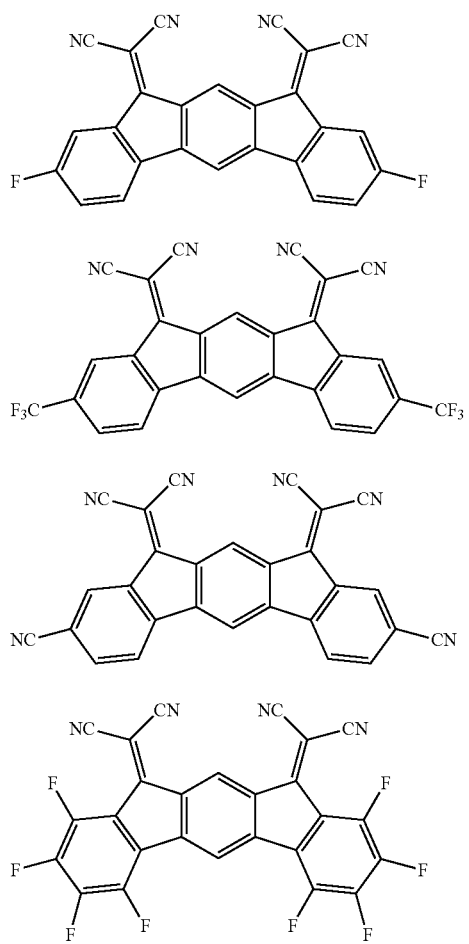
(A-23)
(A-25)
(A-27)
(A-29)
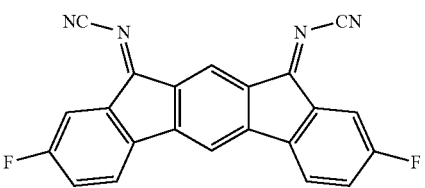
(A-24)
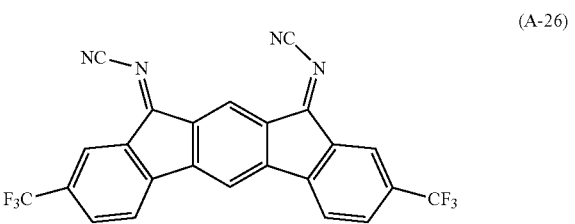
(A-26)
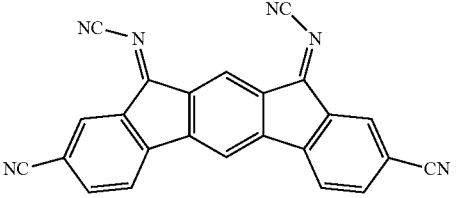
(A-28)
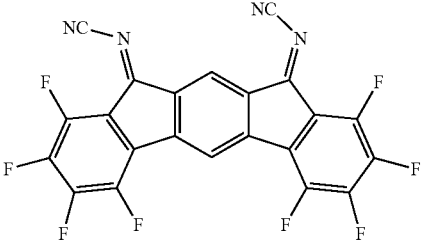
(A-30)
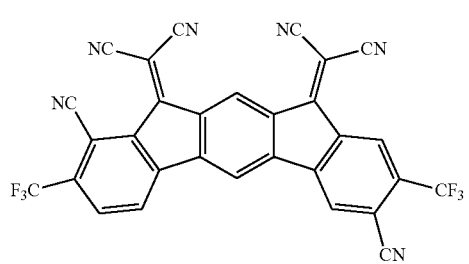
(A-31)
(A-32)
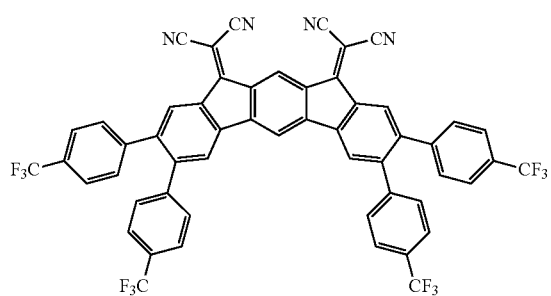
(A-33)
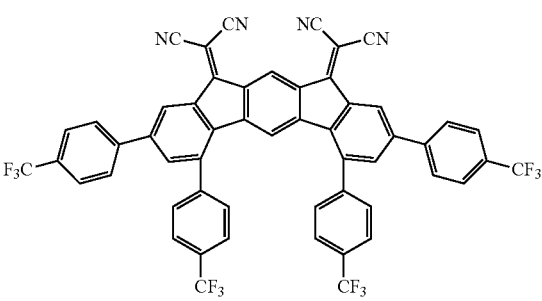
(A-34)

-continued
(A-35)
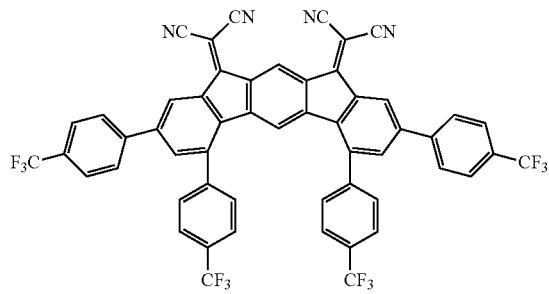
(A-36)
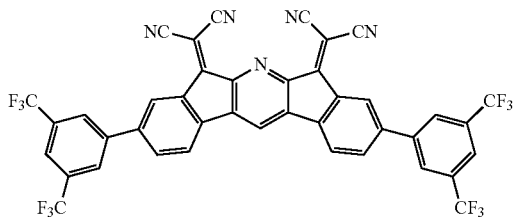
(A-37)
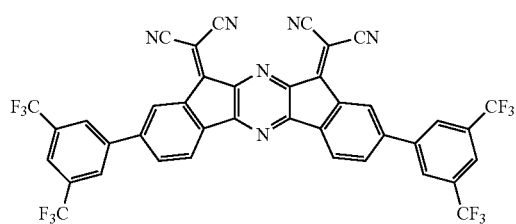
(A-38)
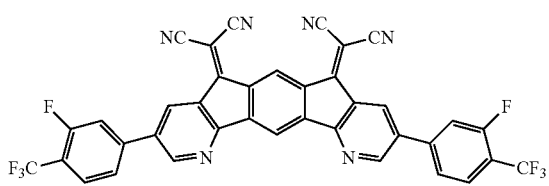
(A-39)
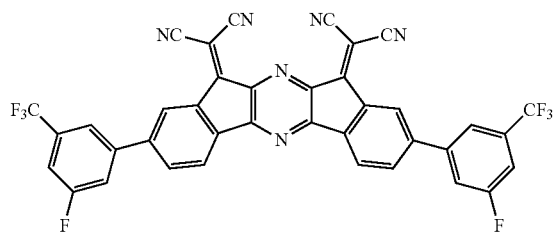
(A-40)
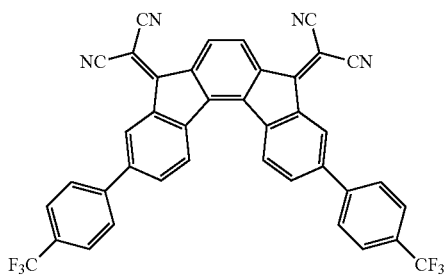
(A-41)
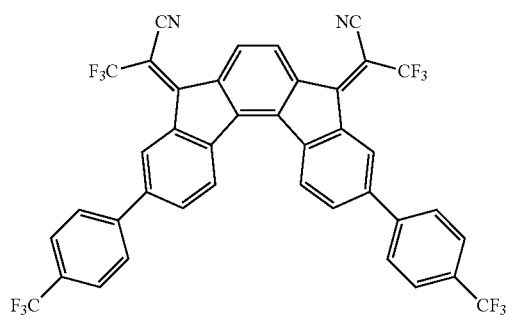
(A-42)
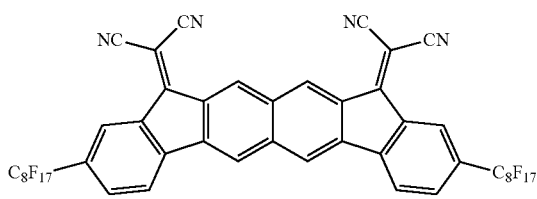
(A-43)
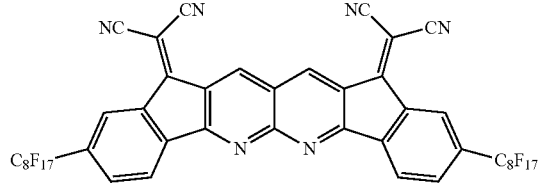
(A-44)
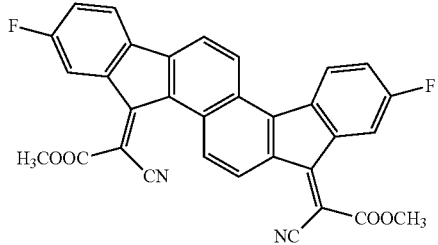

-continued
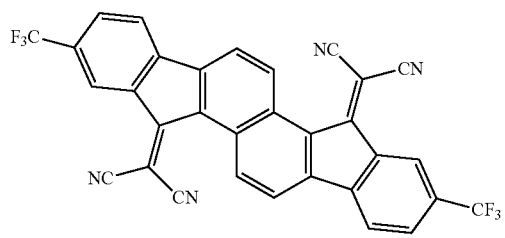
(A-45)
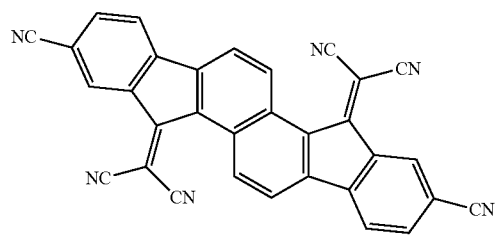
(A-46)
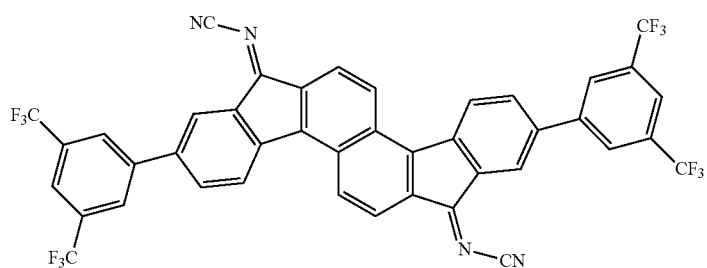
(A-47)
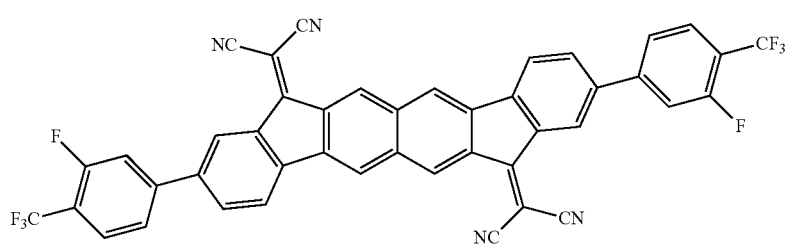
(A-48)
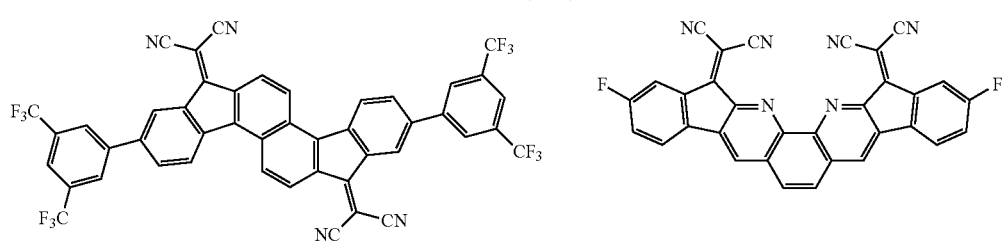
(A-49)
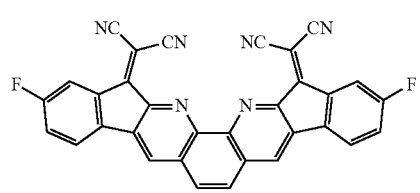
(A-50)
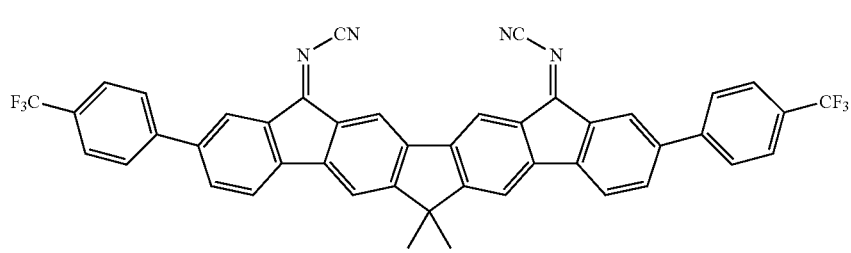
(A-51)
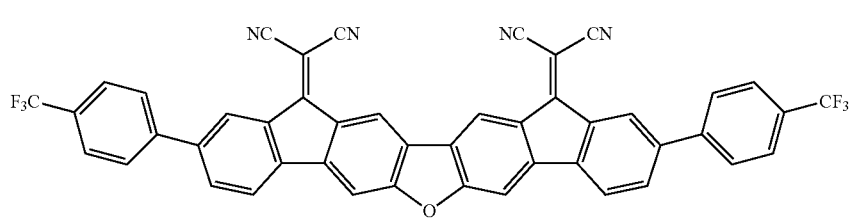
(A-52)

-continued
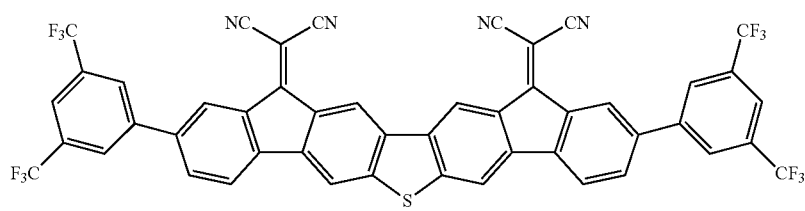
(A-53)
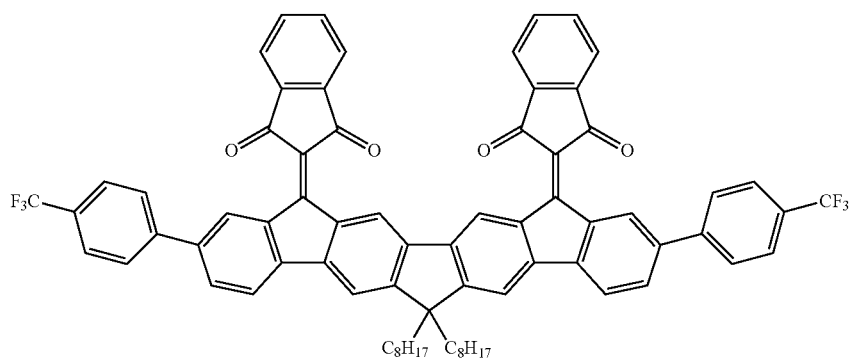
(A-54)
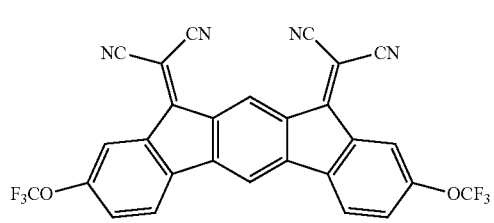
(A-55)
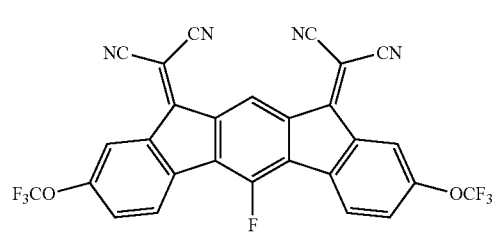
(A-56)
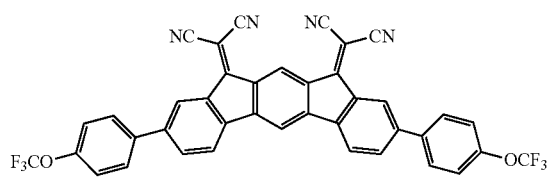
(A-57)
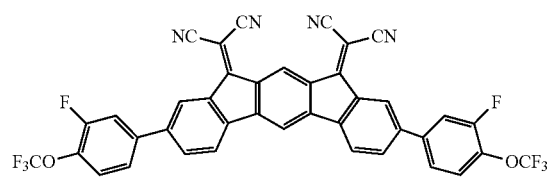
(A-58)
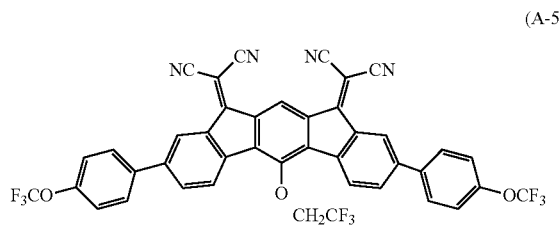
(A-59)
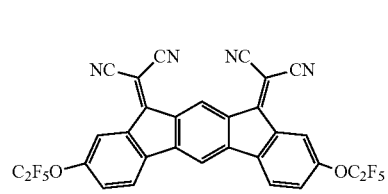
(A-60)
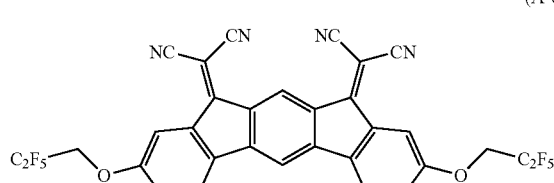
(A-61)
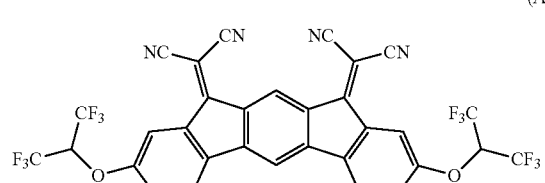
(A-62)

-continued
(A-63)
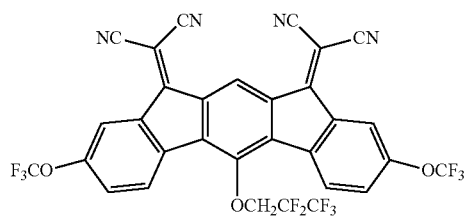
(A-64)
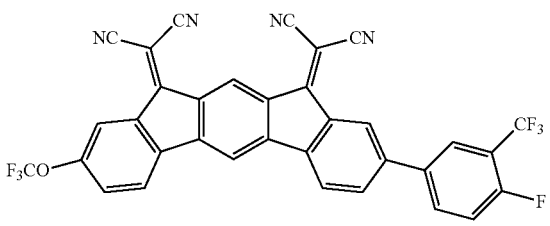
(A-65)
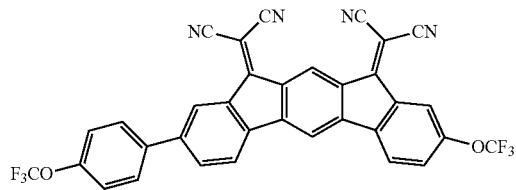
(A-66)
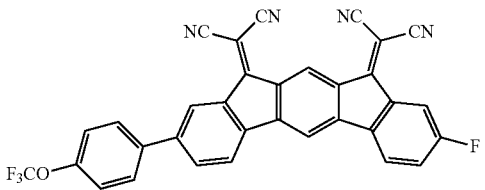
(A-67)
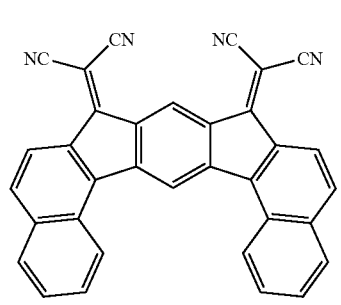
(A-68)
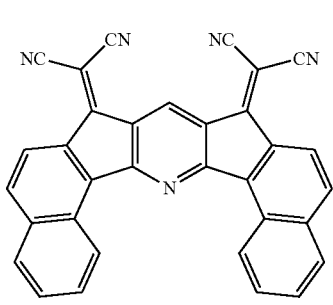
(A-69)
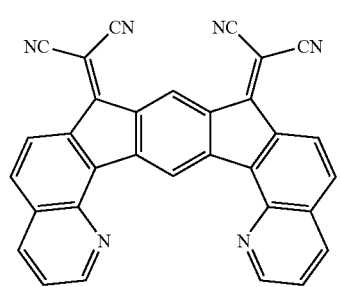
(A-70)
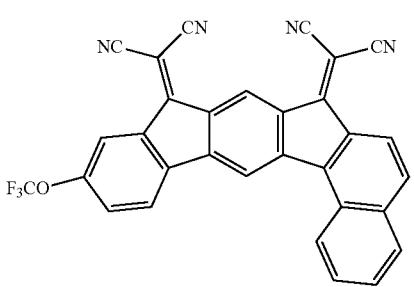
(A-71)
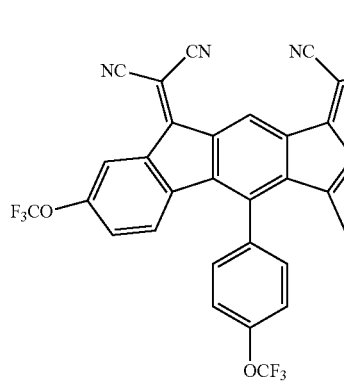
(A-72)
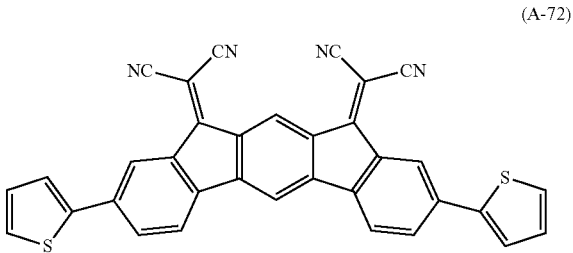
(A-73)
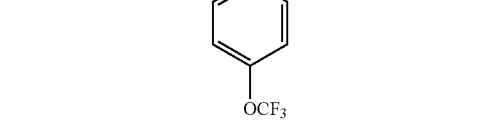
(A-74)
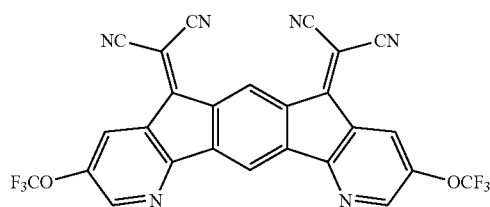

-continued
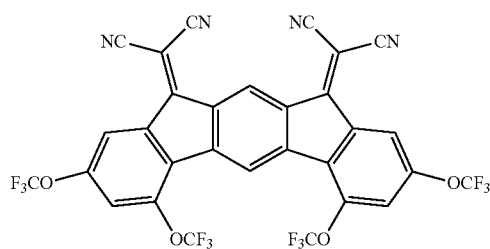
(A-75)
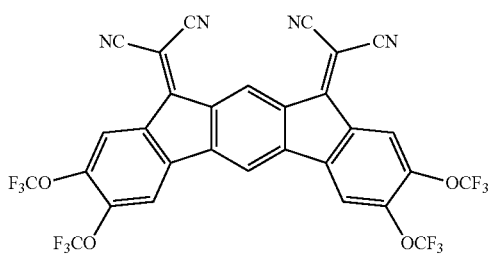
(A-76)
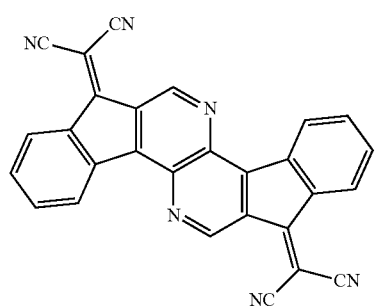
(A-77)
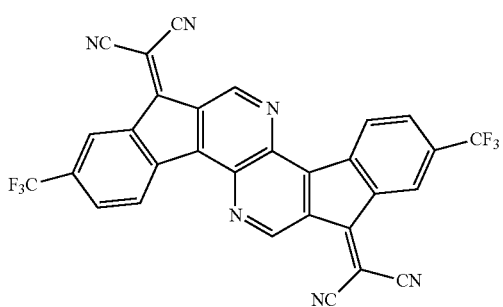
(A-78)
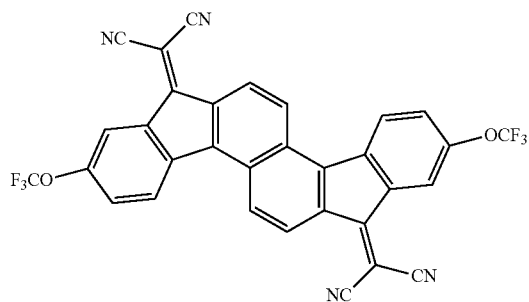
(A-79)
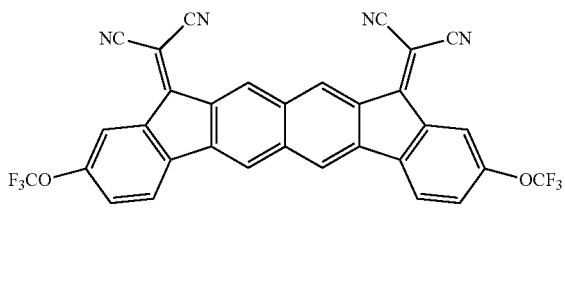
(A-80)
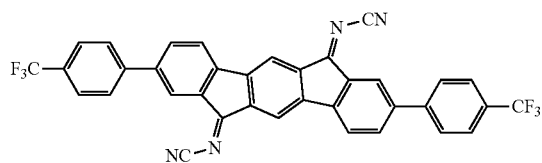
(A-81)
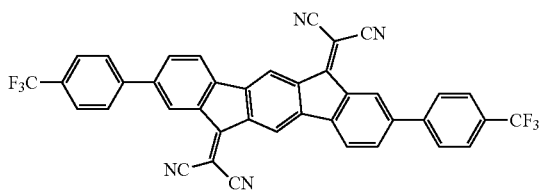
(A-82)
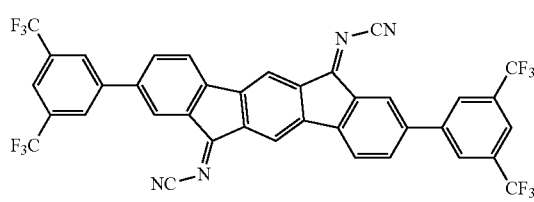
(A-83)
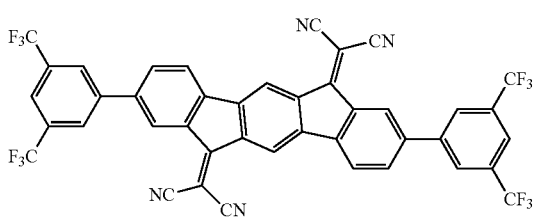
(A-84)
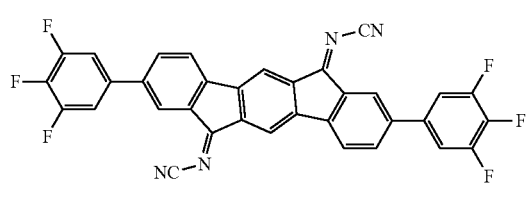
(A-85)
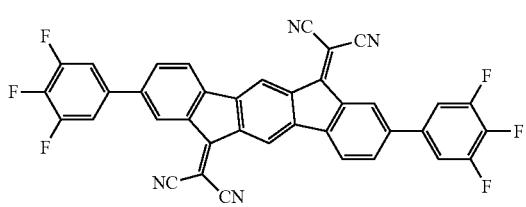
(A-86)

-continued
(A-87)
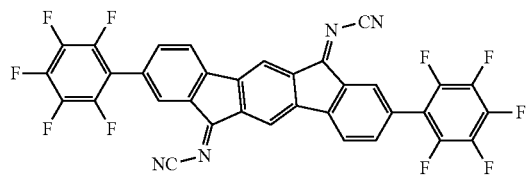
(A-88)
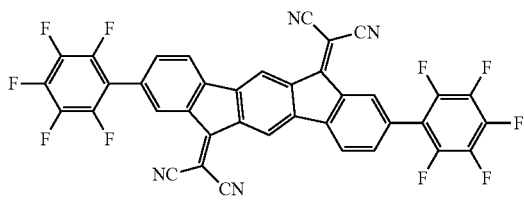
(A-89)
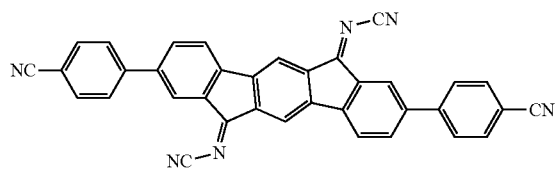
(A-90)
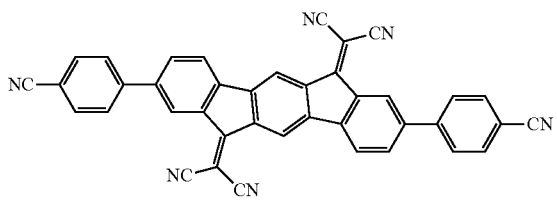
(A-91)
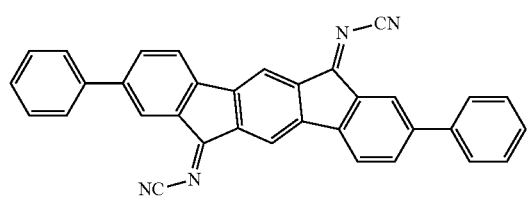
(A-92)
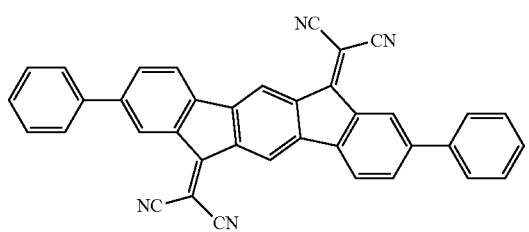
(A-93)
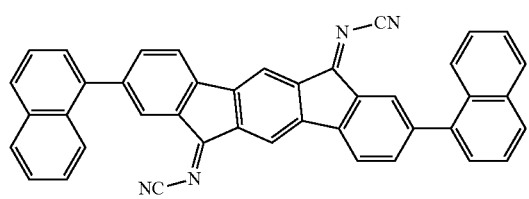
(A-94)
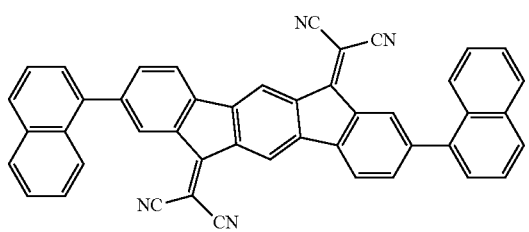
(A-95)
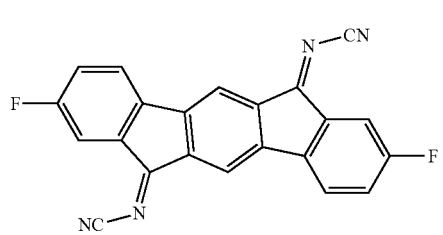
(A-96)
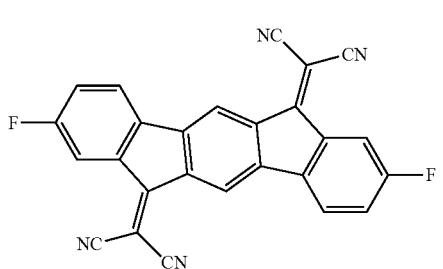
(A-97)
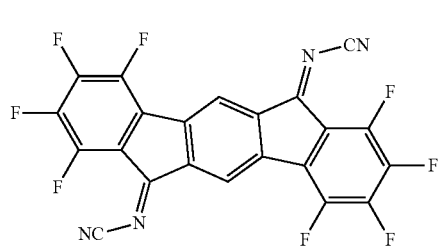
(A-98)
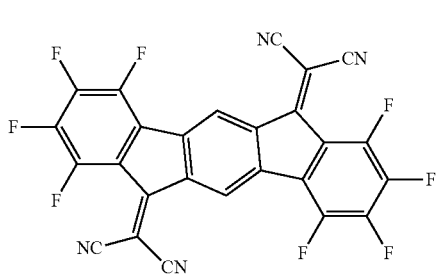

-continued
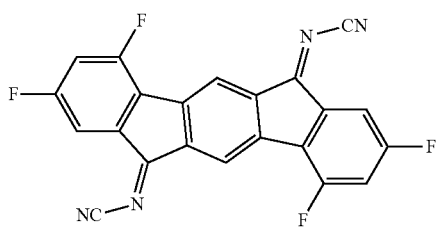
(A-99)
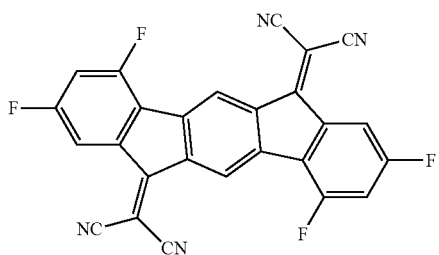
(A-100)
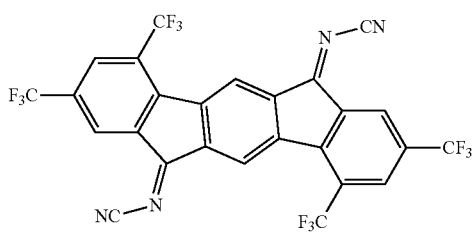
(A-101)
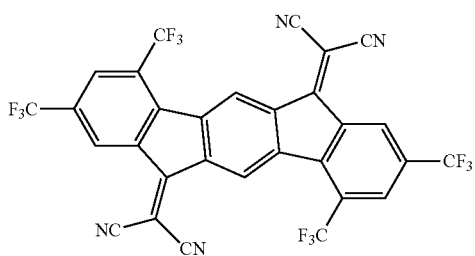
(A-102)
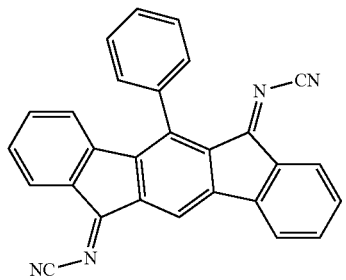
(A-103)
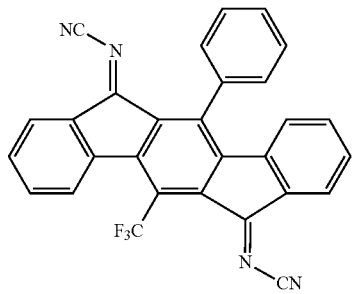
(A-104)
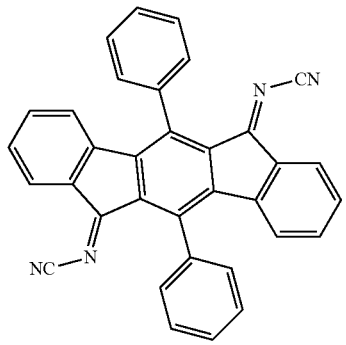
(A-105)
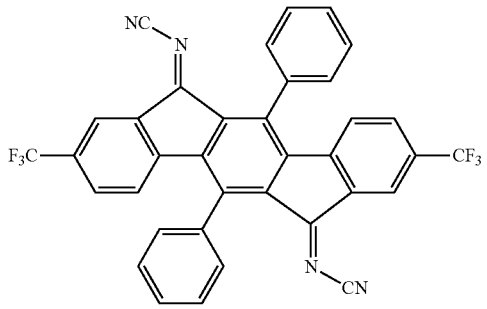
(A-106)
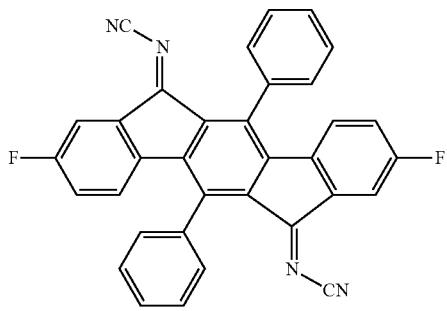
(A-107)
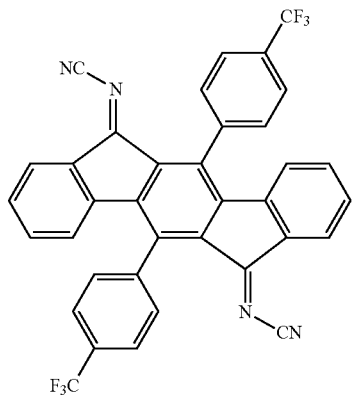
(A-108)

-continued
(A-109) 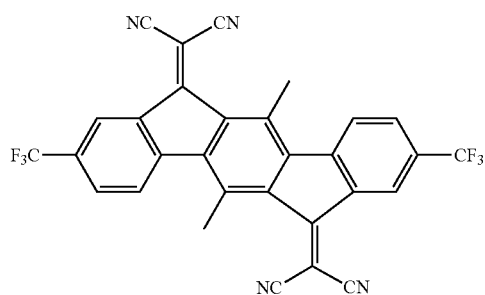
(A-110) 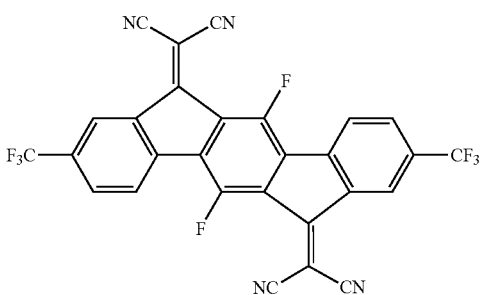
(A-111) 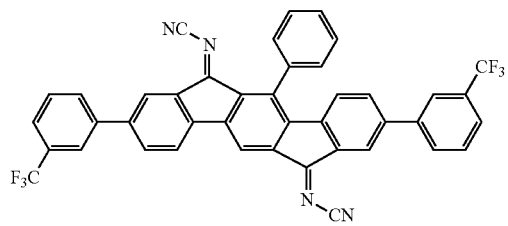
(A-112) 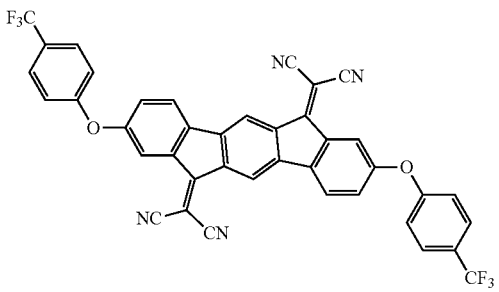
(A-113) 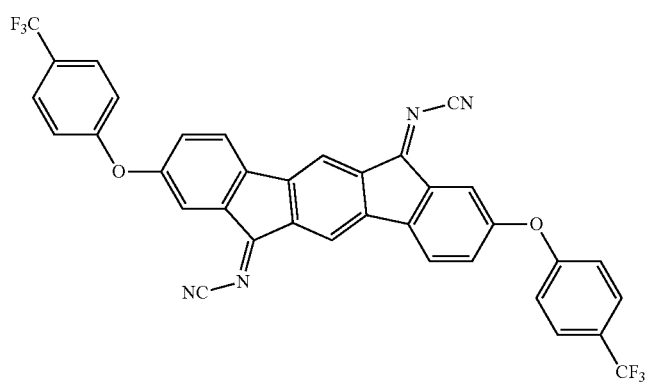
(A-114) 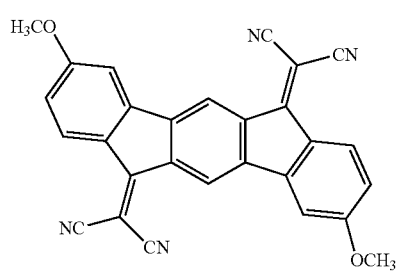
(A-115) 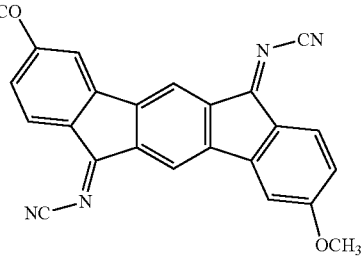
(A-116) 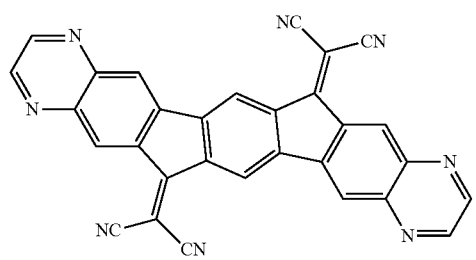
(A-117) 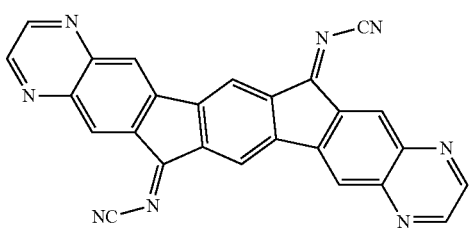

-continued
(A-118)
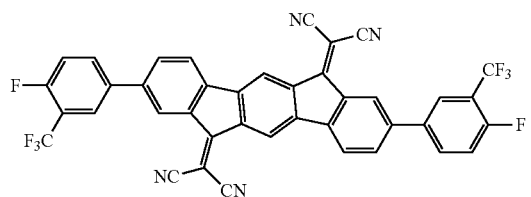
(A-119)
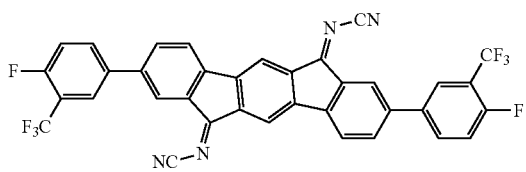
(A-120)
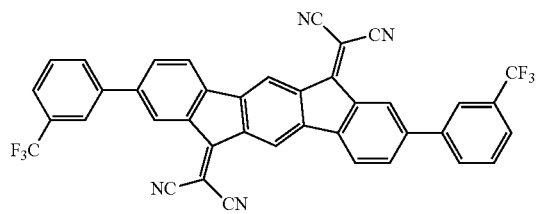
(A-121)
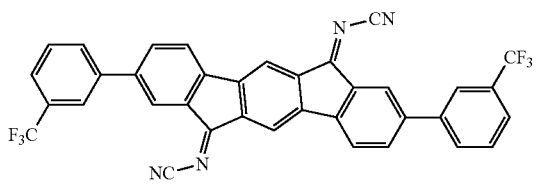
(A-122)
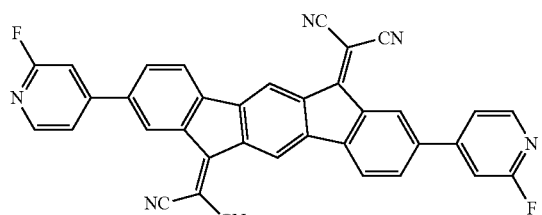
(A-123)
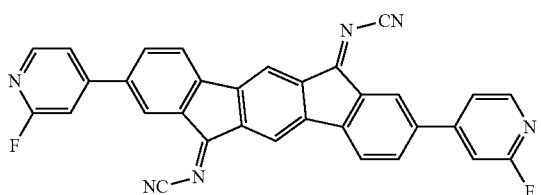
(A-124)
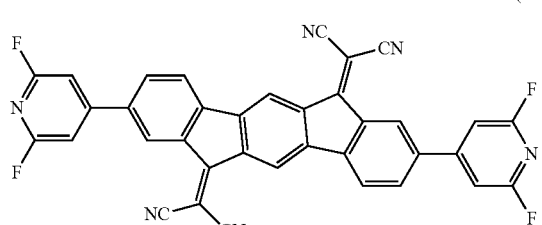
(A-125)
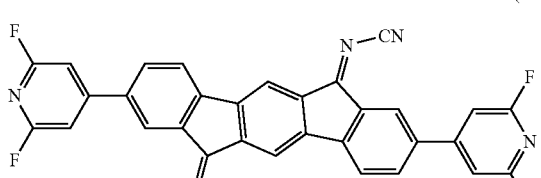
(A-126)
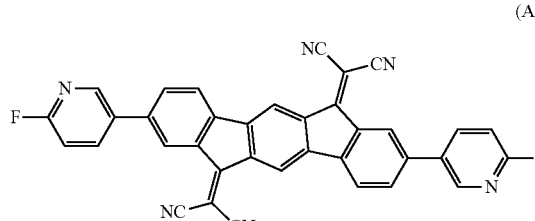
(A-127)
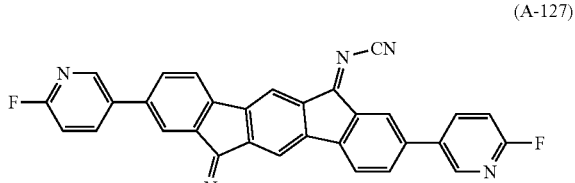
(A-128)
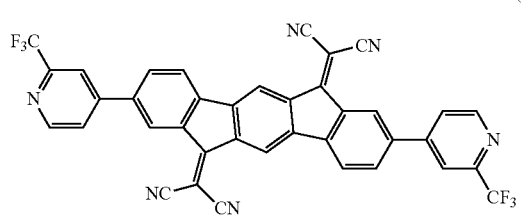
(A-129)
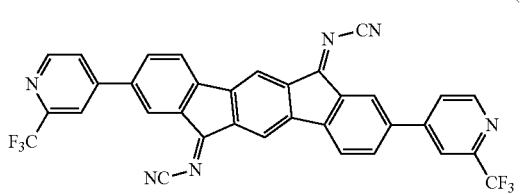
(A-130)
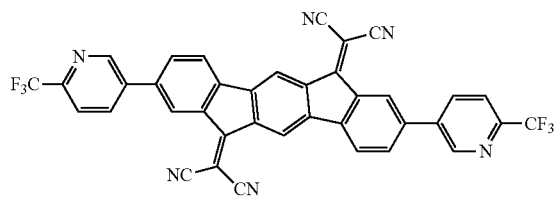
(A-131)
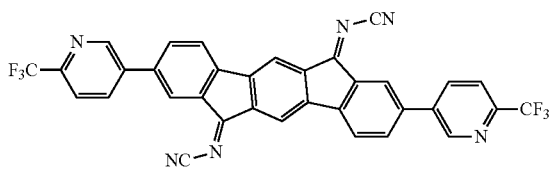

-continued
(A-132)
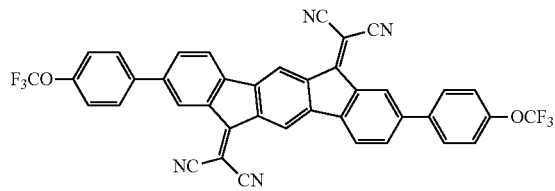
(A-133)
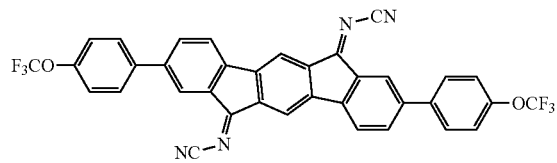
(A-134)
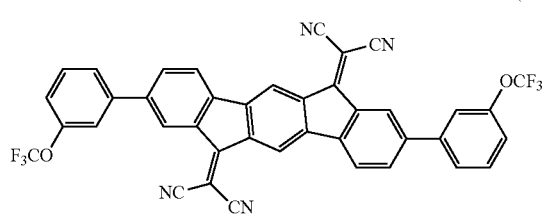
(A-135)
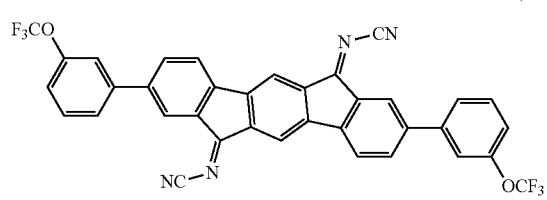
(A-136)
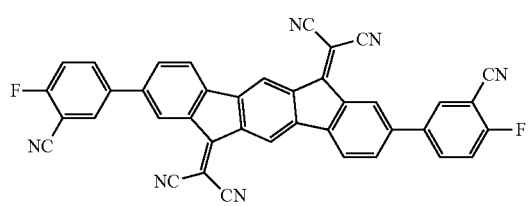
(A-137)
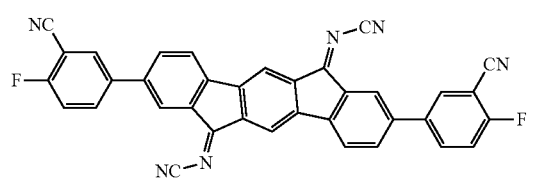
(A-138)
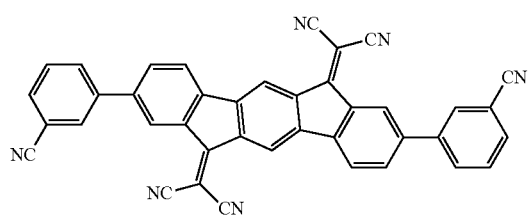
(A-139)
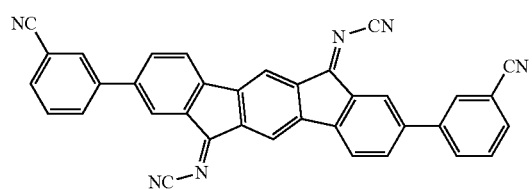
(A-140)
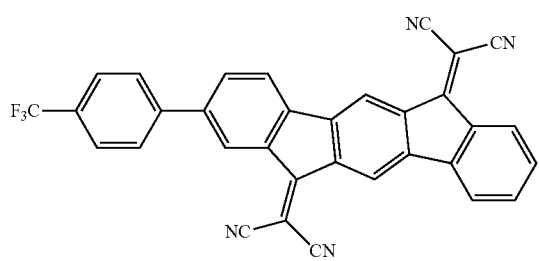
(A-141)
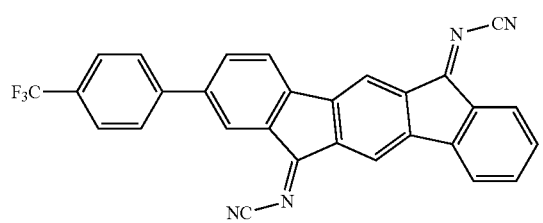
(A-142)
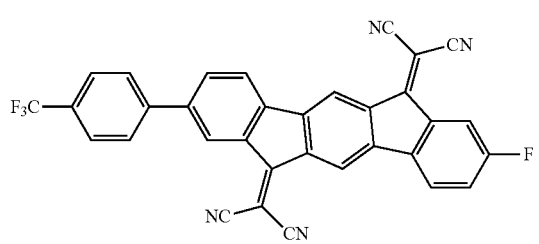
(A-143)
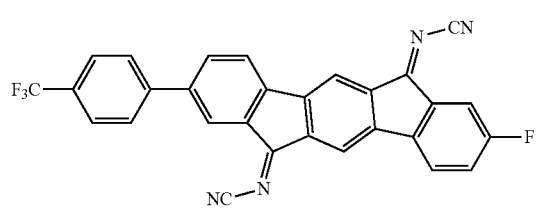

-continued
(A-144)
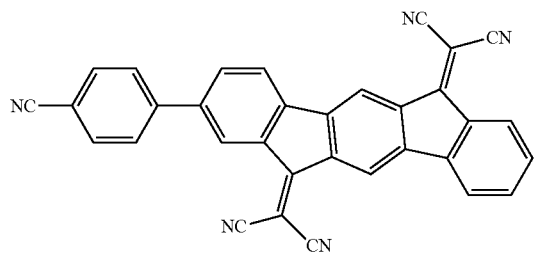
(A-145)
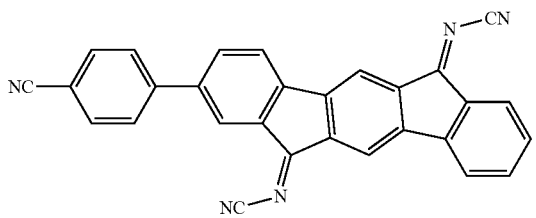
(A-146)
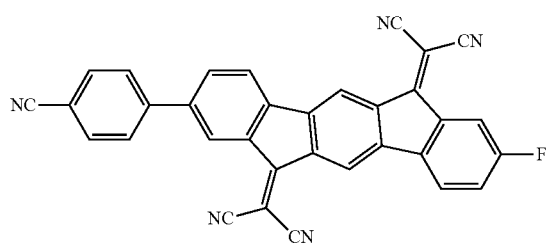
(A-147)
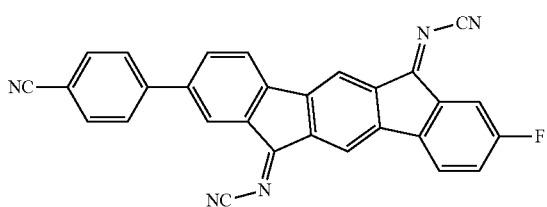
(A-148)
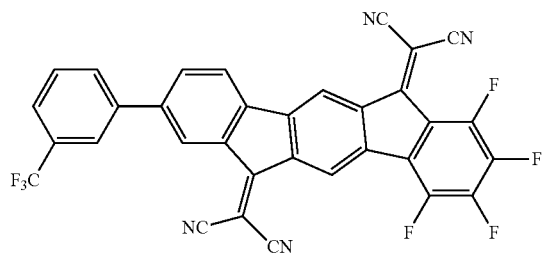
(A-149)
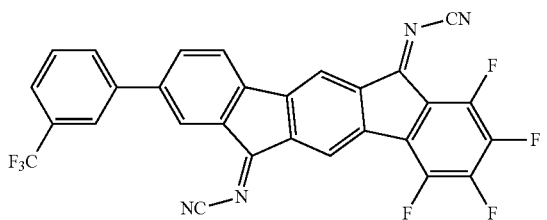
(A-150)
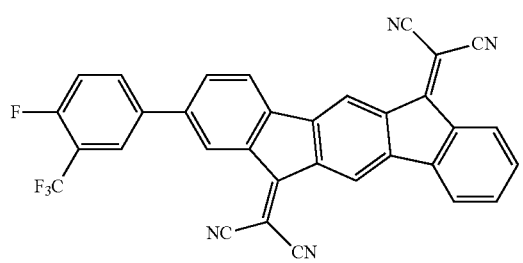
(A-151)
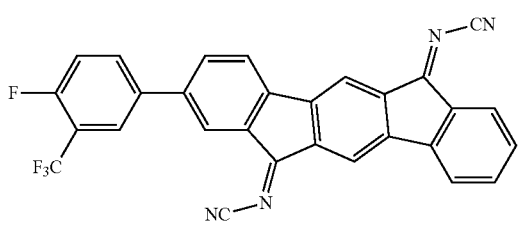
(A-152)
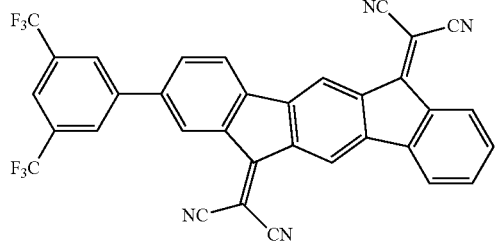
(A-153)
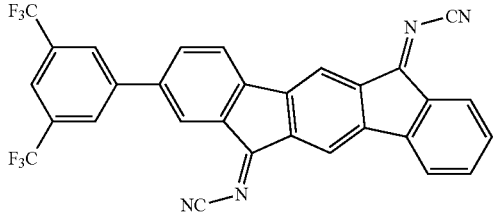
(A-154)
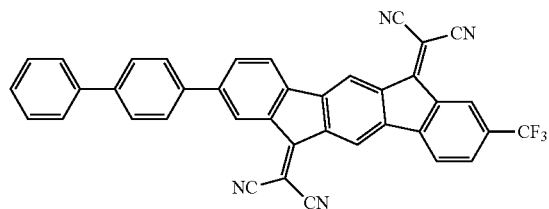
(A-155)
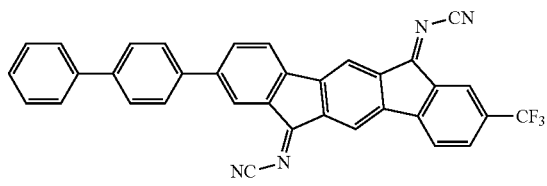

-continued
(A-156)
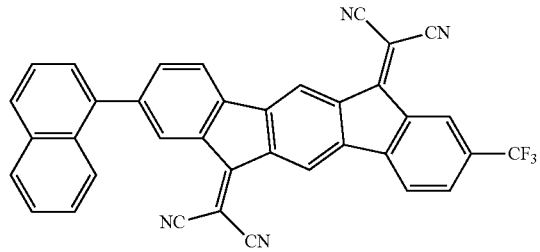
(A-157)
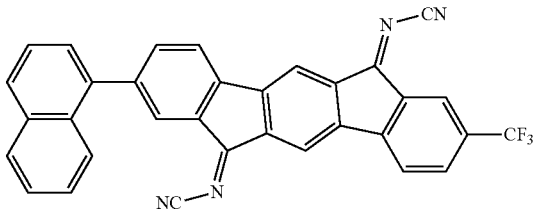
(A-158)
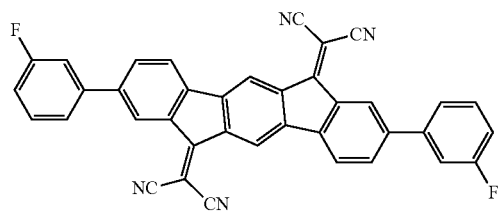
(A-159)
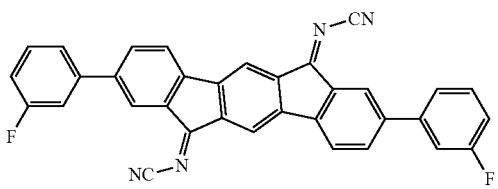
(A-160)
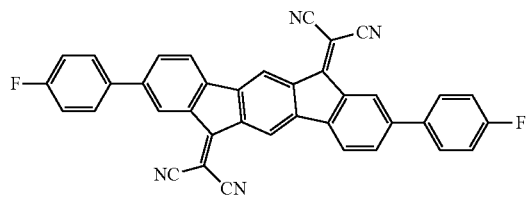
(A-161)
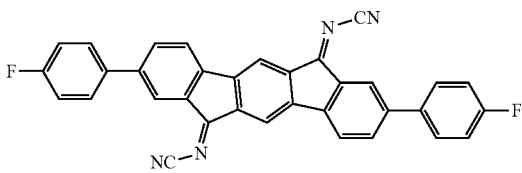
(A-162)
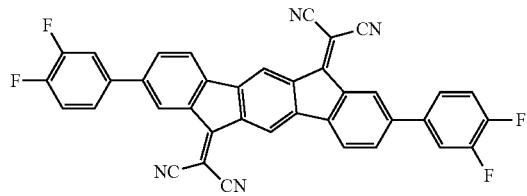
(A-163)
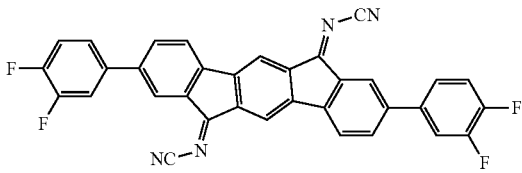
(A-164)
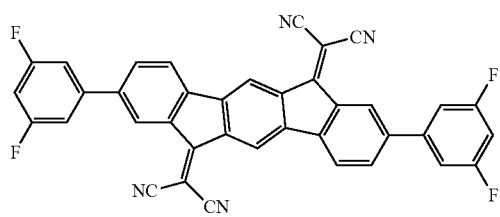
(A-165)
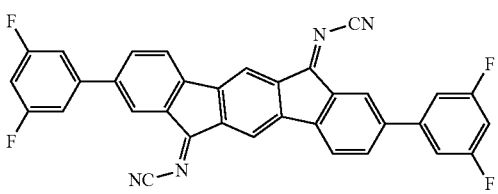
(A-166)
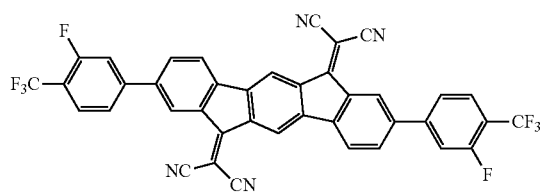
(A-167)
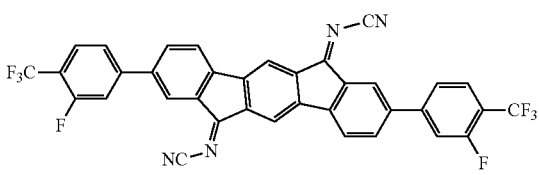
(A-168)
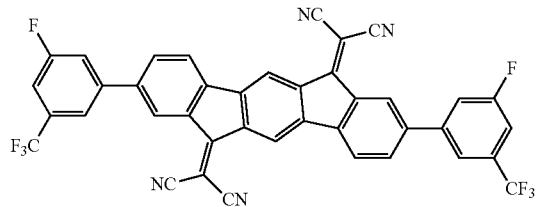
(A-169)
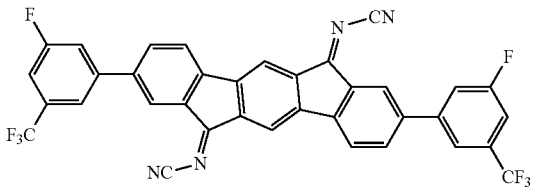

-continued
(A-171)
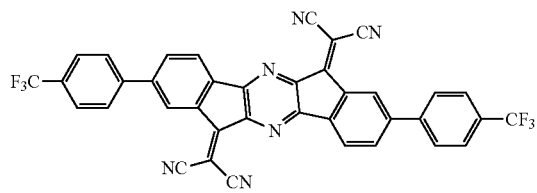
(A-172)
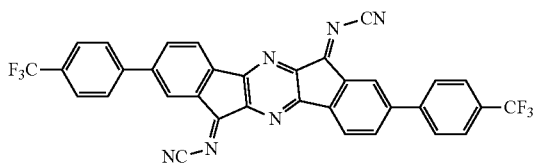
(A-173)
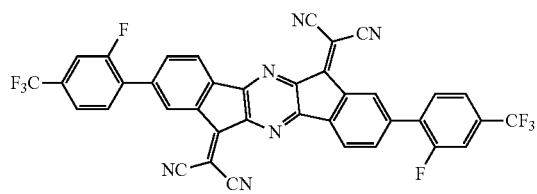
(A-174)
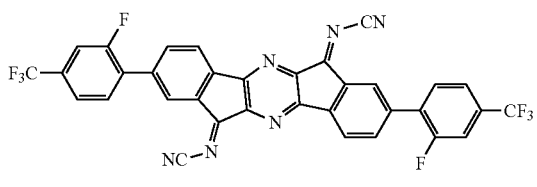
(A-175)
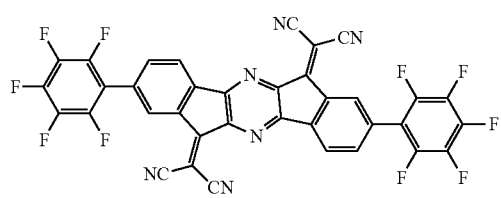
(A-176)
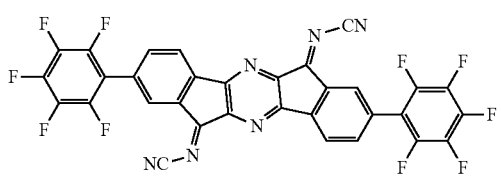
(A-177)
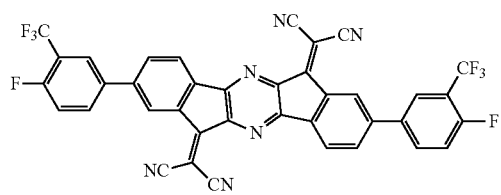
(A-178)
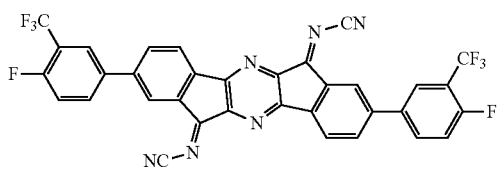
(A-179)
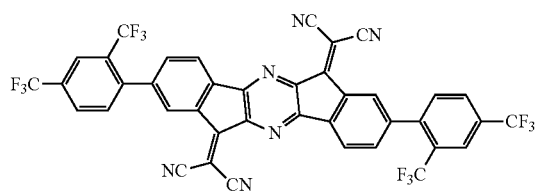
(A-180)
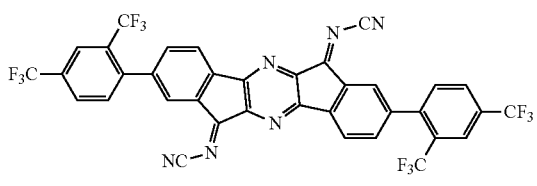
(A-181)
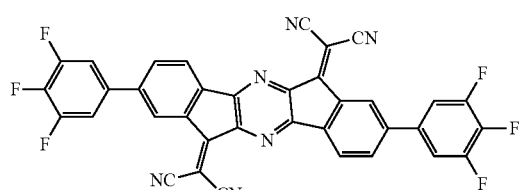
(A-182)
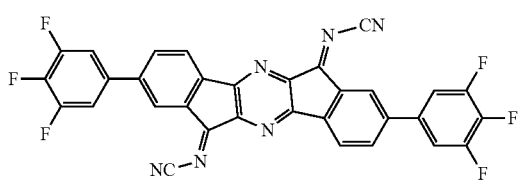
(A-183)
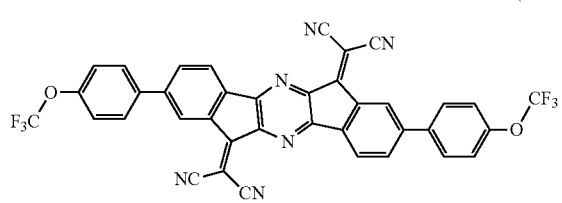
(A-184)
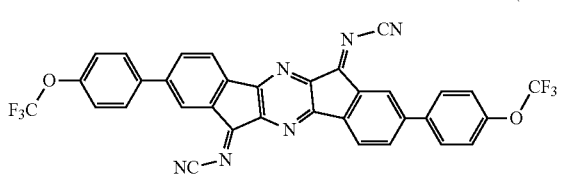

-continued
(A-185) 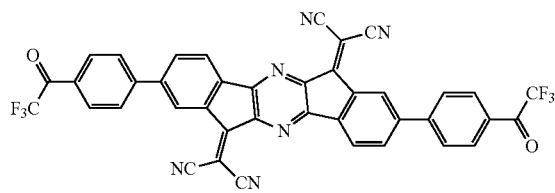
(A-186) 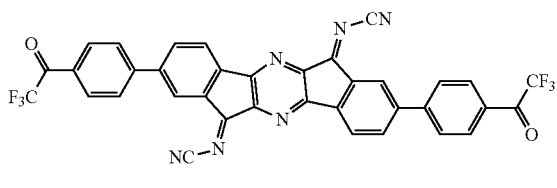
(A-187) 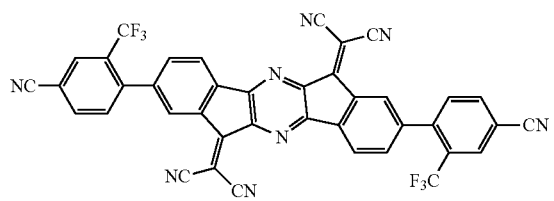
(A-188) 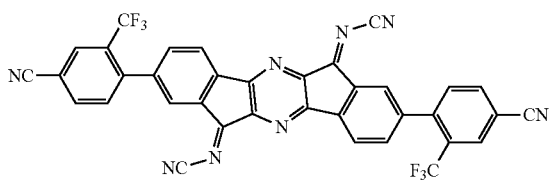
(A-189) 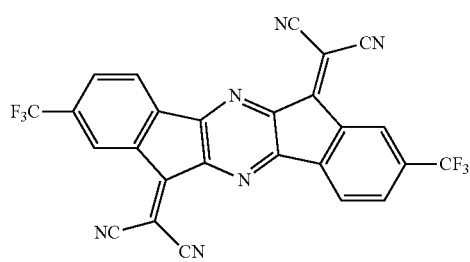
(A-190) 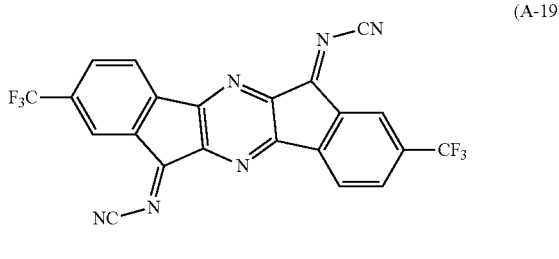
(A-191) 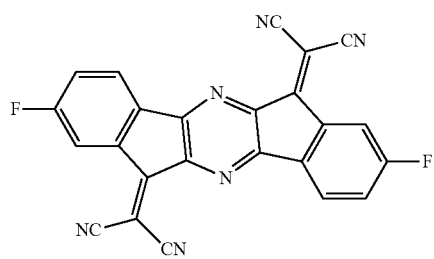
(A-192) 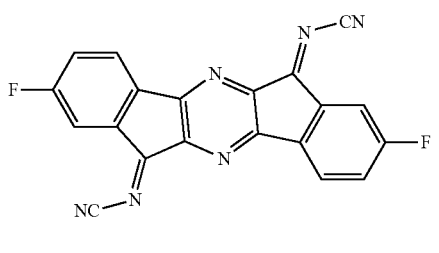
(A-193) 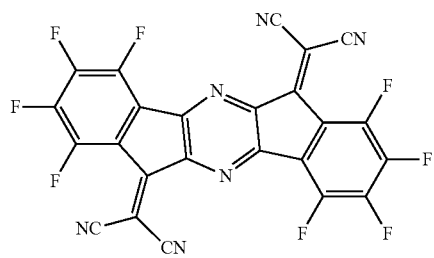
(A-194) 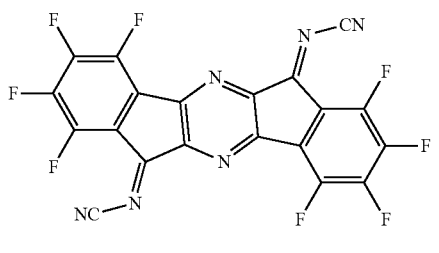
(A-195) 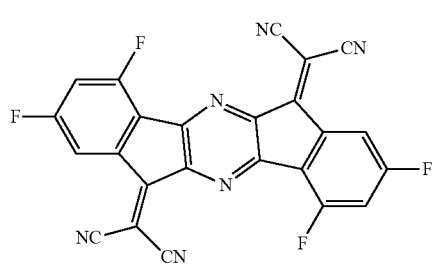
(A-196) 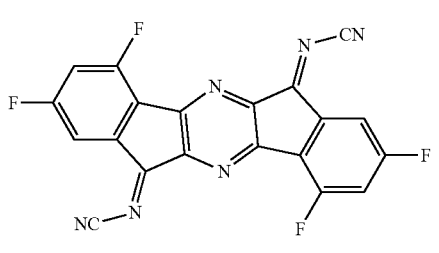

-continued
(A-197)
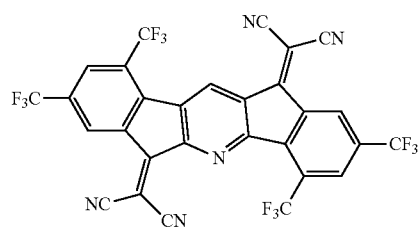
(A-198)
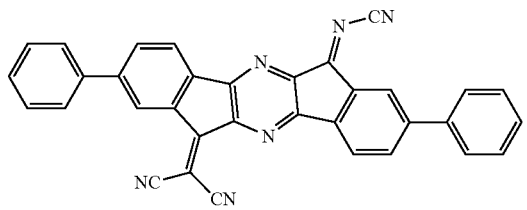
(A-199)
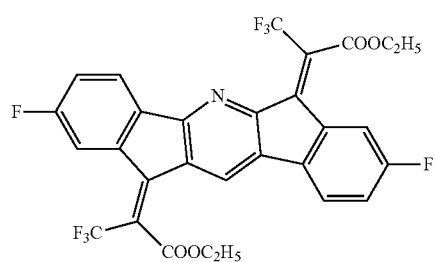
(A-200)
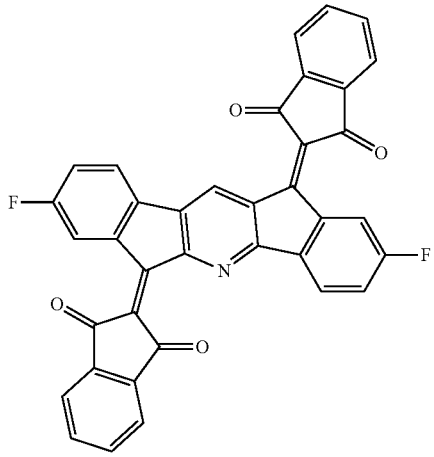
(A-201)
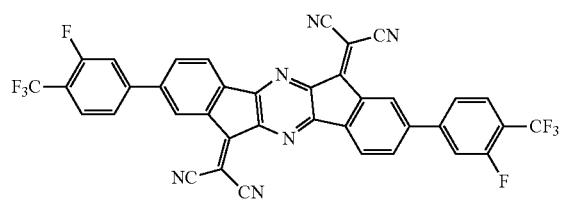
(A-202)
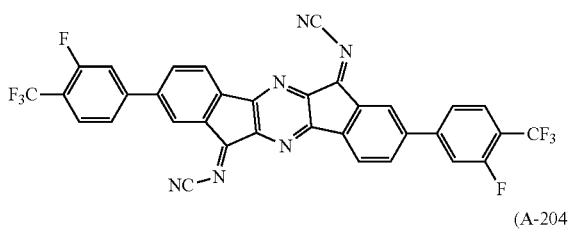
(A-203)
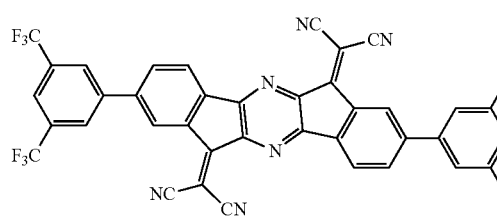
(A-204)
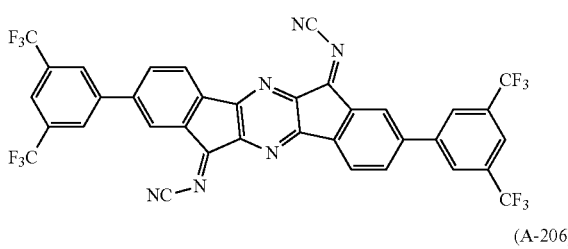
(A-205)
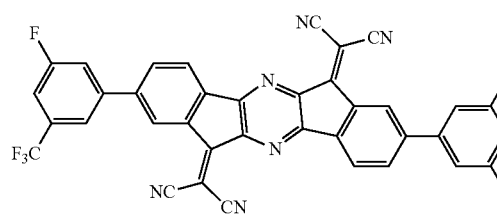
(A-206)
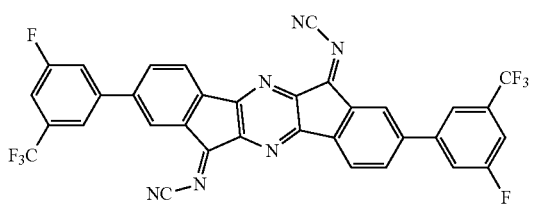
(A-207)
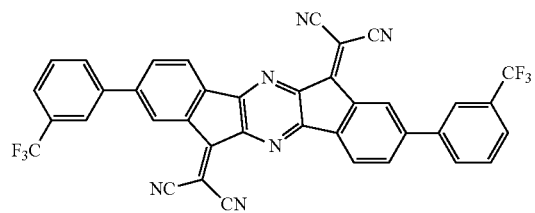
(A-208)
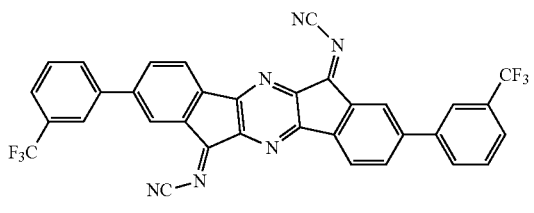

-continued
(A-209)
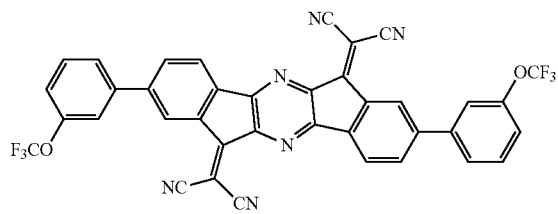
(A-210)
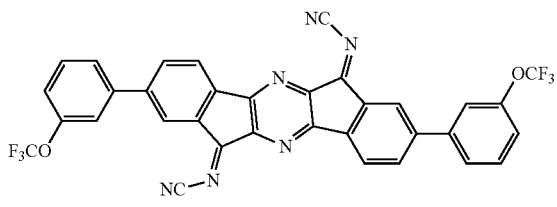
(A-211)
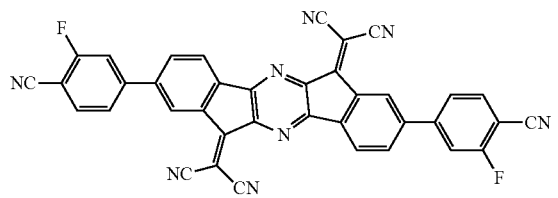
(A-212)
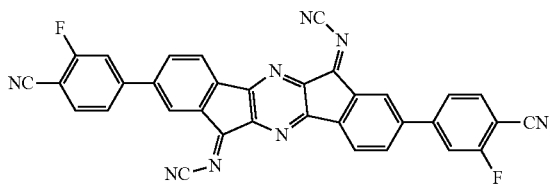
(A-213)
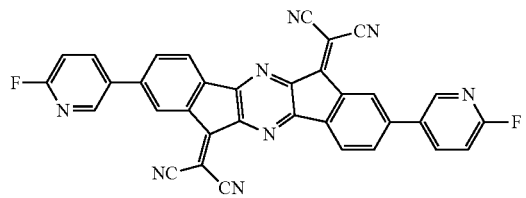
(A-214)
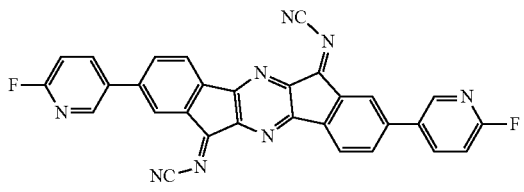
(A-215)
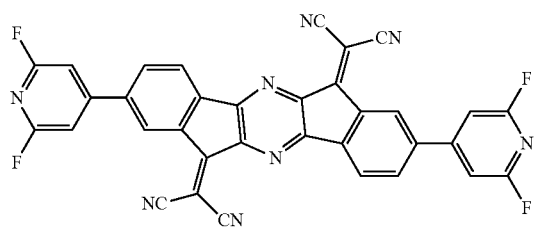
(A-216)
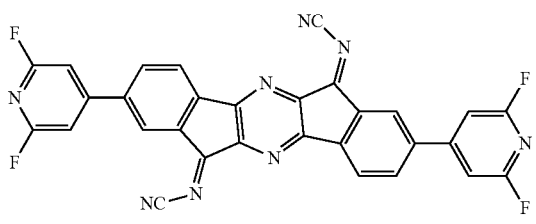
(A-217)
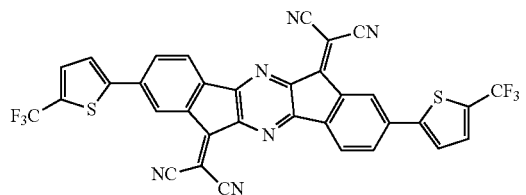
(A-218)
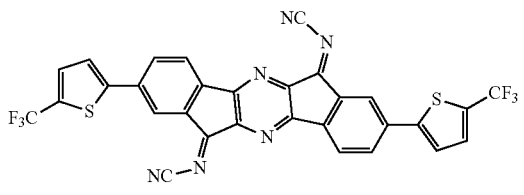
(A-219)
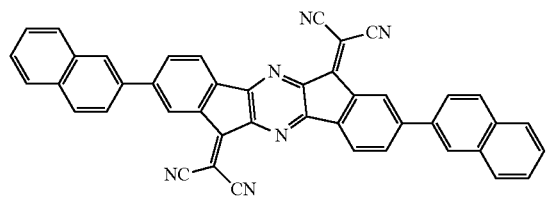
(A-220)
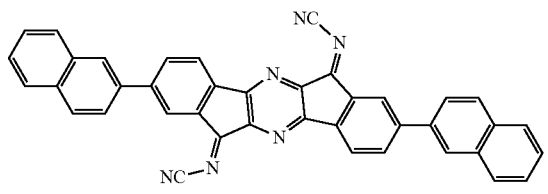

-continued
(A-221)
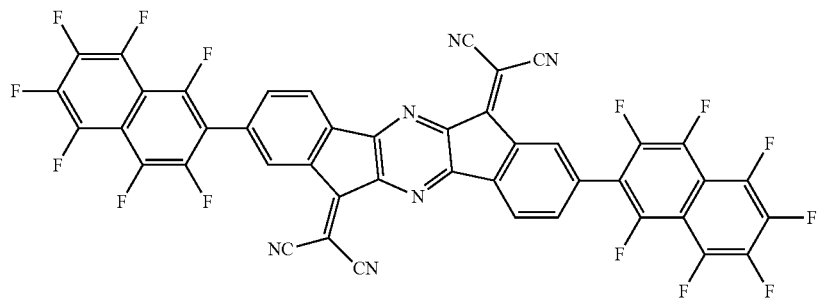
(A-222)
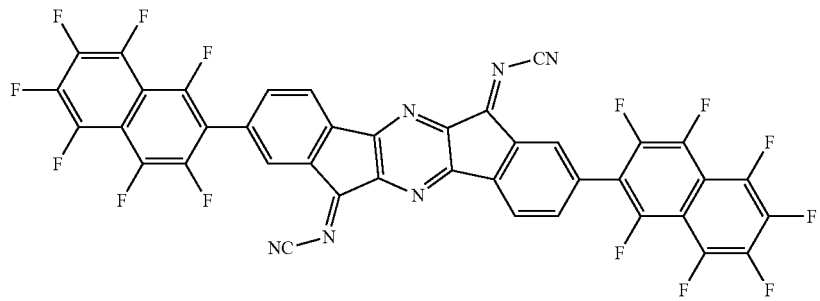
(A-223)
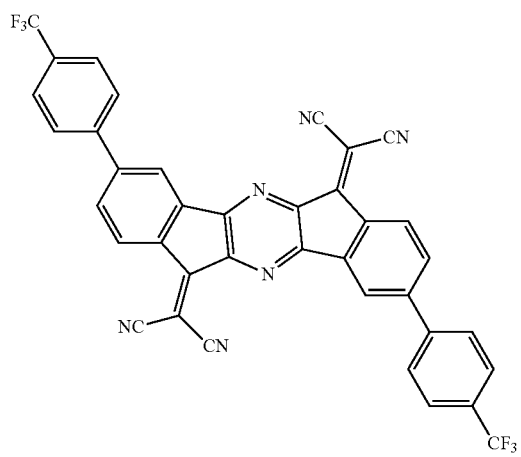
(A-224)
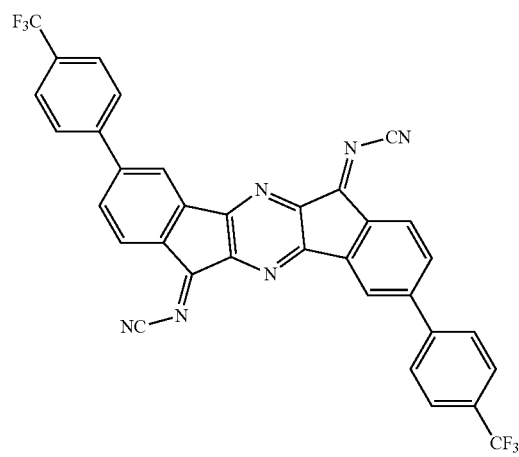
(A-225)
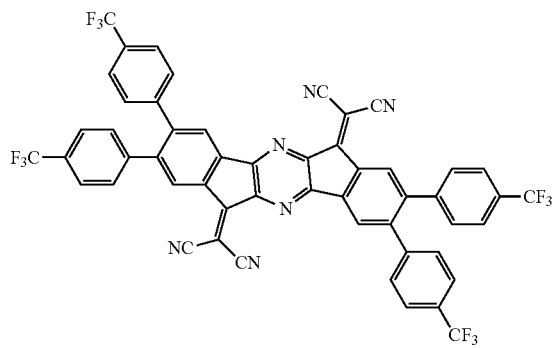
(A-226)
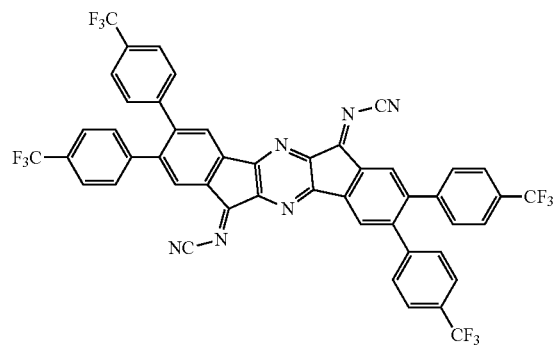

-continued
(A-227)
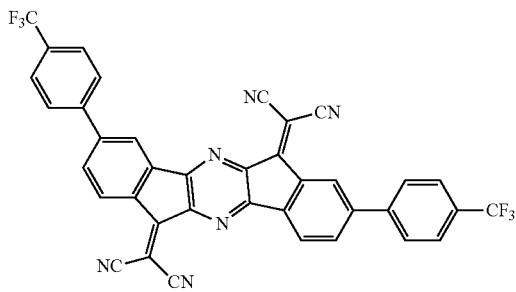
(A-228)
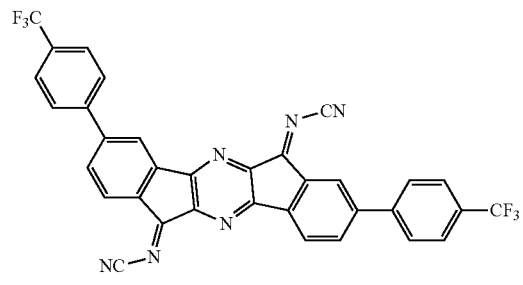
(A-229)
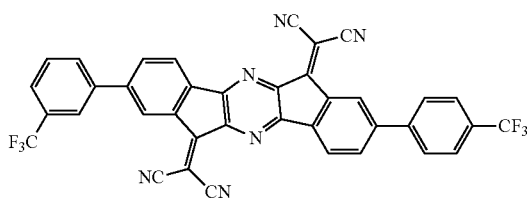
(A-230)
(A-231)
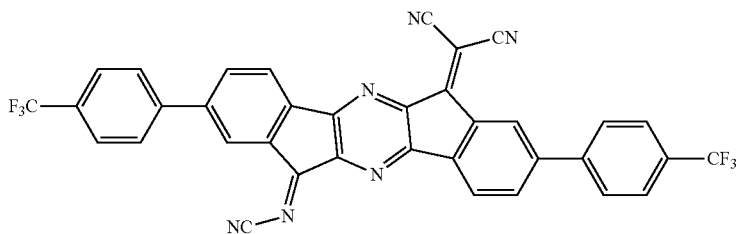
(A-232)
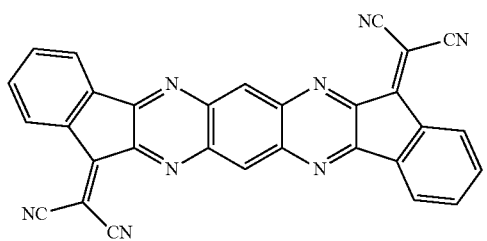
(A-233)
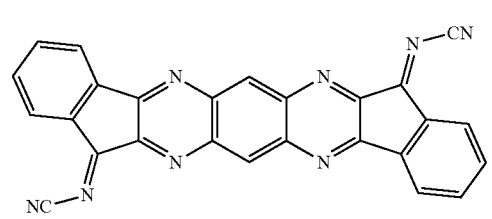
(A-234)
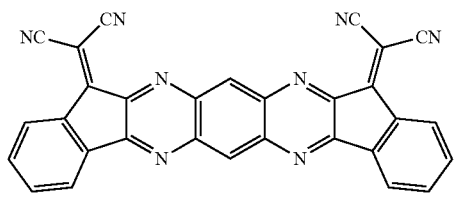
(A-235)
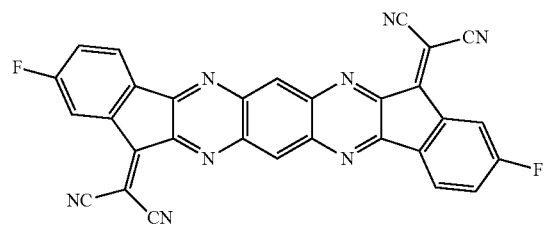
(A-236)
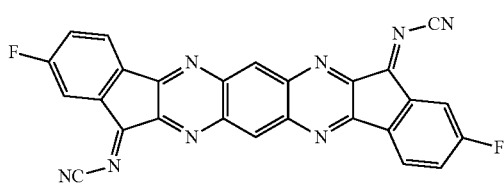
(A-237)
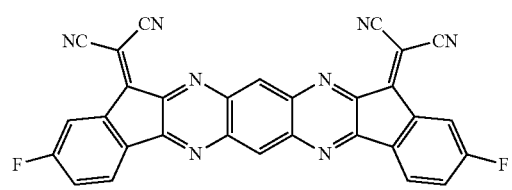

-continued
(A-238) 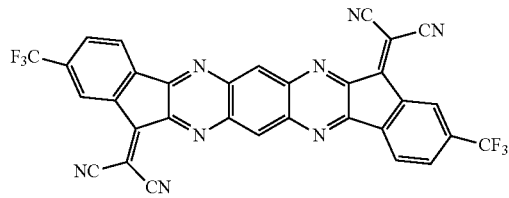
(A-239) 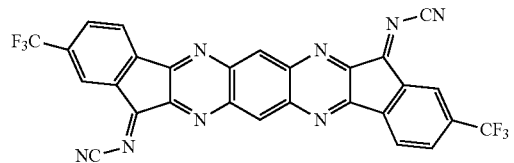
(A-240) 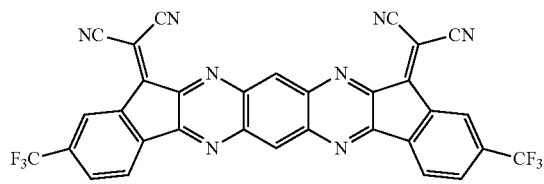
(A-241) 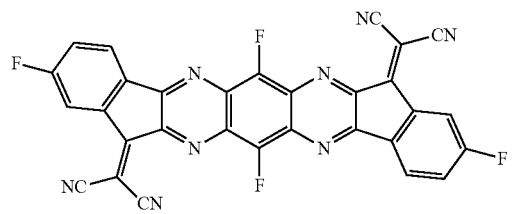
(A-242) 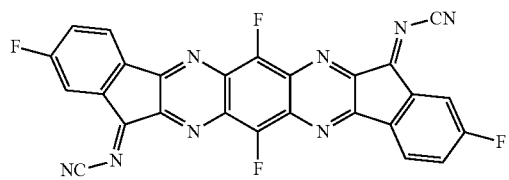
(A-243) 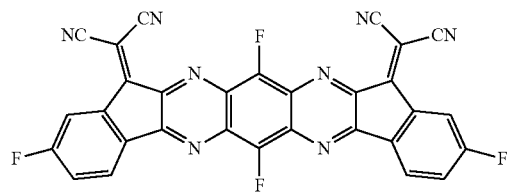
(A-244) 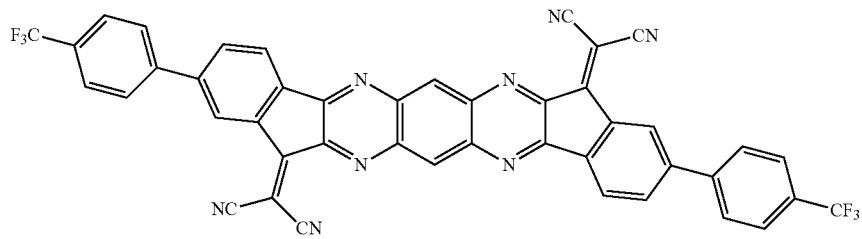
(A-245) 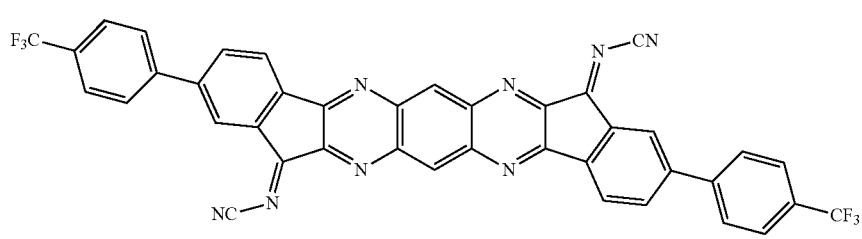
(A-246) 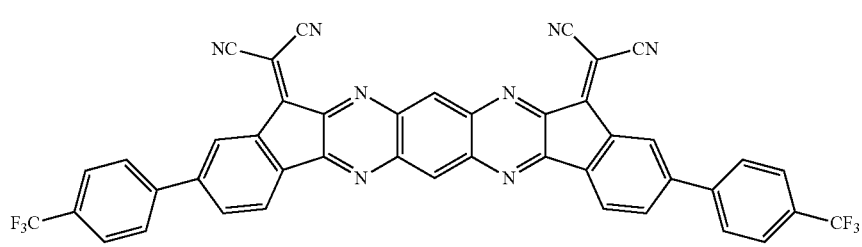

-continued (A-247)
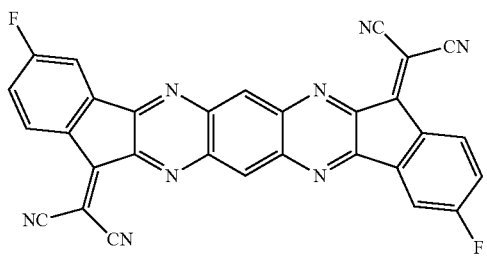

(A-248)
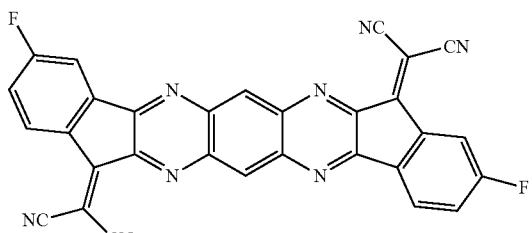

(A-249)
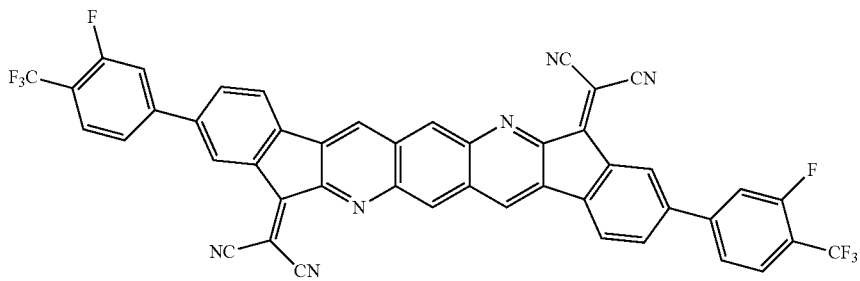

(A-250)
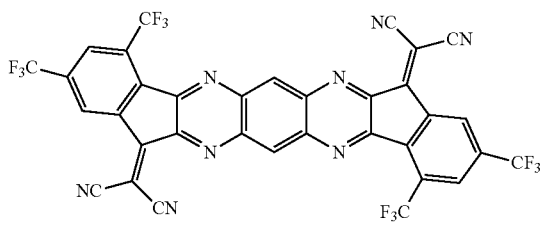

(A-251)
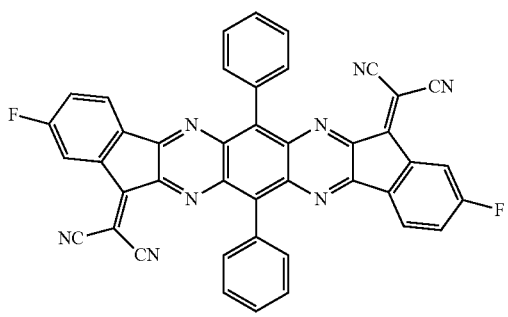

It suffices that the organic EL device of the invention have the indenofluorenedione derivative represented by the above formula (I) in the P layer of the charge-generating layer. As for the anode, the emitting unit, the cathode or the like as other constitution elements, elements known in this technical field can be used appropriately.

Each element constituting the organic EL device of the invention will be explained below.

(Substrate)

The organic EL device of the invention is formed on a substrate. The substrate serves to support the organic EL device. If emission from the emitting unit is outcoupled through the substrate, the substrate is required to be transparent. In this case, the substrate preferably has a transmittance of 50% or more for light rays within visible ranges of 400 to 700 nm.

Specific examples thereof include glass plates and polymer plates. Examples of the glass plate include soda-lime glass, barium/strontium-containing glass, lead glass, aluminosilicate glass, borosilicate glass, barium borosilicate glass, and quartz. Examples of the polymer plate include polycarbonate, acrylic polymer, polyethylene terephthalate, polyethersulfide, and polysulfone.

Transparency is not required when the supporting substrate is positioned in the direction opposite to the light-outcoupling direction.

(Anode)

The anode of the organic EL device plays a role for injecting holes into the hole-transporting layer or the emitting layer. When transparency is required for the anode, indium tin oxide alloy (ITO), tin oxide (NESA), indium zinc oxide alloy (IZO), gold, silver, platinum, copper, and the like may be used as the material for the anode. When the anode is a reflective electrode which does not require transparency, a metal such as aluminum, molybdenum, chromium, and nickel or alloys thereof with other metals can also be used.

In particular, when an anode having a small work function (for example, 5.0 eV or less) is used in combination with the hole-injecting layer using the material for an organic EL device of the invention, donating and receiving electrons are possible, whereby excellent injection properties are exhibited.

Although these materials may be used individually, alloys thereof or materials wherein another element is added to the materials can be appropriately selected for use.

The anode can be formed by forming these electrode materials into a thin film by vapor deposition, sputtering or the like. In the case where emission from the emitting layer is outcoupled through the anode, the transmittance of the anode for the emission is preferably more than 10%. The sheet resistance of the anode is preferably several hundred Ω/□ or less. The film thickness of the anode, which varies depending upon the material thereof, is usually from 10 nm to 1 μm, preferably from 10 to 200 nm.

(Emitting Unit)

The emitting unit has a single layer or stacked layer structure that at least comprises an emitting layer. The emitting unit is preferably of a multilayer structure in which a first organic layer, an emitting layer and a second organic layer are provided from the anode. Specifically, a multilayer structure comprising a hole-transporting region/emitting layer/electron-transporting region can be mentioned.

The hole-transporting region is formed of a single layer of a hole-injecting layer or a hole-transporting layer, or a stacked structure formed by stacking a plurality of these layers.

The electron-transporting region is formed of a single layer of an electron-injecting layer or an electron-transporting layer, or a stacked structure formed by stacking a plurality of these layers.

The organic EL device of the invention has two or more emitting units. Emitting units may be formed of the same material or may be formed of different materials.

The layer structure of each emitting unit may be the same or different. For example, in the organic EL device shown in FIG. 1, the electron-transporting layer of the first emitting unit 30A can be omitted, and the emitting unit may be of a two layer structure of the hole-transporting layer 31A and the emitting layer 32A.

The emission colors of the emitting units may be the same or different. For example, in the device 1 shown in FIG. 1, the emission color of the first emitting unit 30A is allowed to be yellow, and the emission color of the second emitting unit 30B to be blue. In this case, a white emitting organic EL device can be obtained by mixing two colors.

Hereinbelow, an explanation will be made on the emitting layer, the hole-transporting region and the electron-transporting region constituting the emitting unit.

(A) Emitting Layer

As the emitting layer, a layer formed of a host material and a dopant material is preferable.

As the host material of the organic EL device of the invention, rubrene, anthracene, tetracene, pyrene, perylene or the like can be used. It is further preferred that the host material of the organic EL device of the invention comprise an anthracene derivative, particularly an anthracene derivative represented by the following formula (1):

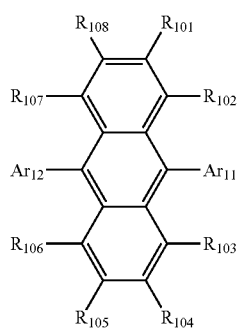

(1)

wherein $Ar_{11}$ and $Ar_{12}$ are independently a substituted or unsubstituted aryl group including 6 to 30 ring carbon atoms or a substituted or unsubstituted heterocyclic group including 5 to 30 ring atoms; and $R_{101}$ to $R_{108}$ are independently a halogen atom, a fluorine atom, a substituted or unsubstituted alkyl group including 1 to 10 carbon atoms, a substituted or unsubstituted cycloalkyl group including 3 to 10 carbon atoms, a substituted or unsubstituted alkylsilyl group including 3 to 30 carbon atoms, a substituted or unsubstituted arylsilyl group including 8 to 30 ring carbon atoms, a substituted or unsubstituted alkoxy group including 1 to 20 carbon atoms, a substituted or unsubstituted aryloxy group including 6 to 20 ring carbon atoms, a substituted or unsubstituted aryl group including 6 to 30 ring carbon atoms, or a substituted or unsubstituted heterocyclic group including 5 to 30 ring atoms.

As the emitting dopant, a fluorescent dopant and a phosphorescent dopant can be given.

A fluorescent dopant is a compound that can emit light from a singlet exciton. A fluorescent dopant is preferably a compound selected from an amine-based compound, an aromatic compound, a chelate derivative such as tris(8-quinolinolato)aluminum complex, a coumarin derivative, a tetraphenylbutadiene derivative, a bistyrylarylene derivative and an oxadiazole derivative according to the required emission color. A styrylamine compound, a styryldiamine compound, an arylamine compound, an aryldiamine compound and an aromatic compound are more preferable, with a fused polycyclic amine derivative and an aromatic compound being further preferable. These fluorescent dopants may be used single or in combination of two or more.

As the fused polycyclic amine derivative, one represented by the following formula (2) is preferable.

(2)

In the formula, Y is a substituted or unsubstituted fused aryl group including 10 to 50 ring carbon atoms.

$Ar_{21}$ and $Ar_{22}$ are independently a substituted or unsubstituted aryl group including 6 to 50 ring carbon atoms or a substituted or unsubstituted heterocyclic group including 5 to 50 ring atoms.

The fused aryl group is a group in which two or more ring structures are fused in the above-mentioned aryl group.

As the fused aryl group, a fused aryl group including 10 to 50 (preferably 10 to 30, more preferably 10 to 20) ring carbon atoms. Among the above-mentioned specific examples of the aryl group, a naphthyl group, an anthryl group, a pyrenyl group, a chrysenyl group, a phenanthryl group, a fluorenyl group, a fluoranthenyl group, an acenaphthofluoranthenyl group, a naphthacenyl group or the like can preferably be given.

Specific examples of Y include the above-mentioned fused aryl group. Y is preferably a substituted or unsubstituted anthryl group, a substituted or unsubstituted pyrenyl group, a substituted or unsubstituted chrysenyl group, and an acenaphthofluoranthenyl group.

Preferable examples of $Ar_{21}$ and $Ar_{22}$ include a substituted or unsubstituted phenyl group and a substituted or unsubstituted dibenzofuranyl group. Preferable examples of substituents for $Ar_{201}$ and $Ar_{202}$ include an alkyl group, a cyano group and a substituted or unsubstituted silyl group. n is an integer of 1 to 4, preferably an integer of 1 or 2.

As the aromatic compound, a fluoranthene compound represented by the following formula (3) is preferable.

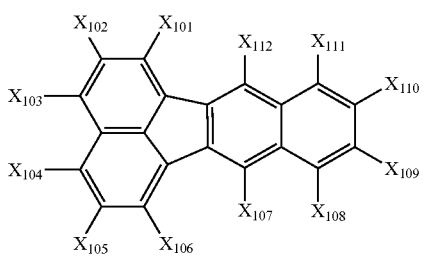
(3)

In the formula $X_{101}$ to $X_{106}$ and $X_{108}$ to $X_{111}$ are independently selected from a hydrogen atom, a substituted or unsubstituted aryl group including 6 to 30 ring carbon atoms, a substituted or unsubstituted heterocyclic group including 5 to 30 ring atoms, a substituted or unsubstituted alkyl group including 1 to 10 carbon atoms, a substituted or unsubstituted cycloalkyl group including 3 to 8 ring carbon atoms, a substituted or unsubstituted alkoxy group including 1 to 20 carbon atoms, a substituted or unsubstituted aralkyl group including 7 to 50 carbon atoms, a substituted or unsubstituted aryloxy group including 6 to 50 ring atoms, a substituted or unsubstituted arylthio group including 5 to 50 ring atoms, a substituted or unsubstituted alkoxycarbonyl group including 2 to 50 carbon atoms, an amino group substituted by a substituted or unsubstituted aryl group including 6 to 30 ring carbon atoms, a halogen atom, a cyano group, a nitro group, a hydroxyl group and a carboxyl group.

$X_{107}$ and $X_{112}$ are independently selected from a substituted or unsubstituted aryl group including 6 to 30 ring carbon atoms, a substituted or unsubstituted heterocyclic group including 5 to 30 ring atoms, a substituted or unsubstituted alkyl group including 1 to 20 carbon atoms, and a substituted or unsubstituted cycloalkyl group including 3 to 8 ring carbon atoms.

However, $X_{103}$ and $X_{104}$ are substituents different from each other.

In $X_{101}$ to $X_{112}$, adjacent substituents may be bonded with each other to form a saturated or unsaturated ring structure, and these ring structures may be substituted.

$X_{104}$ or $X_{103}$ of the formula (3) is preferably an aryl group including 6 to 30 ring carbon atoms. The preferred substituent of the "substituted or unsubstituted" of the formula (3) is a cyano group or a halogen atom.

In the formula (3), as examples of the aryl group, the heterocyclic group, the alkyl group, the cycloalkyl group, the alkoxy group, the aralkyl group, the aryloxy group, the arylthio group, the alkoxycarbonyl group and the halogen atom, those exemplified above can be mentioned.

A host suitable for phosphorescence emission is a compound having a function of allowing a phosphorescent compound to emit light as a result of energy transfer to a phosphorescent compound from its excited state. No specific restrictions are imposed on the host compound as long as it has a large triplet energy gap and is capable of transferring exciton energy to a phosphorescent compound, and can be selected appropriately depending on the intended use.

Specific examples of the host compound include a fused ring compound formed of a combination of a benzene ring, a naphthalene ring or a heterocyclic ring, a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene compound, a porphyrin-based compound, an anthraquinodimethane derivative, an anthrone derivative, a diphenylquinone derivative, a thiopyranedioxide derivative, a carbodimide derivative, a fluorenylidenemethane derivative, a distyrylpyrazine derivative, and a heterocyclic tetracarboxylic acid anhydride such as a naphthaleneperylene; metal complexes such as a phthalocyanine derivative and a 8-quinolinol derivative; various metal complexes represented by metal complexes including metal phthalocyanine, benzoxazole or benzothiazole as a ligand; conductive high-molecular oligomer such as a polysilane-based compound, a poly(N-vinylcarbazole)derivative, an aniline-based copolymer, a thiophene oligomer and polythiophene; and a high-molecular compound such as a polythiophene derivative, a polyphenylene derivative, a polyphenylenevinylene derivative, and a polyfluorene derivative can be given. These host compounds may be used singly or in combination of two or more.

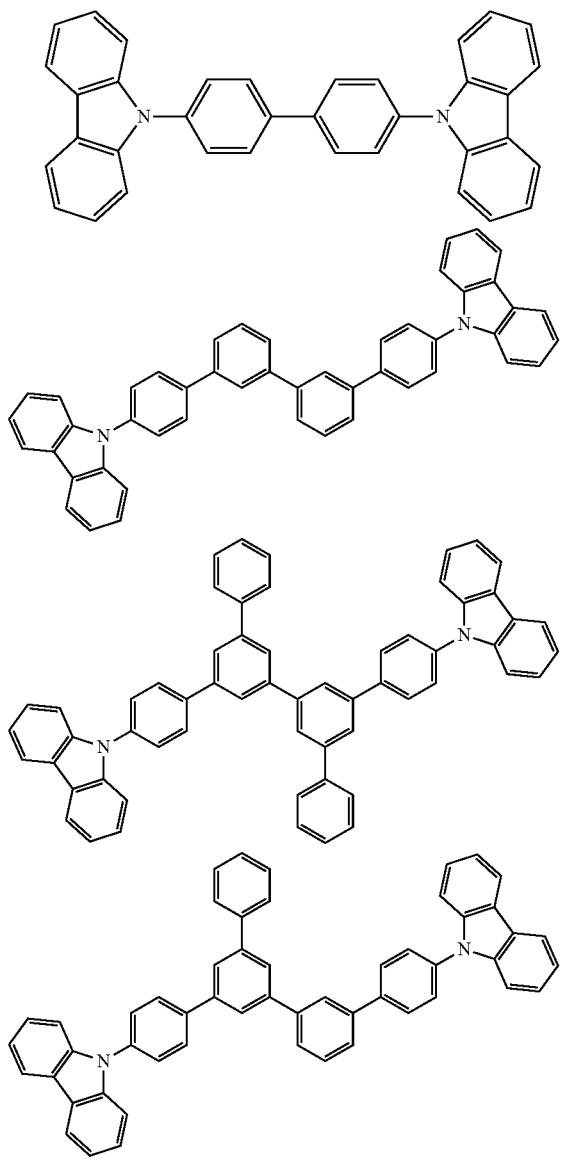

-continued

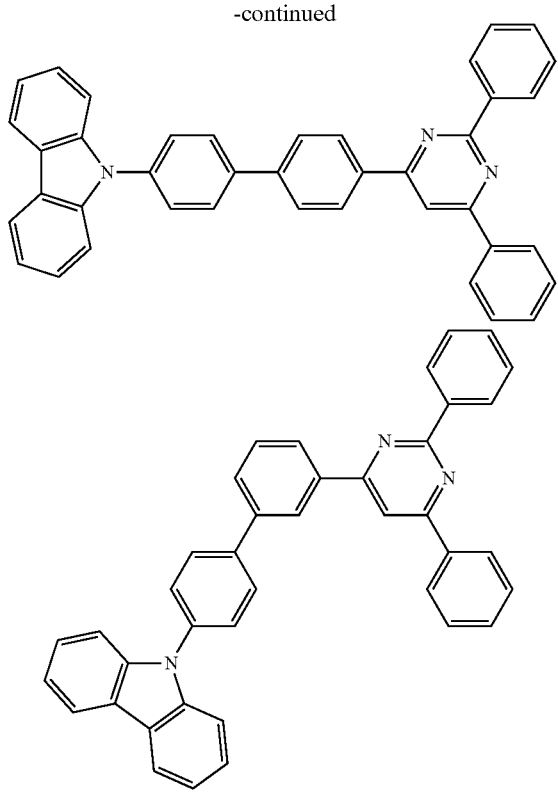

A phosphorescent dopant is a compound that can emit light from triplet excitons. The type of the phosphorescent dopant is not limited as long as it can emit from triplet excitons. A phosphorescent dopant is preferably a metal complex containing at least one metal selected from Ir, Ru, Pd, Pt, Os and Rd. A porphyrin metal complex or an ortho-metalated complex is preferable. As the porphyrin metal complex, a porphyrin platinum complex is preferable. The phosphorescent compound may be used singly or in combination of two or more.

There are various ligands forming an ortho-metalated metal complex. As a preferred ligand, a 2-phenylpyridine derivative, a 7,8-benzoquinoline derivative, a 2-(2-thienyl) pyridine derivative, a 2-(1-naphthyl)pyridine derivative, a 2-phenylquinoline derivative or the like can be given. These derivatives may have substituents, if necessary. In particular, those obtained by introducing a fluorine compound or a trifluoromethyl group is preferable as a blue dopant. It may have a ligand other than the above-mentioned ligands, e.g. acetylacetonate and picric acid, as an auxiliary ligand.

The content of the phosphorescent dopant in the emitting layer is not particularly restricted, and it may be appropriately selected depending on the purpose. For example, the content is 0.1 to 70 mass %, with 1 to 30 mass % being preferable. When the content of the phosphorescent compound is 0.1 mass % or more, it is possible to prevent emission from becoming weak, whereby the effects of the presence of the phosphorescent dopant can be fully exhibited. By allowing the content to be 70 mass % or less, it is possible to suppress a phenomenon called concentration quenching, thereby to prevent lowering of device performance.

According to need, the emitting layer may contain a hole-transporting material, an electron-transporting material and a polymer binder.

The thickness of the emitting layer is preferably 5 to 50 nm, more preferably 7 to 50 nm, and most preferably 10 to 50 nm. By allowing the thickness of the emitting layer to be 5 nm or more, formation of the emitting layer becomes easy, whereby adjustment of chromaticity is facilitated. By allowing the thickness to be 50 nm or less, an increase in driving voltage can be prevented.

(B) Hole-Transporting Region

As the layers of the hole-transporting region, a hole-transporting layer, a hole-injecting layer or the like can be mentioned. The hole-transporting layer is a layer that assists injection of holes into the emitting layer, and transports holes to the emitting region. The hole-transporting layer exhibits a high hole mobility, and normally has a low ionization energy of 5.5 eV or less. It is preferable to form the hole-transporting layer using a material that transports holes to the emitting layer at a low field intensity. It is more preferable to use a material having a hole mobility of at least $10^{-4}$ cm$^2$/V·s when an electric field of $10^4$ to $10^6$ V/cm is applied, for example.

Specific examples of the material for forming the hole-transporting layer include triazole derivatives, oxadiazole derivatives, imidazole derivatives, polyarylalkane derivatives, pyrazoline derivatives and pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, polysilane-based copolymers, aniline-based copolymers, conductive high-molecular polymers (in particular, thiophene oligomer) or the like can be given.

In the hole-injecting layer or the hole-transporting layer (including the hole-injecting/transporting layer), an aromatic amine compound, for example, an aromatic amine derivative represented by the following formula (4) is preferably employed.

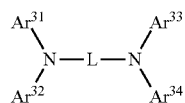 (4)

In the formula (4), Ar$^{31}$ to Ar$^{34}$ are an aromatic hydrocarbon group including 6 to 50 ring carbon atoms (it may have a substituent), a fused aromatic hydrocarbon group including 6 to 50 ring carbon atoms (it may have a substituent), an aromatic heterocyclic group including 2 to 40 ring carbon atoms (it may have a substituent), a fused aromatic heterocyclic group including 2 to 40 ring carbon atoms (it may have a substituent), a group formed by bonding of the aromatic hydrocarbon group with the aromatic heterocyclic group, a group formed by bonding of the aromatic hydrocarbon group with the fused aromatic heterocyclic group, a group formed by bonding of the fused aromatic hydrocarbon group with the aromatic heterocyclic group, or a group formed by bonding of the fused aromatic hydrocarbon group with the fused aromatic heterocyclic group.

L is a single bond or a group similar to Ar$^{31}$ to Ar$^{34}$.

The aromatic amine represented by the following formula (5) is preferably used for the formation of the hole-injecting layer or the hole-transporting layer.

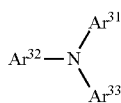

(5)

In the formula (5), $Ar^{31}$ to $Ar^{33}$ are as defined for $Ar^{31}$ to $Ar^{34}$ in the formula (4).

The hole-injecting layer is a layer that is provided for further assisting injection of holes. As the material for the hole-injecting layer, the material for an organic EL device of the invention may be used alone or in combination with other materials. As other materials, similar materials to those for the hole-transporting layer can be used. In addition, a porphyrin compound, an aromatic tertiary amine compound and a styrylamine compound can also be used. Further, HAT or F4TCNQ used in the P layer of the carrier-generating layer or a compound represented by the formula (4) can be used.

Further, electroconductive oligomers such as thiophene-containing oligomers or arylamine-containing oligomers disclosed in JP-A-H08-193191 and electroconductive dendrimers such as arylamine-containing dendrimers may be used.

Further, in addition to an aromatic dimethylidene-based compound, an inorganic compound such as p-type Si and p-type SiC can also be used as the material of the hole-injecting layer.

The hole-injecting layer and the hole-transporting layer can be formed in the shape of a film from the above-mentioned compounds by a known method such as vapor vacuum deposition, spin coating, casting or LB technique. The film thickness of the hole-injecting layer and the hole-transporting layer is not particularly limited, and is usually from 1 nm to 5 μm.

(C) Electron-Transporting Region

As the layers of the electron-transporting region, an electron-injecting layer, an electron-transporting layer or the like (hereinafter, referred to as the electron-injecting layer/transporting layer) can be mentioned.

The electron-injecting/transporting layer is a layer that assists injection of electrons into the emitting layer, and transports electrons to the emitting region. The electron-injecting/transporting layer exhibits a high electron mobility.

The thickness of the electron-injecting/transporting layer is appropriately selected within the range of several nanometers to several micrometers. In particular, when the electron-injecting/transporting layer has a large thickness, it is preferable that the electron mobility be at least $10^{-5}$ cm$^2$/Vs at an applied electric field of $10^4$ to $10^6$ V/cm in order to prevent an increase in voltage.

The material used in the electron-injecting/transporting layer is preferably a metal complex of 8-hydroxyquinoline or a derivative thereof, or a nitrogen-containing heterocyclic derivative.

Specific examples of the metal complex of 8-hydroxyquinoline or the derivative thereof include metal chelate oxynoid compounds containing a chelate of oxine (generally, 8-quinolinol or 8-hydroxyquinoline). For example, tris(8-quinolinol)aluminum can be used as an electron-injecting material.

As the nitrogen-containing heterocyclic derivative, oxazole, thiazole, oxadiazole, thiadiazole, triazole, pyridine, pyrimidine, triazine, phenanthroline, benzimidazole, imidazopyridine or the like are preferable. Among them, a benzimidazole derivative, a phenanthroline derivative and an imidazopyridine derivative are preferable.

(Charge-Generating Layer)

A charge-generating layer is a layer which, when a voltage is applied, serves to inject holes to an emitting unit arranged on the side of the charge-generating layer near to the cathode, and on the other hand, serves to inject electrons to an emitting unit arranged on the side of the charge-generating layer near to the anode.

In the invention, the charge-generating layer has an N layer provided on the side nearer to the anode and a P layer provided on the side nearer to the cathode.

As the material for forming the N layer, an organic compound, an electron-donating metal, a metal compound, a metal complex or the like can be mentioned.

As the N layer, a layer comprising at least one of an alkali metal, an alkali metal compound, an organic metal complex containing an alkali metal, an alkaline earth metal, an alkaline earth metal compound, an organic metal complex containing an alkaline earth metal, a rare earth metal, a rare earth metal compound and an organic metal complex including a rare earth metal.

Examples of the alkali metals include lithium (Li), sodium (Na), potassium (K), rubidium (Rb), cesium (Cs), and the like. It is particularly preferable to use an alkali metal having a work function of 2.9 eV or less. Among these, Li, K, Rb or Cs is preferable, Li, Rb or Cs is more preferable, and Li is most preferable.

Examples of the alkaline-earth metals include calcium (Ca), magnesium (Mg), strontium (Sr), barium (Ba), and the like. It is particularly preferable to use an alkaline-earth metal having a work function of 2.9 eV or less.

Examples of the rare-earth metals include scandium (Sc), yttrium (Y), cerium (Ce), terbium (Tb), ytterbium (Yb), and the like. It is particularly preferable to use a rare-earth metal having a work function of 2.9 eV or less.

Since the above preferable metals exhibit a particularly high reducing capability, the luminance and the lifetime of the organic EL device can be improved by adding a relatively small amount of such a metal to the electron-injecting region.

Examples of the alkali metal compounds include alkali metal oxides such as lithium oxide (Li$_2$O), cesium oxide (Cs$_2$O), and potassium oxide (K$_2$O), alkali halides such as lithium fluoride (LiF), sodium fluoride (NaF), cesium fluoride (CsF), and potassium fluoride (KF), and the like. Among these, lithium fluoride (LiF), lithium oxide (Li$_2$O), and sodium fluoride (NaF) are preferable.

Examples of the alkaline-earth metal compounds include barium oxide (BaO), strontium oxide (SrO), calcium oxide (CaO), mixtures thereof (e.g., barium strontium oxide (Ba$_x$Sr$_{1-x}$O) (0<x<1) and barium calcium oxide (Ba$_x$Ca$_{1-x}$O) (0<x<1)), and the like. Among these, BaO, SrO, and CaO are preferable.

Examples of the rare-earth metal compounds include ytterbium fluoride (YbF$_3$), scandium fluoride (ScF$_3$), scandium oxide (ScO$_3$), yttrium oxide (Y$_2$O$_3$), cerium oxide (Ce$_2$O$_3$), gadolinium fluoride (GdF$_3$), terbium fluoride (TbF$_3$), and the like. Among these, YbF$_3$, ScF$_3$, and TbF$_3$ are preferable.

The organic metal complex is not particularly limited as long as the organic metal complex includes at least one of an alkali metal ion, an alkaline-earth metal ion, and a rare-earth metal ion as the metal ion. Examples of a preferable ligand include, but are not limited to, quinolinol, benzoquinolinol, acridinol, phenanthridinol, hydroxyphenyloxazole, hydroxyphenylthiazole, hydroxydiaryloxadiazoles, hydroxydiarylthiadiazoles, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, derivatives thereof, and the like.

The N layer may contain, in addition to the metals, the compounds and the complexes mentioned above, an organic compound such as an electron-injecting material or an emission material such as tris(8-quinolinol)aluminum (Alq).

As the organic compound, a nitrogen-containing heterocyclic compound is preferable, for example. As the nitrogen-containing heterocyclic compound, oxazole, thiazole, oxadiazole, thiadiazole, triazole, pyridine, pyrimidine, triazine, phenanthroline, benzimidazole, imidazopyridine or the like are preferable. Among them, a benzimidazole derivative, a phenanthroline derivative and an imidazopyridine derivative are preferable.

As specific materials, benzimidazole derivatives represented by the following formula (9) can be mentioned, but not limited thereto.

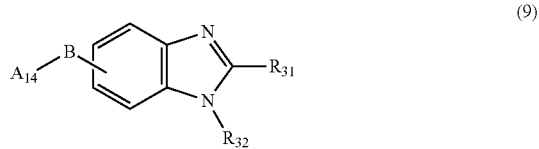

(9)

In the formula, $A_{14}$ is a hydrogen atom, a halogen atom, a substituted or unsubstituted alkyl group including 1 to 20 carbon atoms, a substituted or unsubstituted hydrocarbon group including 6 to 60 carbon atoms that comprises a polycyclic aromatic hydrocarbon group formed by 3 to 40 aromatic rings being fused, or a nitrogen-containing heterocyclic group.

The specific examples of the halogen atom and the alkyl group including 1 to 20 carbon atoms are the same as those mentioned above referring to the formula (I).

Regarding the substituted or unsubstituted hydrocarbon group including 6 to 60 carbon atoms that comprises a polycyclic aromatic hydrocarbon group formed by 3 to 40 aromatic rings being fused, as for the polycyclic aromatic hydrocarbon group formed by 3 to 40 aromatic rings being fused, anthracene, naphthacene, pentacene, pyrene, chrysene or the like can be given. As for the hydrocarbon group including 6 to 60 carbon atoms, an alkyl group, a cycloalkyl group, an aryl group or the like can be given. The specific examples of these groups are the same as those in the formula (I). As the hydrocarbon group, an aryl group is preferable. Among aryl groups, a phenyl group, a naphthyl group, a biphenyl group, a terphenyl group, a fluorenyl group or the like are preferable. These groups may have a substituent.

As the nitrogen-containing heterocyclic group, a pyridine ring, a triazine ring or the like can be given.

B is a single bond, or a substituted or unsubstituted aromatic ring group. As the aromatic ring group, a phenylene group is preferable.

$R_{31}$ and $R_{32}$ are independently a hydrogen atom, a halogen atom, a substituted or unsubstituted alkyl group including 1 to 20 carbon atoms, a substituted or unsubstituted aromatic hydrocarbon group including 6 to 60 carbon atoms, a substituted or unsubstituted nitrogen-containing heterocyclic group, or a substituted or unsubstituted alkoxy group including 1 to 20 carbon atoms. The specific examples of each group are the same as those for $A_{14}$ in the formula (I) mentioned above.

As the specific examples of the compound represented by the formula (9), compounds represented by the following formulas (9-1) to (9-49) can be given. The "Ar(α)" corresponds to the benzimidazole skeleton including $R_{31}$ and $R_{32}$ in the formula (9), the "B" corresponds to B in the formula (9). The "Ar(1)" and the "Ar(2)" correspond to $Ar_{14}$ in the formula (9), and are bonded to B in the order of Ar(1) and Ar(2).

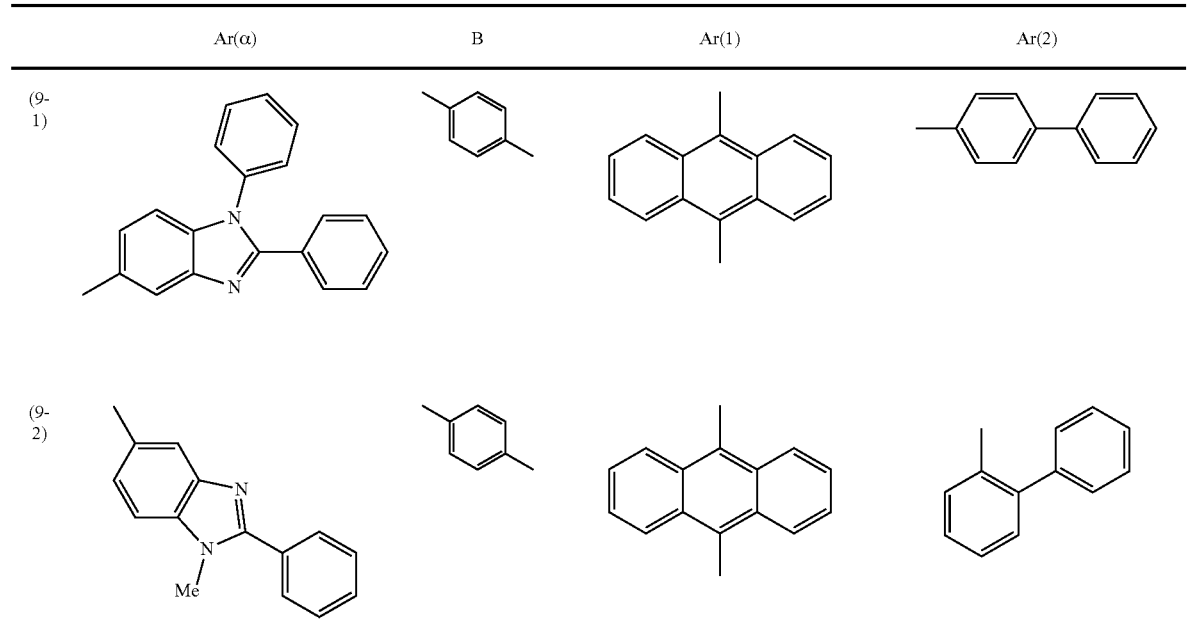

-continued

| | Ar(α) | B | Ar(1) | Ar(2) |
|---|---|---|---|---|
| (9-3) | 1-Me, 2-Ph benzimidazole (5-Me) | p-phenylene | 9,10-dimethylanthracene | 4-biphenyl |
| (9-4) | 1-Me, 2-Ph benzimidazole (5-Me) | p-phenylene | 9,10-dimethylanthracene | 2-biphenyl (via 4'-position) |
| (9-5) | 1-Ph, 2-Ph benzimidazole (5-Me) | p-phenylene | 5,12-dimethyltetracene | 2-biphenyl |
| (9-6) | 1-Et, 2-Ph benzimidazole (5-Me) | p-phenylene | 9,10-dimethylanthracene | 2-biphenyl |
| (9-7) | 1-Ph, 2-Ph benzimidazole (5-Me) | p-phenylene | 9,10-dimethylanthracene | 4-biphenyl |
| (9-8) | 1-Me, 2-Ph benzimidazole (5-Me) | p-phenylene | 9,10-dimethylanthracene | 2-(4-phenylphenyl)phenyl |

| Ar(α) | B | Ar(1) | Ar(2) |
|---|---|---|---|
| (9-9) 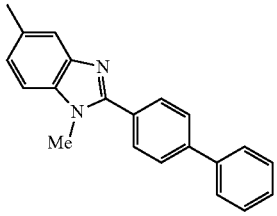 | 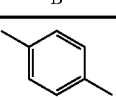 | 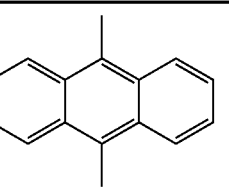 | 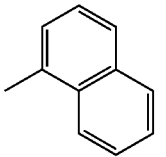 |
| (9-10) 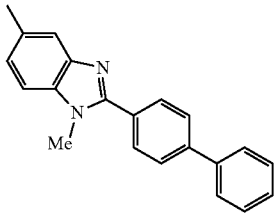 | 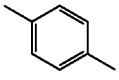 | 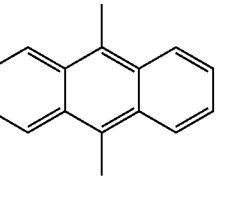 | 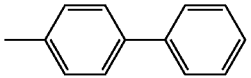 |
| (9-11) 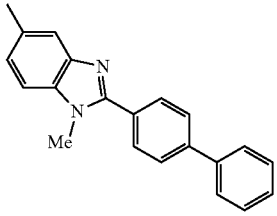 | 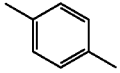 | 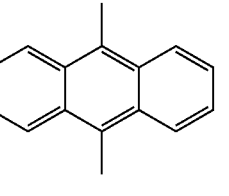 | 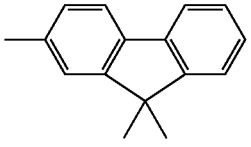 |
| (9-12) 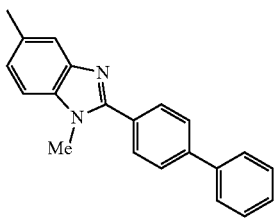 | 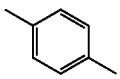 | 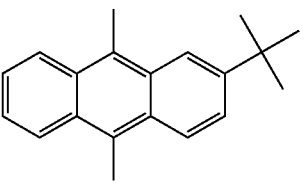 | 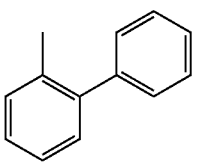 |
| (9-13) 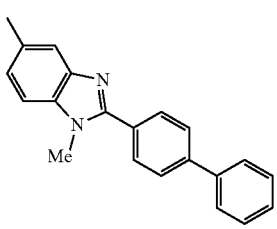 | 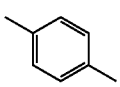 | 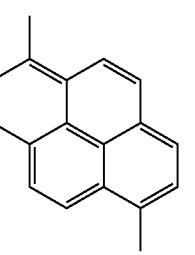 | 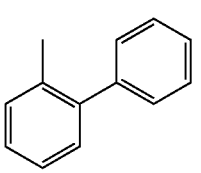 |
| (9-14) 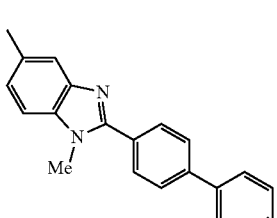 | 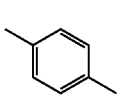 | 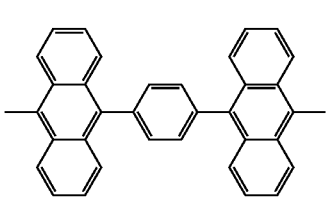 | 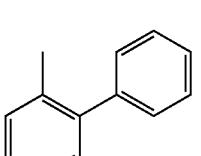 |
| (9-15) 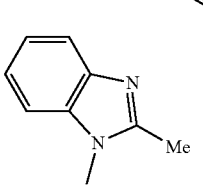 | 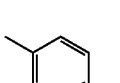 | 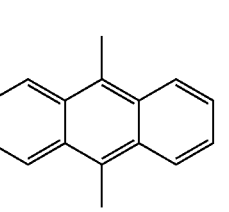 | 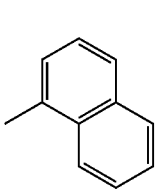 |

-continued
| | Ar(α) | B | Ar(1) | Ar(2) |
|---|---|---|---|---|
| (9-16) | 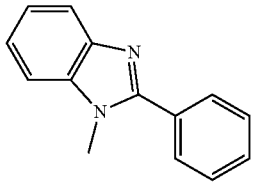 | 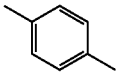 | 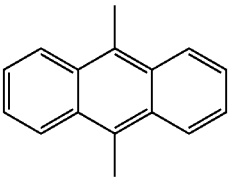 | 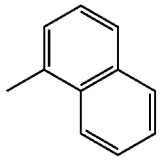 |
| (9-17) | 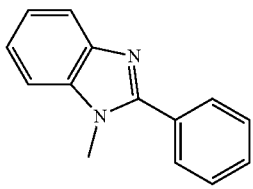 | 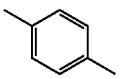 | 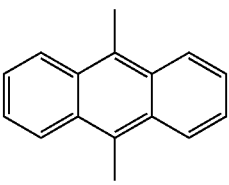 | 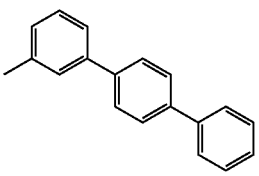 |
| (9-18) | 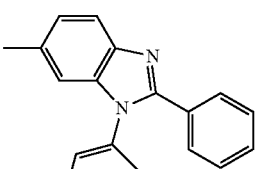 | | 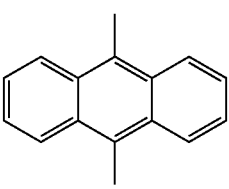 | 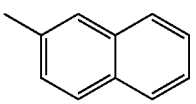 |
| (9-19) | 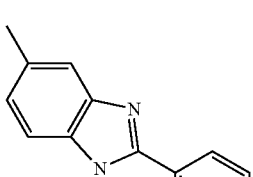 | | 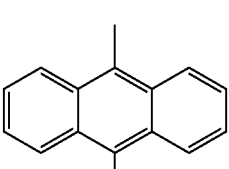 | 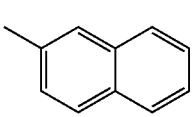 |
| (9-20) | 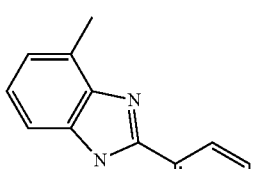 | | 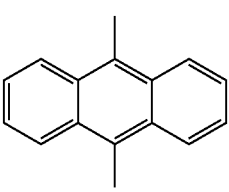 | 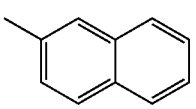 |
| (9-21) | 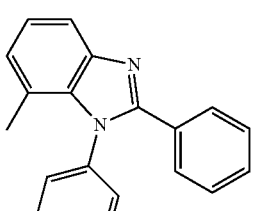 | | 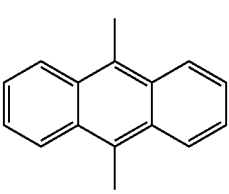 | 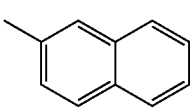 |

-continued

| | Ar(α) | B | Ar(1) | Ar(2) |
|---|---|---|---|---|
| (9-22) | | | | |
| (9-23) | | | | |
| (9-24) | | | | |
| (9-25) | | | | |
| (9-26) | | | | |
| (9-27) | | | | |

|  | Ar(α) | B | Ar(1) | Ar(2) |
|---|---|---|---|---|
| (9-28) | | | | |
| (9-29) | | | | |
| (9-30) | | | | |
| (9-31) | | | | |
| (9-32) | | | | |
| (9-33) | | | | |

-continued
| | Ar(α) | B | Ar(1) | Ar(2) |
|---|---|---|---|---|
| (9-34) | 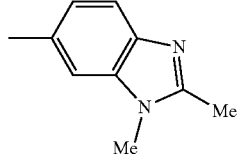 | | 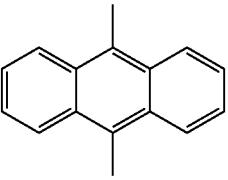 | 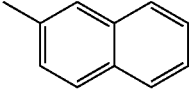 |
| (9-35) | 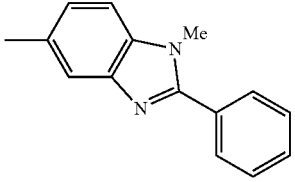 | | 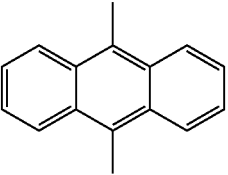 | 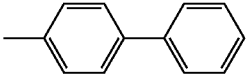 |
| (9-36) | 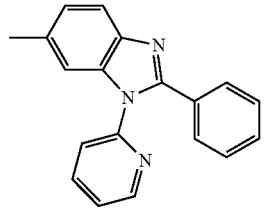 | | 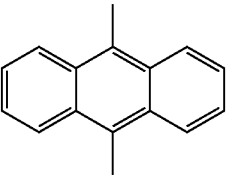 | 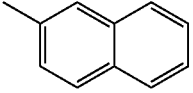 |
| (9-37) | 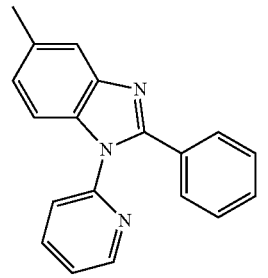 | | 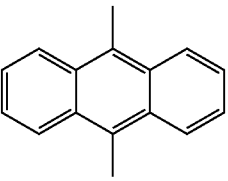 | 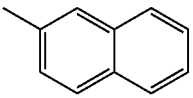 |
| (9-38) | 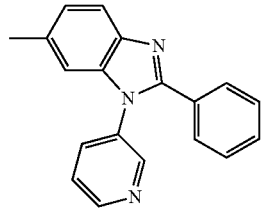 | | 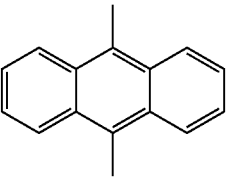 | 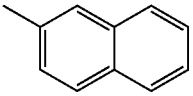 |
| (9-39) | 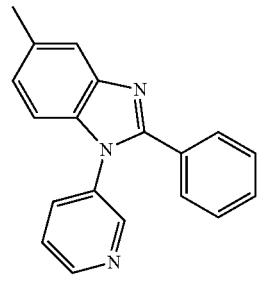 | | 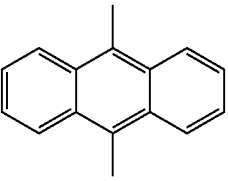 | 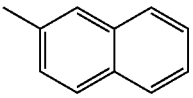 |

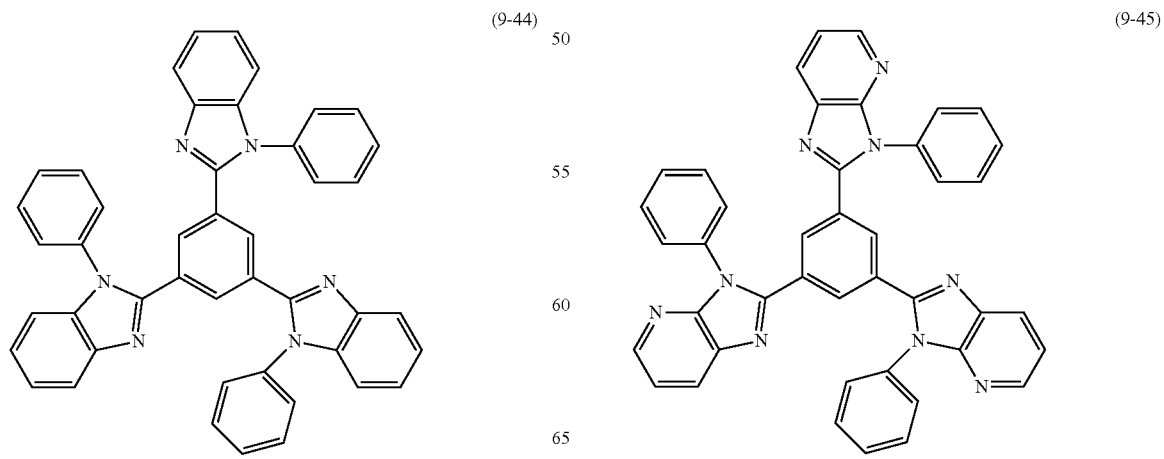

(9-46)
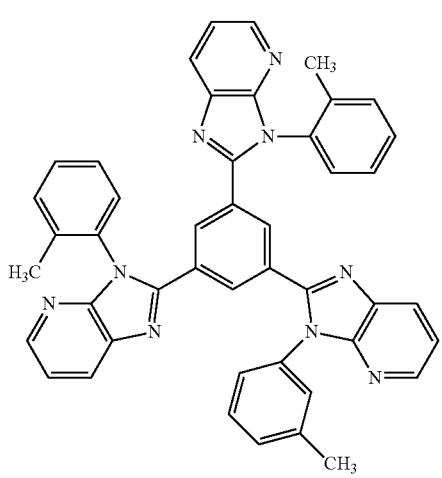

(9-47)
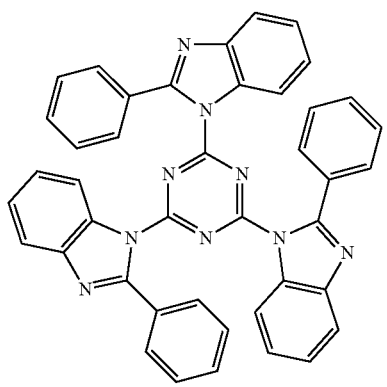

(9-48)
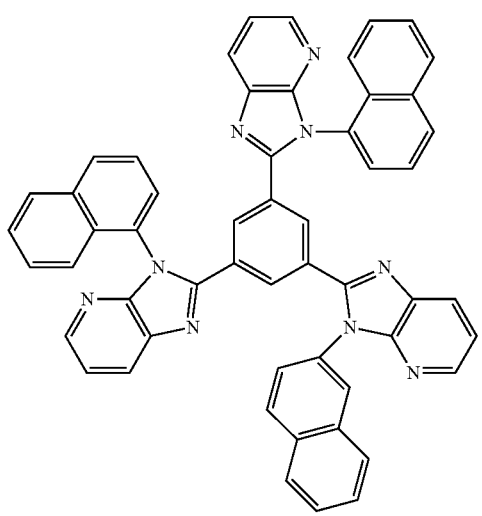

(9-49)
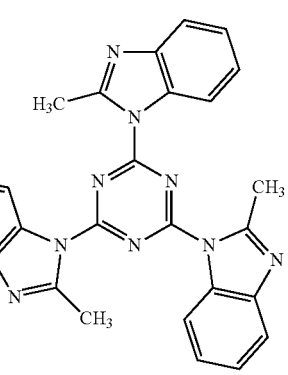

As the organic compound used in the N layer, a compound having an anthracene skeleton as the above-mentioned compounds is preferable, but not limited thereto. For example, a benzimidazole derivative including a pyrene skeleton or a chrysene skeleton instead of an anthracene skeleton may be used. The kind of the organic material is not limited to one, and a plurality of kinds of organic materials may be mixed or stacked.

The metal, the compound and the complex mentioned above are preferably formed in the interface region in the shape of a layer or islands. It is preferable to deposit an organic substance (i.e., an emitting material or an electron-injecting material that forms the interface region) simultaneously with depositing at least one of the metal, the compound and the complex by resistance heating deposition so that at least one of the metal, the compound and the complex is dispersed in the organic material. The dispersion concentration (i.e., the thickness ratio of the organic substance to the metal, the compound, and the complex) is 1000:1 to 1:1000, and preferably 100:1 to 1:1 in terms of thickness ratio.

When forming at least one of the metal, the compound and the complex in the shape of a layer, the emitting material or the electron-injecting material is formed in the shape of a layer, and at least one of the metal, the compound and the complex is deposited singly by resistance heating deposition to a thickness of preferably 0.1 nm to 15 nm.

When forming at least one of the metal, the complex and the complex in the shape of an island, the emitting material or the electron-injecting material (i.e., the organic layer at the interface) is formed in the shape of an island, and at least one of the metal, the compound and the complex is deposited singly by resistance heating deposition to a thickness of preferably 0.05 nm to 1 nm.

As for the ratio of the main component to at least one of the metal, the compound and the complex in the organic EL device according to the invention (i.e., the thickness ratio of the main component to the electron donor dopant and/or the organic metal complex) is preferably 100:1 to 1:1, and further preferably 50:1 to 4:1.

The thickness of the N layer is preferably 0.1 nm to 100 nm, with 1 nm to 50 nm being particularly preferable.

As mentioned above, the P layer comprises the compound represented by the above formula (I). The P layer may be a layer comprising the compound represented by the formula (I) or may be a layer comprising a mixture of the compound represented by the formula (I) and other materials. In the invention, it is preferred that the P layer be a layer comprising the compound represented by the formula (I) and at least one hole-transporting material.

As the hole-transporting material, the materials used in the hole-transporting region mentioned above can be used. Among these materials, an aromatic tertiary amine compound is preferable.

The content of the compound represented by the formula (I) in the P layer is 0.1 wt % to 100 wt %, with 10 wt % to 70 wt % being particularly preferable.

The thickness of the P layer is preferably 1 nm to 50 nm, with 5 nm to 20 nm being particularly preferable.

In the invention, it is preferred that at least one of emitting units have a hole-transporting layer, and that the P layer of the charge-generating layer be in contact with the hole-transporting layer. For example, as in the case of an organic EL device 1 shown in FIG. 1, it is preferred that the hole-transporting layer 31B of the second emitting unit 30B be in contact with the P layer 42 of the charge-generating layer. Due to such a configuration, injection of holes from the charge-generating layer to the hole-transporting layer 31B of the second emitting unit 30B can be conducted efficiently, whereby a lowering in driving voltage of the device is realized.

The charge-generating layer may be formed only of two layers, i.e. the N layer and the P layer. An intermediate layer may be provided between the N layer and the P layer.

(Cathode)

As the cathode, one comprising, a metal having a small work function (4 eV or less), an alloy, a conductive material or a mixture thereof is used as the electrode material. Specific examples of the electrode material include, but are not limited to, sodium, sodium-potassium alloys, magnesium, lithium, magnesium-silver alloys, aluminum, aluminum/aluminum oxide, aluminum/lithium alloys, indium, rare earth metals can be given.

The cathode may be formed by forming a thin film of the electrode material by deposition, sputtering, or the like.

When outcoupling light from the emitting layer through the cathode, it is preferable that the cathode have a light transmittance of more than 10%. The sheet resistance of the cathode is preferably several hundred Ω/□ or less. The thickness of the cathode is normally 10 nm to 1 µm, and preferably 50 to 200 nm.

(Other Constitution Elements)

In the invention, between the cathode and the organic layer, an electron-injecting layer formed of an insulator or a semiconductor may be formed. Due to provision of such a layer, leakage of electric current can be effectively prevented, whereby electron-injection property can be improved.

As such an insulator, it is preferable to use at least one metal compound selected from the group consisting of an alkali metal chalcogenide, an alkaline earth metal chalcogenide, a halide of an alkali metal and a halide of an alkaline earth metal. It is preferred that the electron-injecting layer be formed of these alkali metal chalcogenides or the like, since the electron-injecting property can be further improved.

Specifically, as preferable alkali metal chalcogenides, $Li_2O$, LiO, $Na_2S$, $Na_2Se$ and $Na_2O$ can be given. As preferable alkaline earth metal chalcogenides, CaO, BaO, SrO, BeO, BaS and CaSe can be given, for example. As preferable halides of an alkali metal, LiF, NaF, KF, CsF, LiCl, KCl and NaCl can be given, for example. As preferable halides of an alkaline earth metal, a fluoride such as $CaF_2$, $BaF_2$, $SrF_2$, $MgF_2$ and $BeF_2$ and a halide other than a fluoride can be given, for example.

As the semiconductor constituting the electron-injecting layer, an oxide, a nitride or a nitric oxide containing at least one element selected from Ba, Ca, Sr, Yb, Al, Ga, In, Li, Na, Cd, Mg, Si, Ta, Sb and Zn, or the like can be given, for example. They can be used singly or in combination of two or more.

Further, it is preferred that an inorganic compound constituting the electron-injecting layer be a finely-crystallized or amorphous insulating thin film.

As such an inorganic compound, an alkali metal chalcogenide, an alkaline earth metal chalcogenide, a halide of an alkali metal and a halide of an alkaline earth metal or the like can be given, for example.

The structure of the organic EL device of the invention is explained hereinabove by referring to the organic EL device 1 shown in FIG. 1. The invention is not restricted to the organic EL device 1. For example, although two emitting units are formed in the organic EL device 1, three or more emitting units may be formed.

Figure 2:
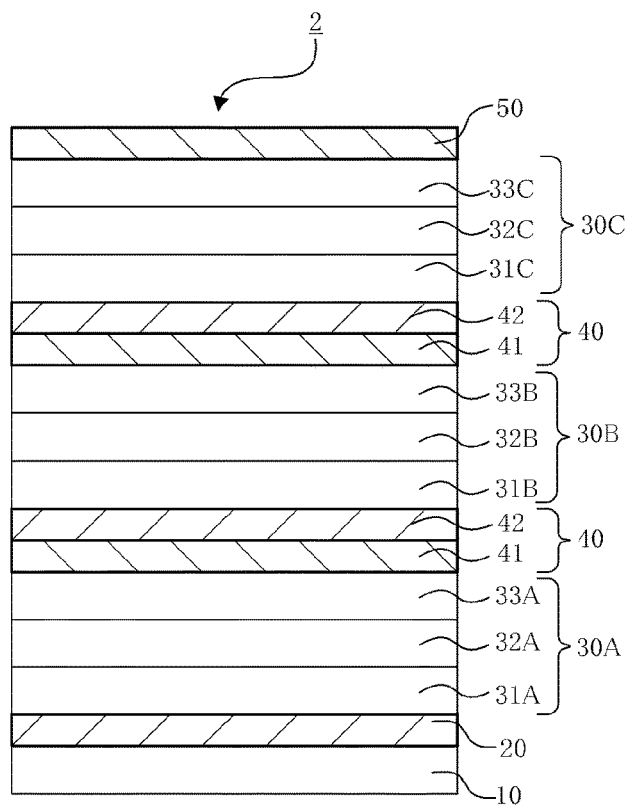
FIG. 2 is a schematic cross-sectional view showing another embodiment of the organic EL device according to the invention.

FIG. 2 is a schematic cross-sectional view of the organic EL device according to the second embodiment of the invention.

In an organic EL device 2, on a substrate 10, an anode 20, a first emitting unit 30A, a charge-generating layer 40, a second emitting unit 30B, a charge-generating layer 42, a third emitting unit 30C and a cathode 50 are provided in this sequence. The organic EL device 2 has the same configuration as the organic EL device 1 shown in FIG. 1, except that three emitting units are provided.

In this embodiment, for example, by allowing the three emitting units to emit different colors of light, i.e. red, green and blue, a white emitting EL device having an excellent color rending property, that is, capable of emitting light of three wavelength regions in a well-harmonized manner is obtained.

The organic EL device of the invention exhibits excellent effects in particular when a plurality of devices are formed on a substrate as in the case of a pixel in a display.

Figure 3:
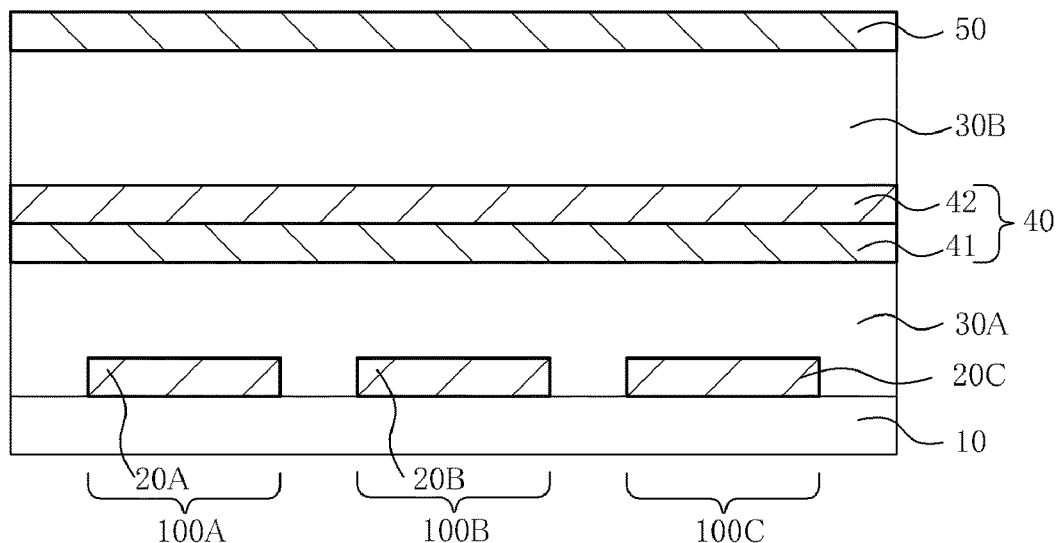
FIG. 3 is a schematic view showing an example in which three organic EL devices are formed on a substrate.

FIG. 3 is a schematic view showing an example in which three organic EL devices are formed on a substrate.

On the substrate 10, the anodes 20A, 20B and 20C that have been patterned in a striped shape are provided. On the substrate 10 and each anode, the first emitting unit 30A, the charge-generating layer 40 and the second emitting unit 30B are formed in this sequence as the common elements. On the second emitting unit 30B, the anode 50 is formed in a striped manner such that it crosses orthogonally with the anode 20.

The organic EL devices A to C emit light when a voltage is applied to the opposing anodes 20A to 20C and the cathode 50. For example, the device B emits light when a voltage is applied between the anode 20B and the cathode 50.

In the case of a device in which conventional materials such as a transparent conductor such as ITO are used in the charge-generating layer, charges are flown to adjacent devices through the charge-generating layer that is formed as the common layer for the devices, and a problem arises that an adjacent device, that is not supposed to emit light, emits light. As a result, luminous efficiency is lowered or color purity is lowered when the device is used in a display.

In the organic EL device of the invention, by using the compound represented by the formula (I) mentioned above in the P layer of the charge-generating layer, leakage of charges to adjacent devices can be suppressed.

The organic EL device of the invention is particularly preferable as an emitting element of a color display utilizing a color filter.

Figure 4:
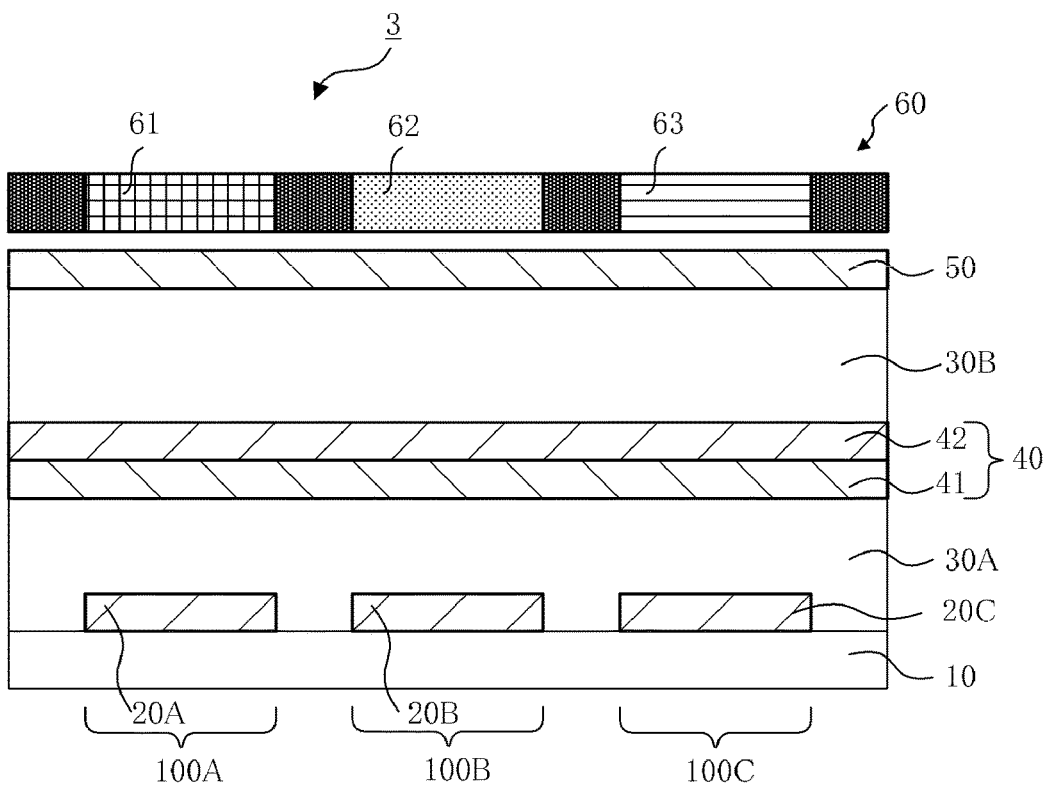
FIG. 4 is a schematic cross-sectional view of a color display using the organic EL device of the invention.

FIG. 4 is a cross-sectional view of a color display using the organic EL device of the invention.

The color display is formed by providing, on the light-outcoupling side of the organic EL device shown in FIG. 3, a color filter 60 having a red color filter (RCF) 61, a green color filter (GCF) 62 and a blue color filter (BCF) 63. In this embodiment, by allowing the emission color of the first emitting unit 30A to be yellow and the emission color of the second emitting unit 30B to be blue, a white color-emitting organic EL device is obtained. By the color filter, from the white color light, only desired light of color is outcoupled outside the display.

As mentioned above, the organic EL device of the invention can suppress leakage of charges to adjacent devices, as mentioned above. That is, since it is possible to suppress unnecessary emission of adjacent devices and to allow only desired devices (pixels) to emit light, color reproducibility of a display can be improved.

The organic EL device of the invention can be fabricated by a known method. Specifically, the anode or the cathode can be formed by a method such as deposition or sputtering. Each of the organic layers of the emitting unit or the like can be formed by the vacuum vapor deposition method, the spin coating method, the casting method, the LB method or the like.

EXAMPLES

[Blue EL Device]

Example 1

A bottom-emission type organic EL device in which emission is outcoupled from the substrate having the layer structure shown in FIG. 1 was fabricated. The structures of the organic compounds used in Example 1 are shown below. The compounds (P1) to (P4), which were compounds used in the P layer of the charge-transporting layer, were synthesized by referring to WO2010/064655 and WO2009/011327.

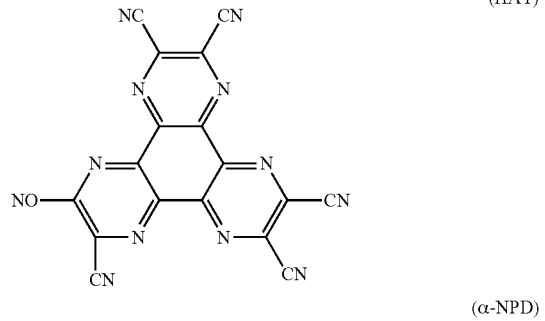
(HAT)

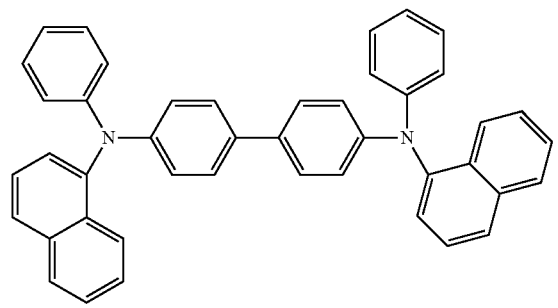
(α-NPD)

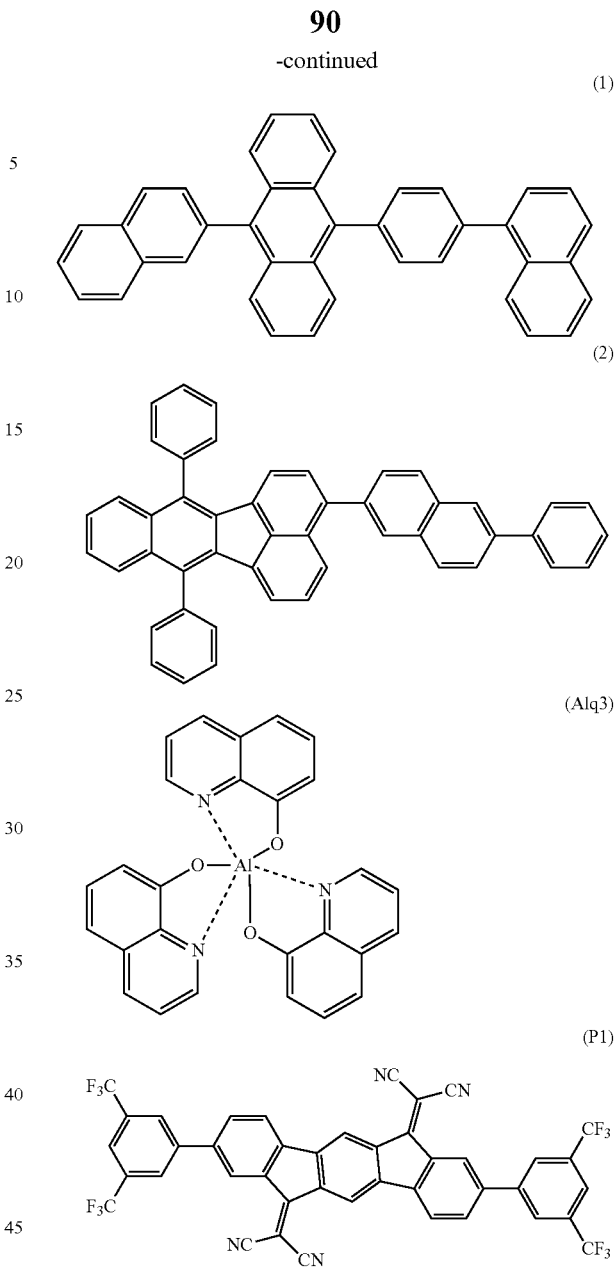

On a glass substrate having a dimension of 30 mm×30 mm, ITO was formed in a thickness of 240 nm as an anode. Subsequently, by deposition of SiO$_2$, a cell for an organic EL device in which other parts than emitting regions of 2 mm×2 mm are masked by an insulating film (not shown) was fabricated.

On the anode, as the hole-injecting layer, hexanitrileaza-triphenylene (HAT) having the above-mentioned structure was formed in a thickness of 10 nm.

On the hole-injecting layer, a blue emitting unit (first emitting unit) formed of a hole-transporting layer, a blue-emitting layer and an electron-transporting layer was formed.

Specifically, as the hole-transporting layer, the above-mentioned α-NPD was formed in a 90 nm-thick film by the vacuum vapor deposition method (deposition speed: 0.2 to 0.4 nm/sec). Subsequently, on the hole-transporting layer, a blue-emitting layer was formed. As the host for the emitting layer, the compound represented by the above formula (1)

was used, and as the dopant for the emitting layer, the compound represented by the above formula (2) was used. Vacuum deposition was conducted such that the amount of the dopant added became 5% in terms of film thickness ratio, whereby an emitting layer having a film thickness of 30 nm was formed.

Subsequently, on the blue-emitting layer, as an electron-transporting layer, Alq3 was formed in a 30 nm-thick film.

Subsequent to the formation of the blue emitting unit, a charge-generating layer was formed.

On the electron-transporting layer of the emitting unit, as the N layer, a mixture layer of Alq3 and Li was formed in a film thickness of 10 nm. Subsequently, as the P layer, the compound represented by the above formula (P1) was formed in a film thickness of 10 nm.

Subsequent to the formation of the charge-generating layer, a second blue-emitting unit was formed. The second blue-emitting unit was formed in the same manner as in the formation of the first blue emitting unit mentioned above.

Thereafter, LiF was formed in a film having a thickness of about 0.3 nm (deposition speed: 0.01 nm/sec) by vapor vacuum deposition, and then, Al was formed in a film having a thickness of 200 nm by the vapor vacuum deposition to form a cathode having a two-layer structure, whereby an organic EL device was fabricated.

Example 2

An organic EL device was fabricated in the same manner as in Example 1, except that a compound represented by the following formula (P2) was used instead of the compound represented by the above formula (P1) as the material for the P layer.

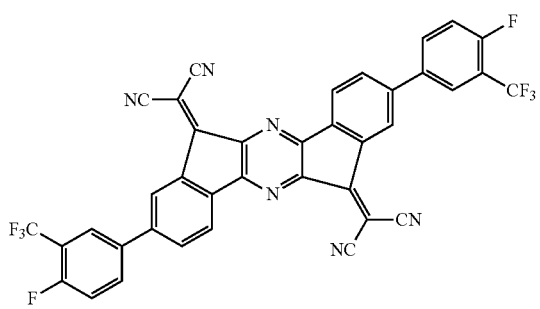

(P2)

Example 3

An organic EL device was fabricated in the same manner as in Example 1, except that a compound represented by the following formula (P3) was used instead of the compound represented by the above formula (P1) as the material for the P layer.

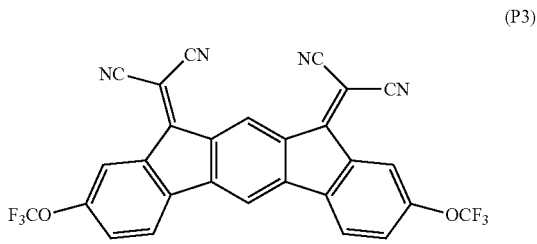 [SMILES: N#CC(C#N)=C1c2cc(OC(F)(F)F)ccc2-c2cc3c(cc21)C(=C(C#N)C#N)c1cc(OC(F)(F)F)ccc1-3]

(P3)

Examples 4 to 6

Organic EL devices were fabricated in the same manner as in Examples 1 to 3, except that a compound represented by the following formula (9-23) was used instead of Alq3 as the material for the N layer.

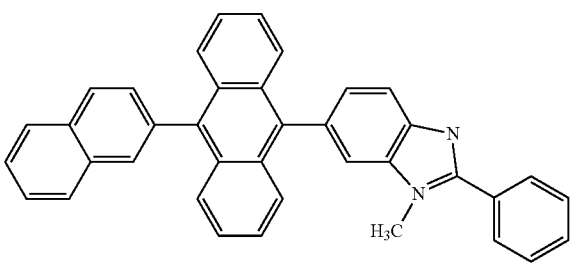

(9-23)

Comparative Example 1

An organic EL device was fabricated in the same manner as in Example 1, except that the cathode was formed without forming the charge-generating layer and the second blue emitting unit. The device of this embodiment is a device having only one emitting unit, and hence, it is not a tandem-type organic EL device.

Comparative Example 2

An organic EL device was fabricated in the same manner as in Example 1, except that the P layer as the charge-generating layer was not formed.

Comparative Example 3

An organic EL device was fabricated in the same manner as in Example 1, except that molybdenum oxide ($MoO_3$) was used instead of the compound represented by the above formula (P1) as the material for the P layer.

For the organic EL devices fabricated in Examples 1 to 6 and Comparative Examples 1 to 3, the voltage (V) and the luminous efficiency (cd/A) at a current density of 10 mA $cm^{-2}$ were measured. The results are shown in Table 1.

TABLE 1

| | Emission color of first emitting unit | Constitution of charge-generating layer | | | Emission color of second emitting unit | Emission color of entire device | Luminance cd/m² | Voltage V |
|---|---|---|---|---|---|---|---|---|
| | | N layer | P layer | Thickness of P layer nm | | | | |
| Ex. 1 | Blue | Alq3 + Li | P1 | 10 | Blue | Blue | 1620 | 10.1 |
| Ex. 2 | Blue | Alq3 + Li | P2 | 10 | Blue | Blue | 1630 | 10.2 |
| Ex. 3 | Blue | Alq3 + Li | P3 | 10 | Blue | Blue | 1600 | 10 |
| Ex. 4 | Blue | 9-23 + Li | P1 | 10 | Blue | Blue | 1650 | 8.2 |
| Ex. 5 | Blue | 9-23 + Li | P2 | 10 | Blue | Blue | 1585 | 8.2 |
| Ex. 6 | Blue | 9-23 + Li | P3 | 10 | Blue | Blue | 1630 | 8.2 |
| Com. Ex. 1 | Blue | — | — | — | — | Blue | 810 | 4.8 |
| Com. Ex. 2 | Blue | Alq3 + Li | — | — | Blue | Blue | 760 | 6.1 |
| Com. Ex. 3 | Blue | Alq3 + Li | MoO₃ | 10 | Blue | Blue | 1580 | 13.9 |

From the results of Examples 1 to 3 and Comparative Example 1, it was revealed that, by fabricating a tandem device utilizing the charge-generating layers comprising the above compounds (P1) to (P3), an efficiency that was twice as large as that of a single unit device was obtained, and the voltage also doubled. As a result, it has been confirmed that the tandem device utilizing the charge-generating layer comprising the compounds (P1) to (P3) functioned as a MPE device.

From the results of Examples 1 to 3 and Comparative Example 2, it was revealed that, in the charge-generating layer, if a layer comprising the compound (P1) to (P3) is not provided at the interface between the emitting unit on the cathode side, the efficiency thereof was as poor as that of Comparative Example 1 (single unit device), and hence it did not function as a MPE device.

From the results of Examples 1 to 3 and Comparative Example 3, in the charge-generating layer, if MoO₃ was used in a layer at the interface between the emitting unit on the cathode, although the device functioned as a MPE device, the driving voltage thereof was higher than that in Examples 1 to 3. As a result, it was confirmed that the compounds (P1) to (P3) were excellent as the charge-generating layers.

Further, it was confirmed that, in Examples 4 to 6 in which the compound represented by the formula (9-23) (nitrogen-containing heterocyclic compound) was used in the N layer, the driving voltage was further decreased.

[White-Emitting EL Device]

Example 7

An organic EL device was fabricated in the same manner as Example 1, except that a glass substrate in which a lower electrode was patterned so that the resolution became 100 ppi was used and the following yellow emitting unit was formed instead of the first blue emitting unit.

Fabrication of a Patterned Electrode Substrate

On a glass substrate, a planarized insulating film was formed. No specific restrictions are imposed on the planarized insulating film material as long as it is a positive-photoresist type insulating material. In this example, polyimide was formed in a thickness of 2.0 μm. Specifically, on the substrate, polyimide was applied by a spin-coating method, exposed by an exposing apparatus, developed by means of a paddle developer, and patterned in a desired shape. In order to cure the polyimide, calcination was conducted in a clean baking furnace, whereby a 2.0 μm-thick planarized insulating film was formed.

Subsequently, lower electrodes were formed on the planarized insulating film. Specifically, ITO was formed on the planarized insulating film in a thickness of 240 nm, and patterned into a prescribed shape by using a common lithography technology, followed by etching to form lower electrodes.

Between the patterned lower electrodes (ITO), polyimide was formed in a thickness of 2.0 μm, whereby an insulating layer between electrodes was formed. Specifically, the insulating layer between electrodes was formed as follows. On the substrate, polyimide was applied by a spin-coating method, exposed by an exposing apparatus, developed by means of a paddle developer, whereby the polyimide as the photosensitive insulating material was patterned into a desired shape. Subsequently, in order to cure the polyimide, calcination was conducted in a clean baking furnace, whereby an insulating layer between electrodes was formed.

Formation of a Yellow Emitting Unit

On the hole-injecting layer comprising the above-mentioned hexanitrileazatriphenylene (HAT), a yellow emitting unit comprising the hole-transporting layer, a yellow emitting layer and the electron-transporting layer (first emitting unit) was formed.

As the hole-transporting layer, the α-NPD mentioned above was formed in a 30 nm-thick film by the vacuum vapor deposition method (deposition speed: 0.2 to 0.4 nm/sec).

Subsequently, on the hole-transporting layer, a yellow-emitting layer was formed. As the host for the emitting layer and as the dopant for the emitting layer, a compound represented by the following formula (3) and a compound represented by the following formula (4) were respectively used. The compounds were vacuum-vapor-deposited such that the amount of the dopant added became 5% in terms of a thickness ratio, whereby an emitting layer having a thickness of 30 nm was formed.

Subsequently, on the yellow emitting layer, as an electron-transporting layer, Alq3 was formed in a 20 nm-thick film.

Hereinbelow, a charge-generating layer and a second emitting unit were formed in the same manner as in Example 1, whereby an organic EL device was fabricated.

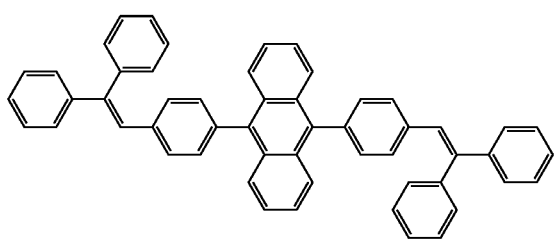

(3)

(4)

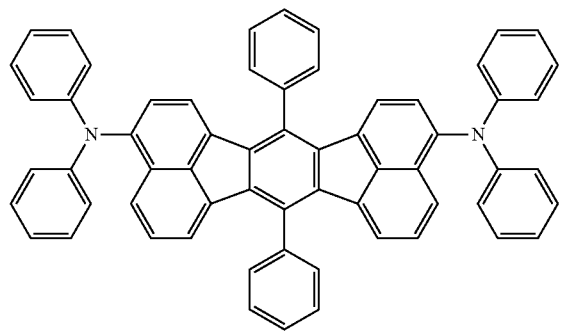

(P4)

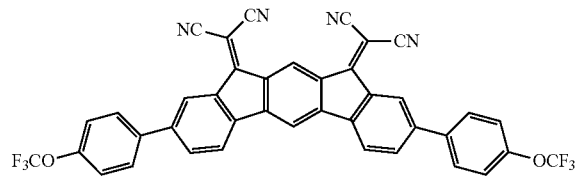

Example 8

An organic EL device was fabricated in the same manner as in Example 7, except that the compound represented by the formula (P2) used in Example 2 was used as the material for the P layer instead of the compound represented by the above formula (P1).

Example 9

An organic EL device was fabricated in the same manner as in Example 7, except that the compound represented by the formula (P3) used in Example 3 was used as the material for the P layer instead of the compound represented by the above formula (P1).

Example 10

An organic EL device was fabricated in the same manner as in Example 7, except that a layer of a mixture of the compound represented by the formula (P1) and α-NPD [(P1: α-NPD=1:1, weight ratio)] was used as the P layer instead of the compound represented by the above formula (P1).

Example 11

An organic EL device was fabricated in the same manner as in Example 7, except that a stacked body of a layer of the compound represented by the above formula (P1) and the layer of a mixture of the compound represented by the formula (P1) and the α-NPD [(P1: α-NPD=1:1, weight ratio)] was used as the P layer instead of the single layer of the compound represented by the above formula (P1). The thickness of the (P1) single layer was 5 nm and the thickness of the mixture layer of the compound represented by the formula (P1) and the α-NPD was 5 nm.

Example 12

An organic EL device was fabricated in the same manner as in Example 7, except that the compound represented by the following formula (P4) was used as the material for the P layer instead of the compound represented by the above formula (P1).

Examples 13 to 15

Organic EL devices were fabricated in the same manner as in Examples 7 to 9, except that a compound represented by the formula (9-23) was used as the material for the N layer instead of Alq3.

Comparative Example 4

An organic EL device was fabricated in the same manner as in Example 4, except that the cathode was formed without forming the charge-generating layer and the second blue emitting unit. The device of this embodiment is a device having only one emitting unit, and hence, it is not a tandem-type organic EL device.

Comparative Example 5

An organic EL device was fabricated in the same manner as in Example 7, except that the P layer of the charge-generating layer was not formed.

Comparative Example 6

An organic EL device was fabricated in the same manner as in Example 7, except that the HAT shown below was used as the material for the P layer instead of the compound represented by the above formula (P1).

Comparative Example 7

An organic EL device was fabricated in the same manner as in Example 7, except that ITO was used as the material for the P layer instead of the compound represented by the above formula (P1).

For the organic EL devices fabricated in Examples 7 to 15 and Comparative Examples 4 to 7, the voltage (V) and the luminous efficiency (cd/A) at a current density of 10 mA $cm^{-2}$ were measured. Further, the CIE chromaticity of emission was measured by means of a spectroradiometer.

The results are shown in Table 2.

In each pixel of the organic EL device fabricated in Examples 7 to 15 and Comparative Examples 4 to 7, a red color filter, a green color filter and a blue color filter were formed. Color reproducibility encompassed by each of red, green and blue colors was evaluated in terms of NTSC ratio. An organic EL device was fabricated as follows.

At positions that serve as openings of a glass substrate, color filters of each of RGB were formed in sequence. On the color filters, a planarized insulating film was formed in the same manner as in Example 7, whereby unevenness in the color filters was removed to be flat. As a result, a glass substrate having color filters was obtained. Thereafter, a patterned electrode substrate was fabricated in the same manner as in Example 7, whereby an emitting unit was further formed.

In order to enable the thus fabricated device to be driven in a passive-type manner, a lower electrode and an upper electrode were provided, and each pixel of RGB was enabled to emit light individually. As a result, emission of a single color of each of RGB becomes possible.

Figure 5:
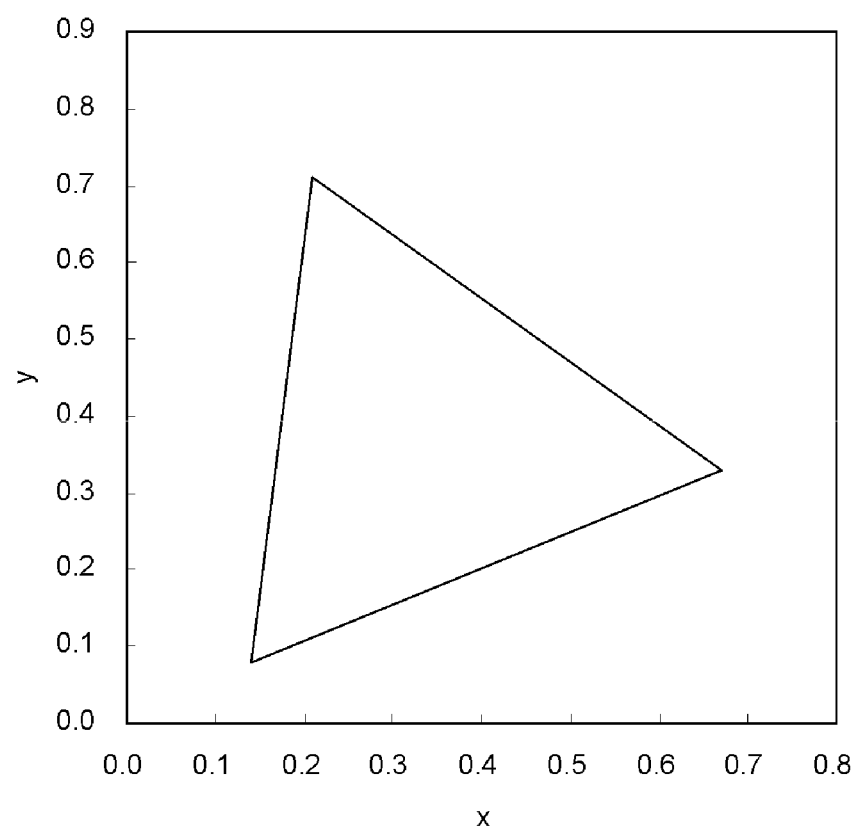
FIG. 5 is a view showing a region obtained by connecting chromaticity coordinates of red, green and blue determined by NTSC in the CIE XYZ color space.

Here, the NTSC ratio means the ratio (unit:%) of color reproduction range of a display relative to the area surrounded by the three primary colors of the NTSC (National Television System Committee (NTSC) of the Americas) standard; red (0.670, 0.330), green (0.210, 0.710) and blue (0.140, 0.080). FIG. 5 shows the region obtained by connecting chromaticity coordinates of red, green and blue determined by the NTSC in the CIE-XYZ color diagram. This region is taken as 100%.

The results are shown in Table 2.

cent pixels to emit light. As a result, when red, green or blue color was displayed as a single color, the purity of each color was deteriorated.

From the above, in a stacked type white device, by using a layer comprising the above-mentioned compounds (P1) to (P4) in the charge-generating layer, an organic EL display panel suffering less color mixing and having excellent color reproducibility can be fabricated.

In Examples 10 and 11, both the yellow emitting unit and the blue emitting unit emitted light, white emission as that obtained in Example 7 was obtained. From this result, it was confirmed that a tandem device using a layer of a mixture of the compound (P1) and the α-NPD or a stacked body of a layer of the compound (P1) and a layer of a mixture of the compound (P1) and the α-NPD as a charge-generating layer

TABLE 2

| | Emission color of first emitting unit | Constitution of charge-generating layer | | Thickness of P layer nm | Emission color of second emitting unit | Emission color of entire device | Luminance (cd/m$^2$) | Chromaticity coordinates (x, y) | Voltage (V) | NTSC ratio (%) |
|---|---|---|---|---|---|---|---|---|---|---|
| | | N layer | P layer | | | | | | | |
| Ex. 7 | Yellow | Alq3 + Li | P1 | 10 | Blue | White | 4060 | (0.246, 0.331) | 10 | 100 |
| Ex. 8 | Yellow | Alq3 + Li | P2 | 10 | Blue | White | 4080 | (0.246, 0.332) | 10.1 | 100 |
| Ex. 9 | Yellow | Alq3 + Li | P3 | 10 | Blue | White | 4050 | (0.246, 0.330) | 9.9 | 100 |
| Ex. 10 | Yellow | Alq3 + Li | P1 + α-NPD | 10 | Blue | White | 4050 | (0.246, 0.332) | 10.1 | 100 |
| Ex. 11 | Yellow | Alq3 + Li | P1/P1 + α-NPD | 10 | Blue | White | 4080 | (0.245, 0.331) | 9.8 | 100 |
| Ex. 12 | Yellow | Alq3 + Li | P4 | 10 | Blue | White | 4070 | (0.246, 0.331) | 9.9 | 100 |
| Ex. 13 | Yellow | 9-23 + Li | P1 | 10 | Blue | White | 4320 | (0.246, 0.331) | 7.8 | 94 |
| Ex. 14 | Yellow | 9-23 + Li | P2 | 10 | Blue | White | 4250 | (0.246, 0.330) | 7.9 | 93 |
| Ex. 15 | Yellow | 9-23 + Li | P3 | 10 | Blue | White | 4130 | (0.246, 0.330) | 7.9 | 93 |
| Com. Ex. 4 | Yellow | — | — | — | — | Yellow | 2970 | (0.356, 0.607) | 5.2 | 30 |
| Com. Ex. 5 | Yellow | Alq3 + Li | — | — | Blue | White | 3110 | (0.355, 0.608) | 5.1 | 40 |
| Com. Ex. 6 | Yellow | Alq3 + Li | HAT | 10 | Blue | White | 4120 | (0.246, 0.330) | 9.9 | 80 |
| Com. Ex. 7 | Yellow | Alq3 + Li | ITO | 10 | Blue | White | 3910 | (0.247, 0.332) | 13.2 | 60 |

From the results of Examples 7 to 9 and 12 and Comparative Examples 1 and 4, it was confirmed that, by fabricating a tandem device utilizing the charge-generating layer comprising the compounds (P1) to (P4) mentioned above, the synergistic effect of the yellow single unit device and the blue single unit device could be obtained, whereby white emission was obtained.

From the results of Examples 7 to 9 and 12 and Comparative Example 5, it was revealed that, in the charge-generating layer, if a layer comprising the above compounds (P1) to (P4) was not provided at the interface between the emitting unit on the cathode side, only the yellow unit as the first emitting unit on the cathode side emitted light, and the device did not function as an MPE device.

From the results of Examples 7 to 9 and 12 and Comparative Examples 6 and 7, it was revealed that, in the charge-generating layer, if HAT or ITO was used in a layer at the interface between the emitting unit on the cathode side, although the device functioned as an MPE device, as compared with Example 4, when a display panel was produced by providing a color filter, the NTSC ratio was lowered in respect of color reproducibility. The reason therefor is assumed to be as follows. Since the resistances of the HAT and ITO were too low, carriers leaked to adjacent pixels through the charge-generating layer, causing the adjafunctioned as a MPE device, thereby proving that fabrication of a stacked type white emission device is possible. Further, in respect of color reproducibility, the NTSC ratio when a display panel was fabricated by providing a color filter was excellent. That means that current leakage to adjacent pixels is suppressed as compared with conventional charge-generating layer structure, whereby a high degree of color reproducibility can be attained.

It was confirmed that, in Examples 13-15 where the compound represented by the formula (9-23) as the nitrogen-containing heterocyclic compound was used in the N layer, the driving voltage was further lowered.

Examples 16 to 19 and Comparative Examples 8 and 9

Organic EL devices were fabricated and evaluated in the same manner as in Examples 7 to 9 and Comparative Examples 6 and 7, except that the thickness of the P layer was changed to 30 nm.

As Example 19, the same device as that in Example 13 was fabricated by using the compound (P4) as the material for the P layer. The results obtained are shown in Table 3.

TABLE 3

| | Emission color of first emitting unit | Constitution of charge-generating layer | | Thickness of P layer nm | Emission color of second emitting unit | Emission color of entire device | Chromaticity coordinates (x, y) | Voltage (V) | NTSC ratio (%) |
|---|---|---|---|---|---|---|---|---|---|
| | | N layer | P layer | | | | | | |
| Ex. 16 | Yellow | Alq3 + Li | P1 | 30 | Blue | White | (0.244, 0.330) | 10.8 | 100 |
| Ex. 17 | Yellow | Alq3 + Li | P2 | 30 | Blue | White | (0.244, 0.331) | 10.9 | 100 |
| Ex. 18 | Yellow | Alq3 + Li | P3 | 30 | Blue | White | (0.244, 0.330) | 10.7 | 100 |
| Ex. 19 | Yellow | Alq3 + Li | P4 | 30 | Blue | White | (0.244, 0.330) | 10.9 | 100 |
| Com. Ex. 8 | Yellow | Alq3 + Li | HAT | 30 | Blue | White | (0.245, 0.331) | 10.7 | 70 |
| Com. Ex. 9 | Yellow | Alq3 + Li | MoO3 | 30 | Blue | White | (0.246, 0.332) | 15.1 | 50 |

From the results of Examples 16 to 19 and Comparative Examples 8 and 9, in a thickness of 30 nm, when a layer at the interface between the emitting unit on the cathode side of the charge-generating layer was a layer containing the above-mentioned compounds (P1) to (P4), a high NTSC ratio was exhibited when a display panel was fabricated by providing a color filter. Therefore, it can be confirmed that color reproducibility was retained. When the layer at the interface was a layer that contained HAT and MoO3, the NTSC ratio was significantly decreased, leading to lowering of color reproducibility. The reason therefor is as follows. When the thickness of the charge-generating layer is large, effects of current leakage to adjacent pixels through the charge-generating layer are significant, and color mixing caused by emission of adjacent pixels becomes significant, whereby significant lowering of color reproducibility is caused.

In addition, although an increase in driving voltage was observed in MoO3, a significant increase in driving voltage cannot be observed when using the above-mentioned compounds (P1) to (P4). Therefore, it can be understood that the excellent characteristics as the charge-generating layer can be obtained when the film thickness is rendered small.

Examples 20 to 23 and Comparative Examples 10 and 11

Organic EL devices were fabricated in the same manner as in Examples 7 to 9 and Comparative Examples 6 and 7, except that the resolution was changed to 1,000 ppi.

As Example 23, the same device as that in Example 20 was fabricated by using the compound (P4) as the material for the P layer. The results are shown in Table 4.

TABLE 4

| | Emission color of first emitting unit | Constitution of charge-generating layer | | Thickness of P layer nm | Emission color of second emitting unit | Emission color of entire device | Chromaticity coordinates (x, y) | NTSC ratio (%) |
|---|---|---|---|---|---|---|---|---|
| | | N layer | P layer | | | | | |
| Ex. 20 | Yellow | Alq3 + Li | P1 | 10 | Blue | White | (0.246, 0.331) | 100 |
| Ex. 21 | Yellow | Alq3 + Li | P2 | 10 | Blue | White | (0.246, 0.332) | 100 |
| Ex. 22 | Yellow | Alq3 + Li | P3 | 10 | Blue | White | (0.246, 0.331) | 100 |
| Ex. 23 | Yellow | Alq3 + Li | P4 | 10 | Blue | White | (0.246, 0.332) | 100 |
| Com. Ex. 10 | Yellow | Alq3 + Li | HAT | 10 | Blue | White | (0.245, 0.330) | 70 |
| Com. Ex. 11 | Yellow | Alq3 + Li | MoO3 | 10 | Blue | White | (0.246, 0.332) | 50 |

From the results of Examples 20 to 23 and Comparative Examples 10 and 11, when a display panel having a higher resolution was fabricated by providing a color filter, if the compound (P1) mentioned above was used in a layer at the interface between the emitting unit on the cathode side of the charge-generating layer, a high NTSC ratio was obtained, whereby a high color reproducibility was retained. On the other hand, when HAT and MoO3 are used in the layer at the interface, the NTSC ratio was significantly decreased, leading to lowering in color reproducibility. The reason therefor is that, if the resolution is high, the distance between pixels becomes short, thereby causing current to be leaked to adjacent pixels through the charge-generating layer, and leading to further significant color mixing by emission of adjacent pixels.

INDUSTRIAL APPLICABILITY

The organic EL device of the invention can be used in a planar luminous body such as a flat panel display of a wall-hanging TV, a copier, a printer, a backlight of a crystal liquid display, or a light source of instruments, a displaying board, sign lighting or the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification of a Japanese application on the basis of which the present application claims Paris convention priority are incorporated herein by reference in its entirety.

The invention claimed is:

1. A substrate comprising two or more adjacent organic electroluminescence devices, each organic electroluminescence device comprising:

an anode;

a cathode;

two or more emitting units that are disposed between the anode and the cathode, each unit having an emitting layer; and a charge-generating layer that is disposed between the emitting units, wherein the charge-generating layer comprises an N layer nearer to the anode and a P layer nearer to the cathode, and the P layer comprises a compound represented by the following formula (I):

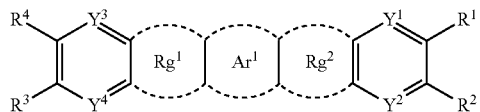
(I)

wherein in the formula (I),

Ar$^1$ is an aromatic ring including 6 to 24 ring carbon atoms, or a heterocyclic ring including 5 to 24 ring atoms, and Rg$^1$ and Rg$^2$ may be the same or different from each other and are represented by the following formula (i) or (ii):

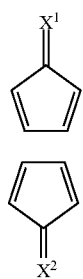

(i)

(ii)

wherein X$^1$ and X$^2$ may be the same or different from each other and are represented by any one of divalent groups represented by the following (a) to (g):

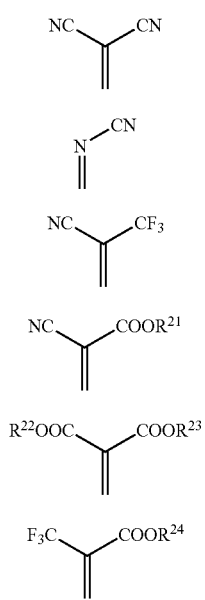

(a)

(b)

(c)

(d)

(e)

(f)

-continued

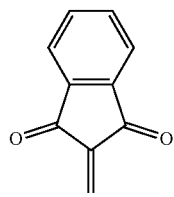
(g)

wherein R$^{21}$ to R$^{24}$ may be the same or different from each other, and are a hydrogen atom, a substituted or unsubstituted fluoroalkyl group, a substituted or unsubstituted alkyl group, a substituted or unsubstituted aryl group or a substituted or unsubstituted heterocyclic group, and R$^{22}$ and R$^{23}$ may be bonded to each other to form a ring;

R$^1$ to R$^4$ may be the same or different from each other, and a hydrogen atom, a substituted orunsubstituted alkyl group, a substituted or unsubstituted cycloalkyl group, a substituted or unsubstituted alkenyl group, a substituted or unsubstituted aryl group, a substituted or unsubstituted heterocyclic group, a halogen atom, a substituted or unsubstituted fluoroalkyl group, a substituted or unsubstituted alkoxy group, a substituted or unsubstituted fluoroalkoxy group, a substituted or unsubstituted aryloxy group, a substituted or unsubstituted aralkyloxy group, a substituted or unsubstituted amino group, a substituted or unsubstituted silyl group, or a cyano group;

R$^1$ and R$^2$ may be bonded to each other to form a ring and R$^3$ and R$^4$ may be bonded to each other to form a ring; and Y$^1$ to Y$^4$ may be the same or different from each other, and are —N=, —CH=, or C(R$^5$)=, R$^5$ is the same as R$^1$ to R$^4$, and adjacent groups of R$^1$ to R$^5$ may be bonded to each other to form a ring, wherein the charge-generating layer are common among the organic electroluminescence device, and each organic electroluminescence device comprises a color filter.

2. The substrate according to claim 1, wherein at least one of the emitting units comprises a hole-transporting layer, and the P layer of the charge-generating layer is contacted with the hole-transporting layer.

3. The substrate according to claim 1, wherein the N layer of the charge-generating layer comprises at least one selected from the group consisting of an electron-donating metal, an electron-donating metal compound and an electron-donating metal complex.

4. The substrate according to claim 3, wherein the N layer of the charge-generating layer comprises at least one selected from the group consisting_of an alkali metal, an alkali metal compound, an alkali metal-containing organic metal complex, an alkaline-earth metal, an alkaline-earth metal compound, an alkaline-earth metal-containing organic metal complex, a rare-earth metal, a rare-earth metal compound and a rare-earth metal-containing organic metal complex.

5. The substrate according to claim 1, wherein the N layer of the charge-generating layer comprises a nitrogen-containing heterocyclic compound.

6. The substrate according to claim 5, wherein the nitrogen-containing heterocyclic compound is represented by the following formula (9):

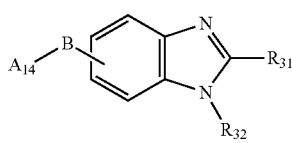
(9)

wherein, $A_{14}$ is a hydrogen atom, a halogen atom, a substituted or unsubstituted alkyl group including 1 to 20 carbon atoms, a substituted or unsubstituted hydrocarbon group including 6 to 60 carbon atoms that comprises a polycyclic aromatic hydrocarbon group formed by 3 to 40 aromatic rings being fused, or a nitrogen-containing heterocyclic group, B is a single bond, or a substituted or unsubstituted aromatic ring group, $R_{31}$ and $R_{32}$ are independently a hydrogen atom, a halogen atom, a substituted or unsubstituted alkyl group including 1 to 20 carbon atoms, a substituted or unsubstituted aromatic hydrocarbon group including 6 to 60 carbon atoms, a substituted or unsubstituted nitrogen-containing heterocyclic group, or a substituted or unsubstituted alkoxy group including 1 to 20 carbon atoms.

7. The substrate according to claim 1, wherein a material constituting the emitting layer(s) of at least one of the emitting units is different from a material constituting the emitting layer(s) of other emitting unit(s).

8. The substrate according to claim 1, wherein at least one of the emitting units comprises a hole-transporting region, and the P layer of the charge-generating region is contacted with the hole-transporting region.

9. The substrate according to claim 8, wherein the hole-transporting region comprises an aromatic amine derivative represented by the following formula (4):

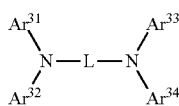
(4)

wherein $Ar^{31}$ to $Ar^{34}$ are an aromatic hydrocarbon group including 6 to 50 ring carbon atoms that may have a substituent, a fused aromatic hydrocarbon group including 6 to 50 ring carbon atoms that may have a substituent, an aromatic heterocyclic group including 2 to 40 ring carbon atoms that may have a substituent, a fused aromatic heterocyclic group including 2 to 40 ring carbon atoms that may have a substituent, a group formed by bonding of the aromatic hydrocarbon group with the aromatic heterocyclic group, a group formed by bonding of the aromatic hydrocarbon group with the fused aromatic heterocyclic group, a group formed by bonding of the fused aromatic hydrocarbon group with the aromatic heterocyclic group, or a group formed by bonding of the fused aromatic hydrocarbon group with the fused aromatic heterocyclic group; and L is a single bond, an aromatic hydrocarbon group including 6 to 50 ring carbon atoms that may have a substituent, a fused aromatic hydrocarbon group including 6 to 50 ring carbon atoms that may have a substituent, an aromatic heterocyclic group including 2 to 40 ring carbon atoms that may have a substituent, a fused aromatic heterocyclic group including 2 to 40 ring carbon atoms that may have a substituent, a group formed by bonding of the aromatic hydrocarbon group with the aromatic heterocyclic group, a group formed by bonding of the aromatic hydrocarbon group with the fused aromatic heterocyclic group, a group formed by bonding of the fused aromatic hydrocarbon group with the aromatic heterocyclic group, or a. group formed by bonding of the fused aromatic hydrocarbon group with the fused aromatic heterocyclic group.

10. The substrate according to claim 8, wherein the hole-transporting region comprises an aromatic amine derivative represented by the following formula (5):

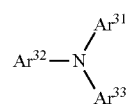
(5)

wherein $Ar^{31}$ to $Ar^{33}$ are an aromatic hydrocarbon group including 6 to 50 ring carbon atoms that may have a substituent, a fused aromatic hydrocarbon group including 6 to 50 ring carbon atoms that may have a substituent, an aromatic heterocyclic group including 2 to 40 ring carbon atoms that may have a substituent, a fused aromatic heterocyclic group including 2 to 40 ring carbon atoms that may have a substituent, a group formed by bonding of the aromatic hydrocarbon group with the aromatic heterocyclic group, a group formed by bonding of the aromatic hydrocarbon group with the fused aromatic heterocyclic group, a group formed by bonding of the fused aromatic hydrocarbon group with the aromatic heterocyclic group, or a group formed by bonding of the fused aromatic hydrocarbon group with the fused aromatic heterocyclic group.

11. The substrate according to claim I, wherein the compound represented by the formula (I) is a compound represented by the following formula (I-A) or (I-B):

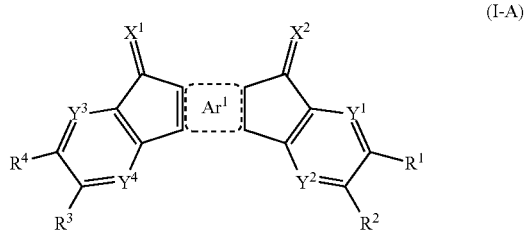
(I-A)

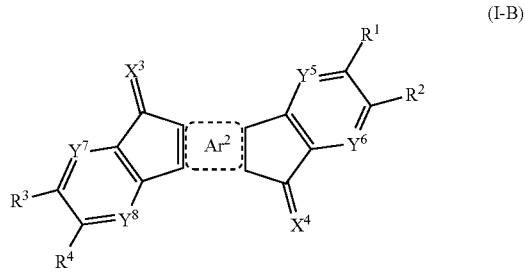
(I-B)

wherein in the formula (I-A), $Ar^1$, $X^1$, $X^2$, $R^1$ to $R^4$, and $Y^1$ to $Y^4$ are the same as $Ar^1$, $X^1$, $X^2$, $R^1$ to $R^4$, and $Y^1$ to $Y^4$ in the formula (I): and in the formula (I-B) $Ar^2$ is the same as $Ar^1$ in the formula (I), $X^3$ and $X^4$ are the same as $X^1$ and $X^2$ in the formula (I), $Y^5$ to $Y^8$ are the same as $Y^1$ to $Y^4$ in the formula (I) and $R^1$ to $R^4$ are the same as $R^1$ to $R^4$ in the formula (I).

12. The substrate according to claim 1, wherein the compound represented by the formula (I) is a compound represented by any one of the following formulas (II) to (X):

(II)
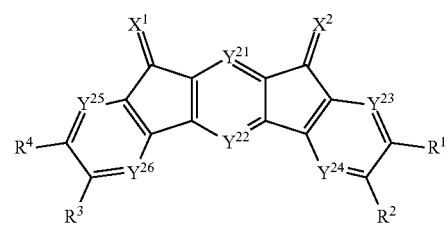

(III)
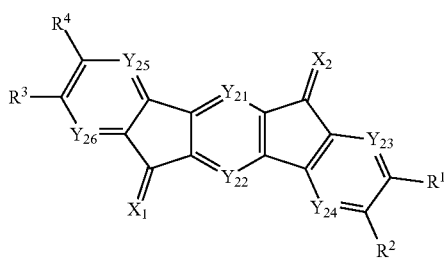

(IV)
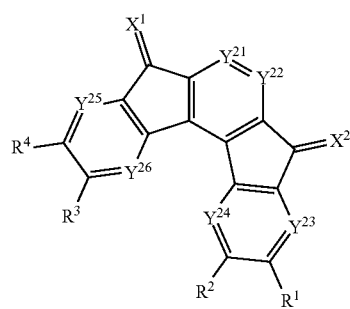

(V)
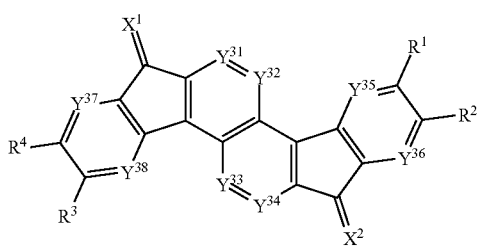

(VI)
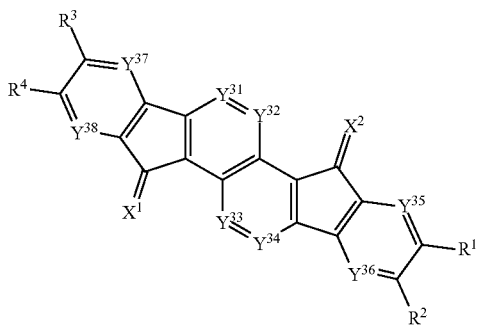

(VII)
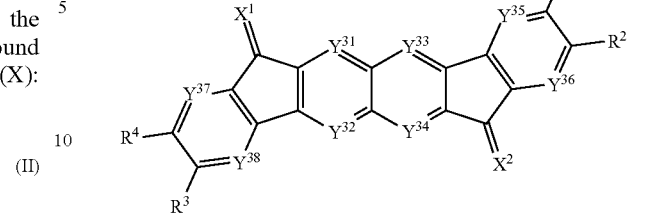

(VIII)
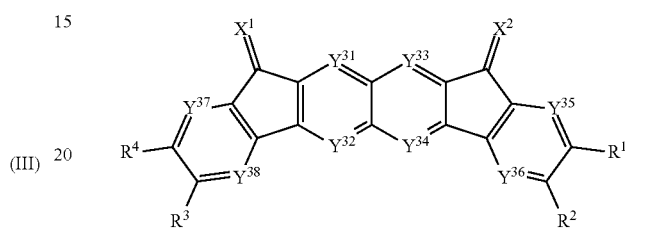

(IX)
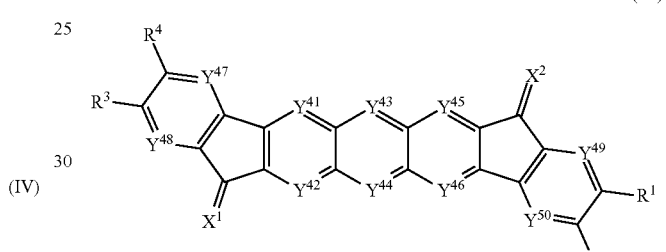

(X)
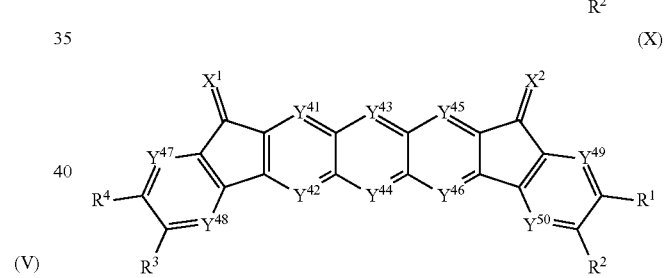

wherein $X^1$, $X^2$ and $R^1$ to $R^4$ are the same as $X^1$, $X^2$ and $R^1$ to $R^4$ in the formula (I): and $Y^{21}$ to $Y^{26}$, $Y^{31}$ to $Y^{38}$ and $Y^{41}$ to $Y^{50}$ are the same as $Y^1$ to $Y^4$ in the formula (I).

13. The substrate according to claim 1, wherein the compound represented by the formula (I) is a compound represented by any one of the following formulas (I-a) to (I-r):

(I-a)
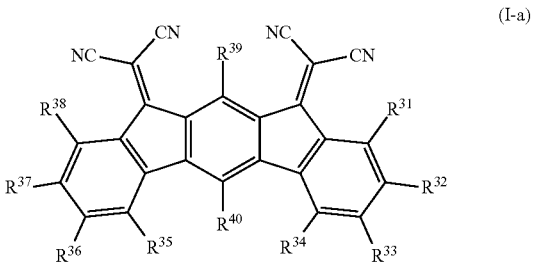

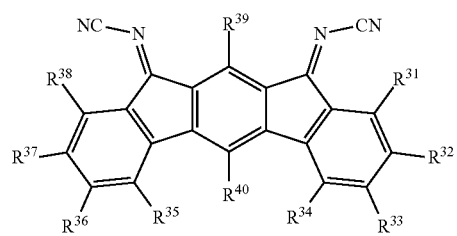 (I-b)
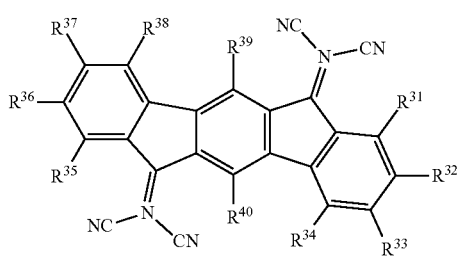 (I-c)
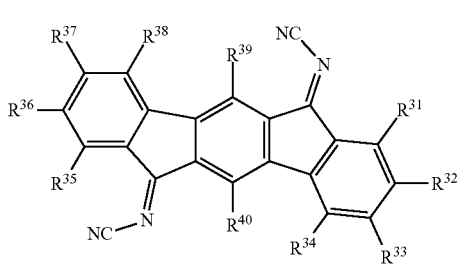 (I-d)
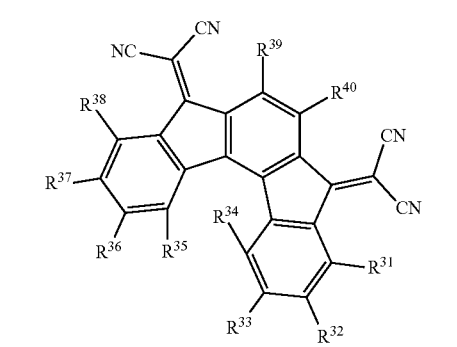 (I-e)
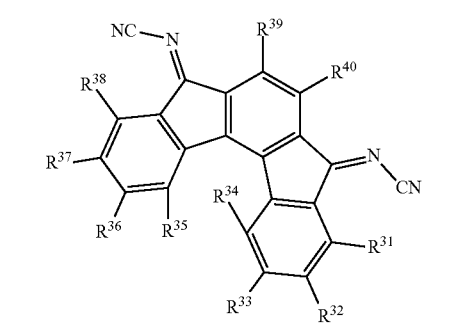 (I-f)
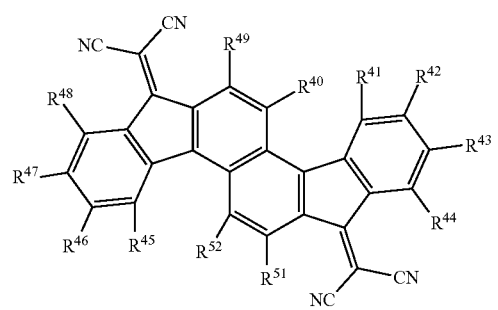 (I-g)
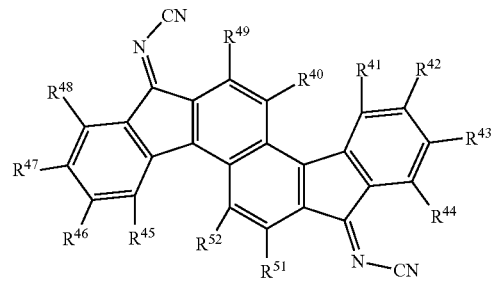 (I-h)
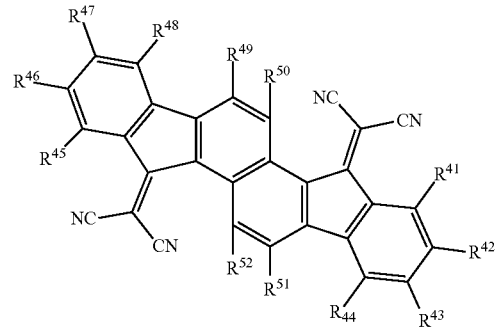 (I-i)
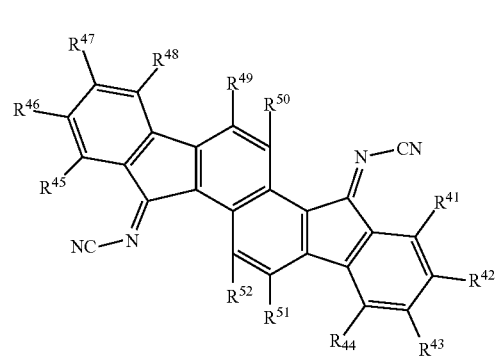 (I-j)
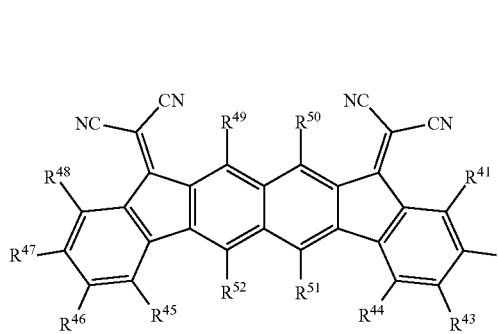 (I-k)

(I-l)

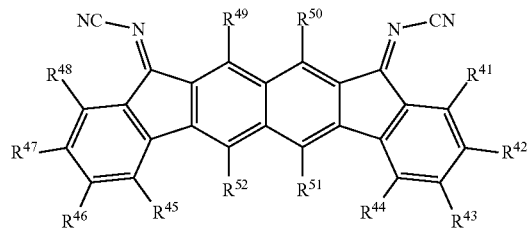

(I-m)

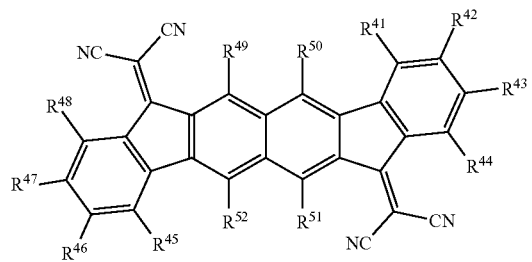

(I-n)

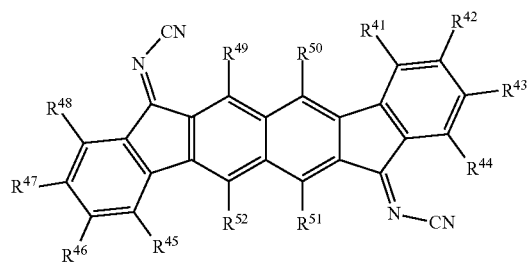

(I-o)

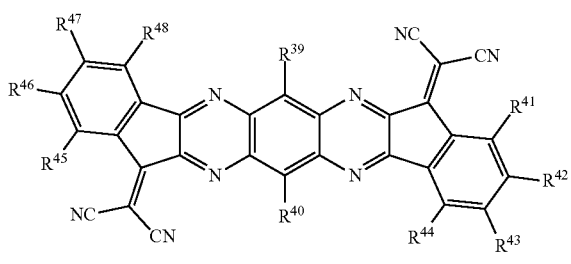

(I-p)

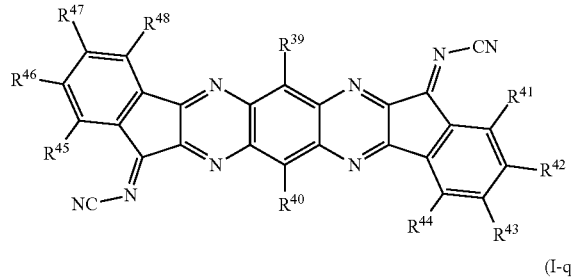

(I-q)

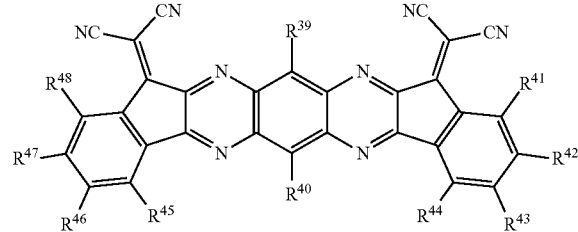

(I-r)

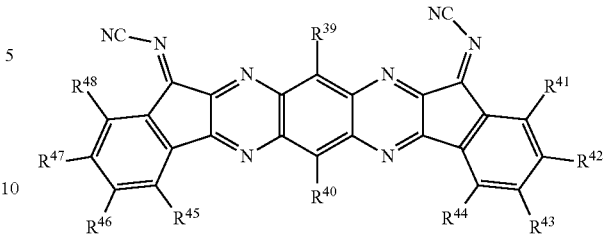

wherein $R^{31}$ to $R^{52}$ are the same as $R^1$ to $R^4$ in the formula (I) and adjacent two of $R^{31}$ to $R^{52}$ may be bonded to each other to form a ring.

14. The substrate according to claim 1, wherein the P layer of the charge-generating layer consists of the compound represented by the formula (I).

15. The substrate according to claim 1, wherein in the formula (I), $Ar^1$ is a benzene ring, a pyrazine ring, or a pyridine ring.

16. The substrate according to claim 15, wherein $R^1$ and $R^2$ are not bonded to each other to form a ring, $R^3$ and $R^4$ are not bonded to each other to form a ring, and adjacent groups of $R^1$ to $R^5$ are not bonded to each other to form a ring.

17. The substrate according to claim 16, wherein $R^1$ to $R^4$ may be the same or different from each other, and a hydrogen atom, a substituted or unsubstituted alkyl group, a substituted or unsubstituted cycloalkyl group, a substituted or unsubstituted alkenyl group, a halogen atom, a substituted or unsubstituted fluoroalkyl group, a substituted or unsubstituted alkoxy group, a substituted or unsubstituted fluoroalkoxy group, a substituted or unsubstituted amino group, a substituted or unsubstituted silyl group, or a cyano group.

18. The substrate of claim 1, wherein the anode of each organic electroluminescence device is a stripe shape.

19. The substrate of claim 1, wherein in the compound of formula (1)

$Y^1$ to $Y^4$ are —CH=;

and at least one of $R^1$ and $R^2$ and at least one or $R^3$ and $R^4$ is a substituted or unsubstituted phenyl group or a substituted or unsubstituted fluoroalkoxy group.

20. The substrate of claim 19, wherein the emitting layer disposed nearer to the cathode is a blue emitting layer comprising:

an anthracene derivative represented by the following formula (1):

(1)

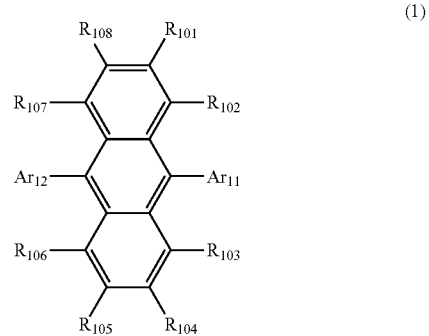

wherein $Ar_{11}$ and $Ar_{12}$ are independently a substituted or unsubstituted aryl group including 6 to 30 ring carbon atoms or a substituted or unsubstituted heterocyclic group including 5 to 30 ring atoms; and $R_{101}$ to $R_{108}$ are independently a halogen atom, a fluorine atom, a substituted or unsubstituted alkyl group including 1 to 10 carbon atoms, a substituted or unsubstituted cycloalkyl group including 3 to 10 carbon atoms, a substituted or unsubstituted alkylsilyl group including 3 to 30 carbon atoms, a substituted or unsubstituted arylsilyl group including 8 to 30 ring carbon atoms, a substituted or unsubstituted alkoxy group including 1 to 20 carbon atoms, a substituted or unsubstituted aryloxy group including 6 to 20 ring carbon atoms, a substituted or unsubstituted aryl group including 6 to 30 ring carbon atoms, or a substituted or unsubstituted heterocyclic group including 5 to 30 ring atoms, and a fused polycyclic amine derivative represented by the following formula (2)

(2)

wherein Y is a substituted or unsubstituted fused aryl group including 10 to 50 ring carbon atoms, and $Ar_{21}$ and $Ar_{22}$ are independently a substituted or unsubstituted aryl group including 6 to 50 ring carbon atoms or a substituted or unsubstituted heterocyclic group including 5 to 50 ring atoms.

* * * * *

UNITED STATES PATENT AND TRADEMARK OFFICE
CERTIFICATE OF CORRECTION

PATENT NO. : 10,411,212 B2
APPLICATION NO. : 14/349626
DATED : September 10, 2019
INVENTOR(S) : Emiko Kambe et al.

It is certified that error appears in the above-identified patent and that said Letters Patent is hereby corrected as shown below:

In the Claims

Claim 1, Column 101, Line 3:
Please delete:
"wherein the charge-generating layer comprises an N layer"
Please replace with:
"wherein the charge-generating layer consists of an N layer"

Claim 1, Column 101, Line 6:
Please delete:
"the P layer comprises a compound represented by the"
Please replace with:
"the P layer consists essentially of a compound represented by the"

Claim 1, Column 102, Line 20:
Please delete:
"a hydrogen atom, a substituted orunsubstituted alkyl,"
Please replace with:
"a hydrogen atom, a substituted or unsubstituted alkyl,"

Claim 4, Column 102, Line 55:
Please delete:
"selected from the group consisting_of an alkali metal, an"
Please replace with:
"selected from the group consisting of an alkali metal, an"

Claim 8, Column 103, Line 31:
Please delete:
"The substrate_according to claim 1, wherein at least"

Signed and Sealed this
Third Day of March, 2020

Andrei Iancu
*Director of the United States Patent and Trademark Office*

Please replace with:
"The substrate according to claim 1, wherein at least"

Claim 9, Column 104, Line 8:
Please delete:
"the aromatic heterocyclic group, or a. group formed by"
Please replace with:
"the aromatic heterocyclic group, or a group formed by"

Claim 11, Column 105, Line 1:
Please delete:
"in the formula (I-B) Ar² is the same as Ar¹ in the formula"
Please replace with:
"in the formula (I-B), Ar² is the same as Ar¹ in the formula"

Claim 13, Column 108, Lines 1-14 (1-g):
Please delete:

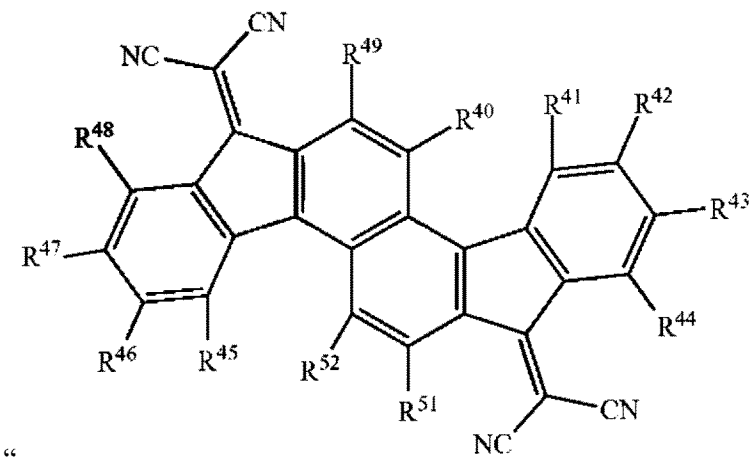

"                                                                                    "

Please replace with:

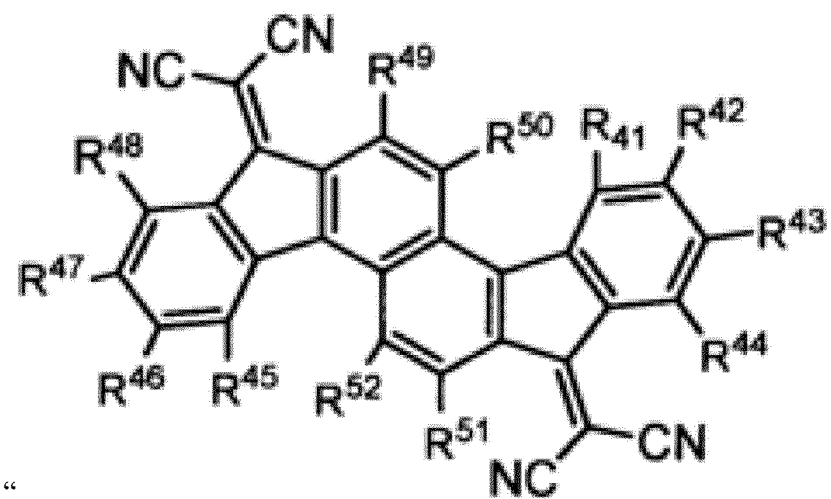

"                                                                                    "

CERTIFICATE OF CORRECTION (continued)
U.S. Pat. No. 10,411,212 B2

Claim 13, Column 108, Lines 15-25 (1-h):
Please delete:

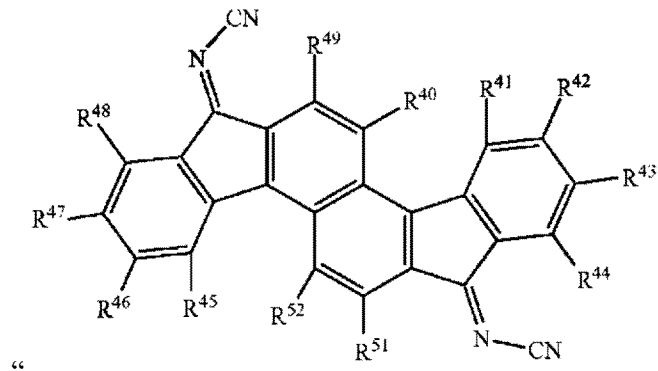

" "

Please replace with:

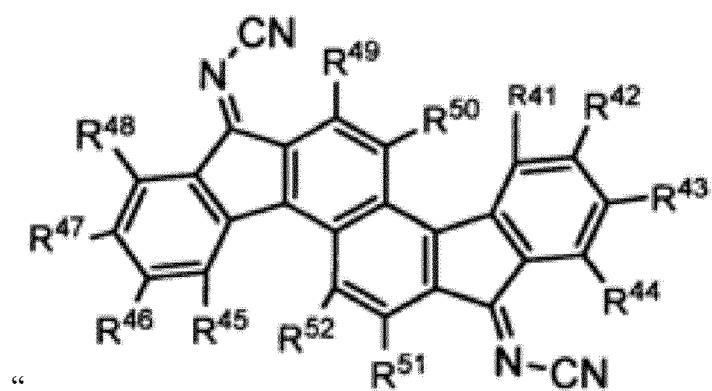

" "

Claim 13, Column 108, Lines 56-67 (1-k):
Please delete:

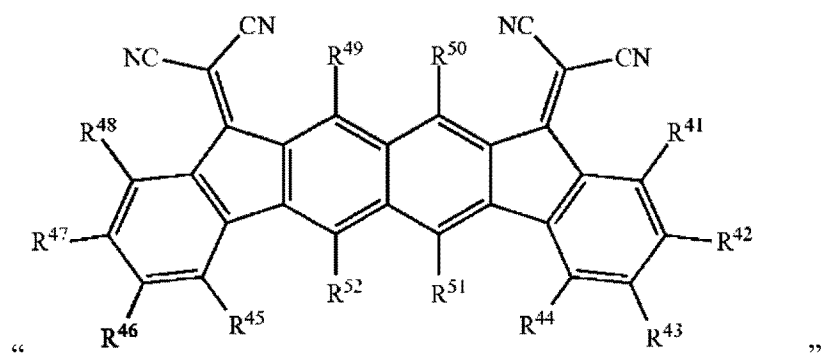

" "

CERTIFICATE OF CORRECTION (continued)
U.S. Pat. No. 10,411,212 B2

Please replace with:

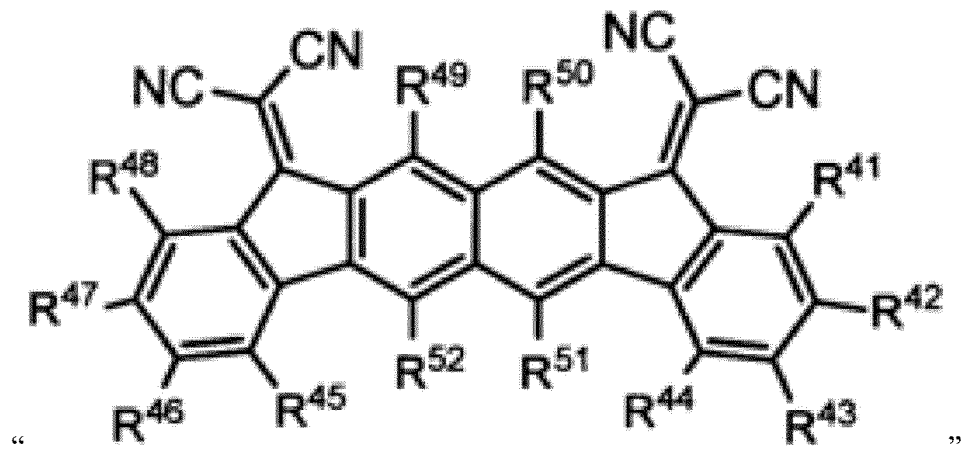

(1-k)

"                                                                 "